(12) United States Patent
Goodson, IV et al.

(10) Patent No.: US 8,012,121 B2
(45) Date of Patent: Sep. 6, 2011

(54) METHOD AND APPARATUS FOR SELECTIVE MATERIAL DELIVERY VIA AN INTRA-RENAL CATHETER

(75) Inventors: Harry B. Goodson, IV, Fremont, CA (US); Jeffrey M. Elkins, Novato, CA (US); Samir R. Patel, Mountain View, CA (US); Aurelio Valencia, East Palo Alto, CA (US); Ricardo Aboytes, East Palo Alto, CA (US); Craig A. Ball, San Carlos, CA (US); Randy J. Kesten, Mountain View, CA (US); Andrew K. Kramer, Los Gatos, CA (US); Sam G. Payne, Santa Clara, CA (US); Sophia Pesotchinsky, Los Altos Hills, CA (US); Michael H. Rosenthal, Palo Alto, CA (US)

(73) Assignee: AngioDynamics, Inc., Latham, NY (US)

( * ) Notice: Subject to any disclaimer, the term of this patent is extended or adjusted under 35 U.S.C. 154(b) by 1077 days.

(21) Appl. No.: 11/768,390

(22) Filed: Jun. 26, 2007

(65) Prior Publication Data
US 2007/0249997 A1   Oct. 25, 2007

Related U.S. Application Data

(60) Division of application No. 11/084,738, filed on Mar. 16, 2005, which is a continuation-in-part of application No. PCT/US03/29744, filed on Sep. 22, 2003.

(60) Provisional application No. 60/412,343, filed on Sep. 20, 2002, provisional application No. 60/412,476, filed on Sep. 20, 2002, provisional application No. 60/476,347, filed on Jun. 5, 2003, provisional application No. 60/502,600, filed on Sep. 13, 2003.

(51) Int. Cl.
*A61M 31/00* (2006.01)
*A61F 2/06* (2006.01)

(52) U.S. Cl. .................................. 604/93.01; 623/1.35

(58) Field of Classification Search ............... 604/93.01, 604/96.01, 101.01, 264; 623/1.35
See application file for complete search history.

(56) References Cited

U.S. PATENT DOCUMENTS 1,696,018 A   12/1928   Schellberg
(Continued)

FOREIGN PATENT DOCUMENTS

DE   4324637 A1   7/1993
(Continued)

OTHER PUBLICATIONS

"Chronic Renal Insufficiency," downloaded from internet website http://www.nutropin.com/patients/5_1_renal_insufficiency.jsp, retrieved on Nov. 13, 2006.
(Continued)

*Primary Examiner* — Theodore J Stigell
*Assistant Examiner* — Michael J Anderson
(74) *Attorney, Agent, or Firm* — Peter J. Flora

(57) ABSTRACT

Two renal delivery members have two distal ports that are adapted to be positioned within two renal arteries via their corresponding renal ostia at unique locations along an abdominal aortic wall. A proximal coupler assembly is outside the body and is coupled to deliver material to the two distal ports for bi-lateral renal therapy. One or both of the delivery members may be self-cannulating into the corresponding renal ostium, or may be controllably steered into the respective ostium. Non-occlusive anchors may be coupled with one or both of the delivery members at anchoring positions in the renal artery or abdominal aorta to secure the renal delivery member within the renal artery. Renal-active fluid agents are coupled to the bi-lateral delivery system. Another renal therapy system cannulates a renal vein from the vena cava and controls a retrograde delivery of agents to the respective kidney.

9 Claims, 45 Drawing Sheets

U.S. PATENT DOCUMENTS

| | | |
|---|---|---|
| 2,499,045 A | 2/1950 | Walker et al. |
| 3,144,868 A | 8/1964 | Jascalevich |
| 3,455,298 A | 7/1969 | Anstadt |
| 3,516,408 A | 6/1970 | Montanti |
| 3,667,069 A | 6/1972 | Blackshear et al. |
| 3,730,186 A | 5/1973 | Edmunds, Jr. et al. |
| 3,791,374 A | 2/1974 | Guarino |
| 3,841,331 A | 10/1974 | Wilder et al. |
| 3,995,623 A | 12/1976 | Blake et al. |
| 4,248,224 A | 2/1981 | Jones |
| 4,309,994 A | 1/1982 | Grunwald |
| 4,345,602 A | 8/1982 | Yoshimura et al. |
| 4,407,271 A | 10/1983 | Schiff |
| 4,423,725 A | 1/1984 | Baran et al. |
| 4,459,977 A | 7/1984 | Pizon et al. |
| 4,490,374 A | 12/1984 | Bandurco et al. |
| 4,493,697 A | 1/1985 | Krause et al. |
| 4,536,893 A | 8/1985 | Parravicini |
| 4,546,759 A | 10/1985 | Solar |
| 4,554,284 A | 11/1985 | Stringer et al. |
| 4,636,195 A | 1/1987 | Wolinsky |
| 4,685,446 A | 8/1987 | Choy |
| 4,705,502 A | 11/1987 | Patel |
| 4,705,507 A | 11/1987 | Boyles |
| 4,712,551 A | 12/1987 | Rayhanabad |
| 4,714,460 A | 12/1987 | Calderon |
| 4,723,939 A | 2/1988 | Anaise |
| 4,753,221 A | 6/1988 | Kensey et al. |
| 4,781,716 A | 11/1988 | Richelsoph |
| 4,817,586 A | 4/1989 | Wampler |
| 4,834,707 A | 5/1989 | Evans |
| 4,840,172 A | 6/1989 | Augustine et al. |
| 4,846,831 A | 7/1989 | Skillin |
| 4,861,330 A | 8/1989 | Voss |
| 4,863,461 A | 9/1989 | Jarvik |
| 4,888,011 A | 12/1989 | Kung et al. |
| 4,902,272 A | 2/1990 | Milder et al. |
| 4,902,291 A | 2/1990 | Kolff |
| 4,906,229 A | 3/1990 | Wampler |
| 4,909,252 A | 3/1990 | Goldberger |
| 4,911,163 A | 3/1990 | Fina |
| 4,919,647 A | 4/1990 | Nash |
| 4,925,377 A | 5/1990 | Inacio et al. |
| 4,925,443 A | 5/1990 | Heilman et al. |
| 4,927,407 A | 5/1990 | Dorman |
| 4,927,412 A | 5/1990 | Menasche |
| 4,938,766 A | 7/1990 | Jarvik |
| 4,950,226 A | 8/1990 | Barron |
| 4,957,477 A | 9/1990 | Lundback |
| 4,964,864 A | 10/1990 | Summers et al. |
| 4,976,691 A | 12/1990 | Sahota |
| 4,976,692 A | 12/1990 | Atad |
| 4,990,139 A | 2/1991 | Jang |
| 4,995,864 A | 2/1991 | Bartholomew et al. |
| 5,002,531 A | 3/1991 | Bonzel |
| 5,002,532 A | 3/1991 | Gaiser et al. |
| 5,044,369 A | 9/1991 | Sahota |
| 5,053,023 A | 10/1991 | Martin |
| 5,059,178 A | 10/1991 | Ya |
| 5,067,960 A | 11/1991 | Grandjean |
| 5,069,662 A | 12/1991 | Bodden |
| 5,069,680 A | 12/1991 | Grandjean |
| 5,073,094 A | 12/1991 | Dorman et al. |
| 5,087,244 A | 2/1992 | Wolinsky et al. |
| 5,089,019 A | 2/1992 | Grandjean |
| 5,098,370 A | 3/1992 | Rahat et al. |
| 5,098,442 A | 3/1992 | Grandjean |
| 5,112,301 A | 5/1992 | Fenton, Jr. et al. |
| 5,112,349 A | 5/1992 | Summers et al. |
| 5,119,804 A | 6/1992 | Anstadt |
| 5,129,883 A | 7/1992 | Black |
| 5,131,905 A | 7/1992 | Grooters |
| 5,135,474 A | 8/1992 | Swan et al. |
| 5,158,540 A | 10/1992 | Wijay et al. |
| 5,160,323 A | 11/1992 | Andrew |
| 5,163,910 A | 11/1992 | Schwartz et al. |
| 5,167,628 A | 12/1992 | Boyles |
| 5,180,364 A | 1/1993 | Ginsburg |
| 5,205,810 A | 4/1993 | Guiraudon et al. |
| 5,226,888 A | 7/1993 | Arney |
| 5,256,141 A | 10/1993 | Gencheff et al. |
| 5,257,974 A | 11/1993 | Cox |
| 5,282,784 A | 2/1994 | Willard |
| 5,290,227 A | 3/1994 | Pasque |
| 5,292,309 A | 3/1994 | Van Tassel et al. |
| 5,308,319 A | 5/1994 | Ide et al. |
| 5,308,320 A | 5/1994 | Safar et al. |
| 5,312,343 A | 5/1994 | Krog et al. |
| 5,320,604 A | 6/1994 | Walker et al. |
| 5,326,374 A | 7/1994 | Ilbawi et al. |
| 5,328,470 A | 7/1994 | Nabel et al. |
| 5,332,403 A | 7/1994 | Kolff |
| 5,345,927 A | 9/1994 | Bonutti |
| 5,358,519 A | 10/1994 | Grandjean |
| 5,364,337 A | 11/1994 | Guiraudon et al. |
| 5,370,617 A | 12/1994 | Sahota |
| 5,383,840 A | 1/1995 | Heilman et al. |
| 5,397,307 A | 3/1995 | Goodin |
| 5,411,479 A | 5/1995 | Bodden |
| 5,421,826 A | 6/1995 | Crocker et al. |
| 5,429,584 A | 7/1995 | Chiu |
| 5,453,084 A | 9/1995 | Moses |
| 5,464,449 A | 11/1995 | Ryan et al. |
| 5,476,453 A | 12/1995 | Mehta |
| 5,478,331 A | 12/1995 | Heflin et al. |
| 5,484,385 A | 1/1996 | Rishton |
| 5,505,701 A | 4/1996 | Anaya Fernandez de Lomana |
| 5,509,428 A | 4/1996 | Dunlop |
| 5,536,250 A | 7/1996 | Klein et al. |
| 5,558,617 A | 9/1996 | Heilman et al. |
| 5,569,296 A | 10/1996 | Marin et al. |
| 5,599,306 A | 2/1997 | Klein et al. |
| 5,609,628 A | 3/1997 | Keranen |
| 5,613,949 A | 3/1997 | Miraki |
| 5,613,980 A | 3/1997 | Chauhan |
| 5,617,878 A | 4/1997 | Taheri |
| 5,643,171 A | 7/1997 | Bradshaw et al. |
| 5,643,215 A | 7/1997 | Fuhrman et al. |
| 5,669,924 A | 9/1997 | Shaknovich |
| 5,702,343 A | 12/1997 | Alferness |
| 5,713,853 A | 2/1998 | Clark et al. |
| 5,713,860 A | 2/1998 | Kaplan et al. |
| 5,720,735 A | 2/1998 | Dorros |
| 5,755,779 A | 5/1998 | Horiguchi |
| 5,762,599 A | 6/1998 | Sohn |
| 5,766,151 A | 6/1998 | Valley et al. |
| 5,776,190 A | 7/1998 | Jarvik |
| 5,797,876 A | 8/1998 | Spears et al. |
| 5,807,311 A | 9/1998 | Palestrant |
| 5,807,895 A | 9/1998 | Stratton et al. |
| 5,817,046 A | 10/1998 | Glickman |
| 5,902,229 A | 5/1999 | Tsitlik et al. |
| 5,902,336 A | 5/1999 | Mishkin |
| 5,913,852 A | 6/1999 | Magram |
| 5,928,132 A | 7/1999 | Leschinsky |
| 5,935,924 A | 8/1999 | Bunting et al. |
| 5,968,013 A | 10/1999 | Smith et al. |
| 5,971,910 A | 10/1999 | Tsitlik et al. |
| 5,984,955 A | 11/1999 | Wisselink |
| 6,001,079 A | 12/1999 | Pourchez |
| 6,013,054 A | 1/2000 | Jiun Yan |
| 6,039,721 A | 3/2000 | Johnson et al. |
| 6,068,629 A | 5/2000 | Haissaguerre et al. |
| 6,077,256 A | 6/2000 | Mann |
| 6,086,527 A | 7/2000 | Talpade |
| 6,086,557 A | 7/2000 | Morejohn et al. |
| 6,096,073 A | 8/2000 | Webster et al. |
| 6,117,117 A | 9/2000 | Mauch |
| 6,117,156 A | 9/2000 | Richter et al. |
| 6,142,973 A | 11/2000 | Carleton et al. |
| 6,143,002 A | 11/2000 | Vietmeier |
| 6,156,016 A | 12/2000 | Maginot |
| 6,165,120 A | 12/2000 | Scheich, Jr. et al. |
| 6,190,349 B1 | 2/2001 | Ash et al. |
| 6,210,380 B1 | 4/2001 | Mauch |
| 6,251,133 B1 | 6/2001 | Richter et al. |
| 6,261,273 B1 | 7/2001 | Ruiz |

| | | |
|---|---|---|
| 6,261,316 B1 | 7/2001 | Shaolian et al. |
| 6,287,277 B1 | 9/2001 | Yan |
| 6,287,608 B1 | 9/2001 | Levin et al. |
| 6,325,826 B1 | 12/2001 | Vardi et al. |
| 6,387,037 B1 | 5/2002 | Boiling et al. |
| 6,390,969 B1 | 5/2002 | Boiling et al. |
| 6,468,241 B1 | 10/2002 | Gelfand et al. |
| 6,475,208 B2 | 11/2002 | Mauch |
| 6,482,211 B1 | 11/2002 | Choi |
| 6,494,875 B1 | 12/2002 | Mauch |
| 6,508,787 B2 | 1/2003 | Erbel et al. |
| 6,514,226 B1 | 2/2003 | Levin et al. |
| 6,533,747 B1 | 3/2003 | Polschegg et al. |
| 6,540,779 B2 | 4/2003 | Richter et al. |
| 6,592,567 B1 | 7/2003 | Levin et al. |
| 6,595,959 B1 | 7/2003 | Statienko et al. |
| 6,669,718 B2 | 12/2003 | Besselink |
| 6,699,231 B1 | 3/2004 | Sterman et al. |
| 6,733,474 B2 | 5/2004 | Kusleika |
| 6,749,598 B1 | 6/2004 | Keren et al. |
| 6,749,628 B1 | 6/2004 | Callol et al. |
| 6,884,258 B2 | 4/2005 | Vardi et al. |
| 6,887,258 B2 | 5/2005 | Denison et al. |
| 6,911,039 B2 | 6/2005 | Shiu et al. |
| 6,945,992 B2 | 9/2005 | Goodson et al. |
| 6,994,700 B2 | 2/2006 | Elkins et al. |
| 7,104,981 B2 | 9/2006 | Elkins et al. |
| 7,381,204 B2 | 6/2008 | Wilson et al. |
| 7,470,252 B2 | 12/2008 | Mickley et al. |
| 2001/0029349 A1 | 10/2001 | Leschinsky |
| 2001/0031907 A1 | 10/2001 | Downey et al. |
| 2002/0022857 A1 | 2/2002 | Goldsteen et al. |
| 2002/0090388 A1 | 7/2002 | Humes et al. |
| 2002/0091355 A1 | 7/2002 | Hayden |
| 2002/0165574 A1 | 11/2002 | Ressemann et al. |
| 2002/0169413 A1 | 11/2002 | Keren et al. |
| 2003/0050600 A1 | 3/2003 | Ressemann et al. |
| 2003/0069468 A1 | 4/2003 | Bolling et al. |
| 2003/0100919 A1 | 5/2003 | Hopkins et al. |
| 2003/0144636 A1 | 7/2003 | Liu |
| 2003/0153898 A1 | 8/2003 | Schon et al. |
| 2003/0181856 A1 | 9/2003 | Goldman |
| 2003/0220664 A1 | 11/2003 | Petrick et al. |
| 2004/0002730 A1 | 1/2004 | Denison et al. |
| 2004/0044302 A1 | 3/2004 | Bernard et al. |
| 2004/0064089 A1 | 4/2004 | Kesten et al. |
| 2004/0097900 A1 | 5/2004 | Keren et al. |
| 2004/0111148 A1 | 6/2004 | Goodson |
| 2004/0117003 A1 | 6/2004 | Ouriel et al. |
| 2004/0167415 A1 | 8/2004 | Gelfand et al. |
| 2004/0167463 A1 | 8/2004 | Zawacki et al. |
| 2004/0254236 A1 | 12/2004 | Dong et al. |
| 2005/0027305 A1 | 2/2005 | Shiu et al. |
| 2005/0197624 A1 | 9/2005 | Goodson et al. |
| 2005/0245882 A1 | 11/2005 | Elkins et al. |
| 2005/0245892 A1 | 11/2005 | Elkins et al. |
| 2005/0267010 A1 | 12/2005 | Goodson et al. |
| 2006/0030814 A1 | 2/2006 | Valencia et al. |
| 2006/0036218 A1* | 2/2006 | Goodson et al. .............. 604/264 |
| 2006/0047266 A1 | 3/2006 | Elkins et al. |
| 2006/0069323 A1 | 3/2006 | Elkins et al. |
| 2006/0079836 A1 | 4/2006 | Holman et al. |
| 2006/0079859 A1 | 4/2006 | Elkins et al. |
| 2006/0149350 A1 | 7/2006 | Patel et al. |
| 2006/0259066 A1 | 11/2006 | Euteneuer |
| 2007/0053904 A1 | 3/2007 | Kirst et al. |

FOREIGN PATENT DOCUMENTS

| | | |
|---|---|---|
| EP | 654283 A1 | 11/1994 |
| EP | 884064 A2 | 5/1998 |
| GB | 2239675 A | 7/1994 |
| WO | WO 97/11737 | 4/1997 |
| WO | WO 98/03213 A1 | 1/1998 |
| WO | WO 98/17347 A1 | 4/1998 |
| WO | WO 98/52639 A1 | 11/1998 |
| WO | WO 99/33407 A1 | 12/1998 |
| WO | WO 99/22784 A1 | 5/1999 |
| WO | WO 99/51286 A1 | 10/1999 |
| WO | WO 00/41612 A2 | 1/2000 |
| WO | WO 01/83016 | 4/2001 |
| WO | WO 01/37882 A | 5/2001 |
| WO | WO 01/41861 A1 | 6/2001 |
| WO | WO 01/97687 | 12/2001 |
| WO | WO 01/97717 | 12/2001 |
| WO | WO 01/97878 A1 | 12/2001 |
| WO | WO 01/97879 A1 | 12/2001 |
| WO | WO 2004/026370 A | 4/2004 |
| WO | WO 2004/032791 A | 4/2004 |
| WO | WO 2005/002660 A1 | 1/2005 |
| WO | WO 2005/014100 A1 | 2/2005 |

OTHER PUBLICATIONS

"Diabetes Mellitus," University of Maryland Medical Center webage, retrieved from http://www.umm.edu/altmed/ConsConditions/DiabetesMellituscc.html on Nov. 13, 2006.

"FDA Form 510(K) on Related Correspondence for Advanced Equipment Development, Inc."

Agostoni et al. Sustained Benefit from Ultrafiltration in Moderate Congestive heart failure Cardiology 2001:96 183-189.

Akaba, N. et al.; "A Cylinder-Shaped Balloon Catheter for the Management of Dissecting Aneurysms in Acute Stage," Herz, vol. 17, No. 6, pp. 390-393, Dec. 1992. Abstract Only.

Aspelin, et al., "Nephrotoxic Effects in high-Risk Patients Undergoing Angiography," N Engl J Med, Feb. 2003, vol. 348, No. 6, pp. 491-499.

Bakris, et al., Renal Hemodynamics in Radiocontrast Medium-Induced Renal Dysfunction etc. Kidney Internation, vol. 56 pp. 206-210 (1999).

Beregi, et al., "Doppler Flow Wire Evaluation of Renal Blood Flow Reserve in Hyertenstive Patient With Normal Renal Arteries," Cardiovascular and Interventional Radiology, vol. 23, pp. 340-346 (2000).

Bergey, E.A. et al.; "Transphepatic Insertion of Vascular Dialysis Catheters in Children: A Safe, Life-Prolonging Procedure," Pediatr. Radiol., vol. 29, No. 1, pp. 42-50, Jan. 1999. Abstract Only.

Bischoff, W. et al.; "Modified in Suty Perfusion of the Kidney Using Balloon Catheters," vol. 94, No. 30, pp. 1695-1697, Oct. 21, 1976. Abstract Only.

Briguori et al., "Contrast Agent-Assocaited Nephrotoxicity," Progess in Cardiovascular Diseases, 45;6(2003): 493-503.

Canaud, B. et al.; "Temporary Vascular Access for Extracorporeal Renal Replacement Threrapies in Acute Renal Failure Patients," Kidney Int. Suppl., vol. 66, pp. S142-S150, May 1998. Abstract Only.

Chatterjee, "Refractory hear failure-drugs and devices", European Heart Journal, 2001, 22:2227-2230.

Chu, et al. "Fenoldopam in the Prevention of Contrast Media-Induced Acute Renal Failure," The Annals of Pharmacotherapy, 35:1278-1282 (2001).

Cohn, Jay N.; "The Management of Chronic Heart Failure," The New England Journal of Medicine, pp. 490-498. Aug. 15, 1996.

Darves, "ASHP: Perioperative Fenoldopam Improves Renal Function During Major Surgery," Retrieved from the Internet [Online]: www.pslgroup.com/dg/225C72.htm, Dec. 19, 2002.

Del Greco, The Kidney in Congestive Heart Failure, Modern Concepts of Cardiovascular, Sep. 1975, vol. 44, No. 9, pp. 47-52.

D'Elia, et al., Nephrotoxicity from Angiographic Contrast Material, "A prospective Study," Am J Med, May 1982, vol. 72, pp. 719-725.

Diaz-Sandoval, et al., "Acetylcysteine to Prevent Angiography-Related Renal Tissue Injury," The Amerian Journal of Cardiology, Feb. 1, 2002: vol. 89, pp. 356-358.

Drescher, et al., Prevention of Contrast Medium-Induced Renal Vasospasm by Phosphodiesterase Inhibition, Ivest Radiol 1998; 33:858-862.

Eisenber, et al., Renal Failure After Major Angiography Can be Avoided with Hydration, AJR, May 1981; 136:859-861.

Eisenberg, et al., Renal Failure After Major Angiography, Am J Med, Jan. 1980, vol. 68, pp. 43-46.

Eisenberger, F. et al.; "Transfemoral Cannulation of the Renal Vessels. Diagnostic and Therapeutic use in Urologe," [A], vol. 16, No. 1, pp. 1-5, Jan. 1977. Abstract Only.

Elkayam, et al., Renal Hemodynamic Effects of Vasodilation with Nifedipine and Hydralazine in Patients With Heart Failure, JACC Dec. 1984; vol. 4, No. 6, pp. 1261-1267.
Elkayam, et al., Renal Vasodilatory Effect of Endothelial Stimulation in Patients with Chronic Congestive Heart Failure, J Am Coll Cardiol 1996;28:176-182.
Encarta dictionary, "Prevent," downloaded from website http://encarta.msn.com/encnet/features/dictionary/DictionaryResults.aspx?refid=1861737040, 2001, 1 page, retrieved Apr. 18, 2007.
Farncombe, "Dyspnea: assessment and treatment," Support Care Cancer, 1997, 5, 94-99.
Fox, S.L.; "Mechanisms of Contraction," Human Physiology, Fourth Edition, pp. 300-323.
Freeman, et al., "Nephopathy Requiring Dialysis After Percutaneous Coronary Intervention and the Critical role of an Adjusted Contrast Dose," *Am J Cardiol*, vol. 90, (Nov. 15, 2002) pp. 1068-1073.
Garwood, Susan et al.; "Renal Preservation Strategies for High Risk Patients,"University of Chico School Medicine, Cove Page, Table of Contents Page, pp. 1-19, 1998.
Geisburg et al., "Addressing the Challenges of Cardiorenal Syndrome," Clevland Clinic Journal of Medicine, 2006, 73, 485-491.
Gerlach, et al., "Contrast Medium-Induced Nephrotoxicity: Pathophysiology and Prevention," *Pharmacotherapy*, 2000, 20(5):540-548.
Gianello et al., Clinical Transplantation, 1995, 9, 481-489.
Greceo, B.A. et al.; "Atherosclerotic Ischemic Renal Disease," Am. J. Kidney Dis., vol. 29, No. 2, pp. 167-187, Feb. 1997. Abstractly Only.
Gruberg, et al. The prognostic implications of further renal deterioration within 48 h of interventional etc. J AM Coll Cardiol 2000, 20(5):540-548.
Halpenny et al. The effects of fendolopam on renal blood flow and tubular function during aortic cross-clamping in anaesthetized clogs, EUR J Anaetestheisol, Aug. 2000: 17(8); 491-8 Abstract.
Heyman, et al., Pathophysiology of Radiocontract Nephropathy, A Role for Medullary Hypoxia, Invest Radiol, 1999; 34:685-691.
Hobbs, et al., "An Update on Nesiritide for Treatment of Decompensated Heart Failure," *Exp. Opin. Invest. Drugs*, 2001, 10(5):935-942.
Houghton, et al., "Basal and Reserve Renal Artery Blood Flow: Effect of Endothelium-Dependent and Indendent Vasoactive Agonists and Radiographic Contrast Medium in Two Patients", *J invas Cardiol* 2000, 12: 211-215.
Hunter et al., "Preventing Contrast-Induced Nephropathy with Fenoldopam," Techniques in Vascular and Interventional Radiology. 2001. 4:1:53-56.
Iannone, L.D. et al.; "Effect of Primary Balloon Expandable Renal Artery Stents o Long-Term Patency, Renal Function, and Blood Pressure in Hypertensive and Renal Insufficient Patients with Artery Stenosis," CAthet/ Cardiovasc. Dign., vol. 37, No. 3, pp. 243-250, Mar. 1996. Abstract Only.
Jacobs, M.J. et al.; "Reduced Renal Failure Following Thoracoabdominal Aortic Aneurysym Repair by Selective Prefusion," Eur. J. Cardiothorac. Surg., vol. 14, No. 2, pp. 201-205, Aug. 1998. Abstract Only.
Katsumata T. et al. "Newly-Developed Catheter for Cardio-Renal Assist During Intraaortic Balloon Counterpulsation," Kyobu Geka, vol. 46, No. 9, pp. 767-770, Aug. 1993. Abstract Only.
Kay, et al., Acetylcysteine for Prevention of Acute Deterioration of Renal Function Following Elective Coronary Angiography and Intervention, *JAMA*, vol. 289 No. 5, (Feb. 5, 2003).
Kehrer et al.; "Construction and Experimental Application of a Catheter for Selective Arterial Kidney Perfusion in Situ," Urological Research, vol. 13, pp. 85-89, 1985.
Kim, et al., Fluriscopic Landmarks for Optimal Visualization of the Proximal Renal Arteries, JVIR, 10:37-39 (1999).
Kini et al. A protocol for Prevention of Radiographic contrast Nepropathy etc. Catheterization and Cardiovascular Interventions 2002, 55:169-173.
Kini et al. Managing the High-Risk Patient: Experience with Fenoldopam etc. Rev. Cardiovas Med 2001:2(suppl 1) S19-S25.
Kobayashi, A. et al.; "Experimental Study on the Usefulness of the Autoperfusion Balloon Catheter in Maintaining the Blood Supply to the Distal Organs," Nippon Igaku Hoshasen Gakkai Zasshi, vol. 52, No. 5, pp. 682-684, May 25, 1992. Abstract Only.
Kou-Gi Shyu et al., "Acetylcysteine Protects Against Acute Renal Damage in Patients with Abnormal Renal Function Undergoing a Coronary Procedure," The Journal of the American College of Cardiology, 2002; 40:8.
Lass, et al., Cardioascular and Renal Hemodynamic Effects of Intranenous Infusions of the Selective DA1Agonist ec., Circulation 1988; 78:1310-1315.
Levin, Howard, R. et al.; "Reversal of Chronic Ventricular Dilation in Patients with End-Stage Cardiomyopathy by Prolonged Mechanical Unloading," vol. 91, No. 11, pp. 2727-2748, Jun. 1, 1995.
Linden, R.J. et al.; "The Nature of the Atrial Receptors Responsible for a Reflex Decrease in Activity in Renal Nerves of the Dog," The Physiological Society, pp. 31-40, 1980.
Madyoon, "Clinical Experience with Use of Fenoldopam for Prevention of Radiocontrast Hephropathy etc," *Rev Cardiovasc Med*. 2001, 2(suppl 1 ); S26-S30.
Madyoon, Use of Fenoldopam to Prevent Radiocontrast Nephropathy etc. Catherization and Cardiovascular Interventions 2001, 53:341-345.
Margulies, et al., Induction and Prevention of Radiocontrast-Induced Nephropathy in Dogs with Heart Failure, Kidney Int. 1990; vol. 38:1101-1108.
Margulies, et al., Intra-Arterial Atrial Natriuetic Factor (ANF) Attenuates Radiocontrast-Induced etc., Renal Pathology, unknown date, pp. 666, Abstract only.
Masaki, Z. et al.; "In Situ Perfusion by Retrograde Cannulation of a Tumor Artery for Nephron-Sparing Surgery," Int. J. Urol, vol. 2, No. 3, pp. 161-165, Jul. 1995. Abstract Only.
Mason, et al., Renal Dysfunction After Arteriography, JAMA, 1985;253:1001-1004.
Mathis, J. M. et al.; "Use of Guide Catheter as a Temporary Stent During Microcatheter Intervention," AJNR Am. J. Neuroradiol, vol. 19, No. 5, pp. 932-933, May 1998. Abstract Only.
Mathur et al., The effects of fenoldopam, a selective dopamine receptor agonist, on renal hemodynamics etc. Abstract only. Crit Cre Med Sep. 1999: 27(9) 1832-1837.
Mathur, "The Role of the DA1 Receptor Agonist Fenoldopam in the Management of Critically Ill, Transplant, and Hypertensive Patients," *Reviews in Cardiovascular Medicine*, 2003;4(Supp 1):S35-S40.
Mccarthy, Animal Models in Medical Device Developmental and Qualification, Charles River Laboratories, vol. 10(2) 1997.
Mccullough, et al., Acute Renal Failure after Coronary Intervention: Incencence, Risk Factors, and Relationship to Mortality, Am J Med. 1997; 103:368-375.
Mehran, et al., "A Risk Score for Prediction of Contrast Induced nephropathy After Percutaneous Coronary Intervention," Retrieved from the Internet [Online]: www.abstractsinline.com/viewer, Mar. 31, 2003.
Mehran, et al., "Radiocontrast-Induced Acute Renal Failure: Allocations and Outcomes," *Rev Cardiovasc Med* 2001;2(suppl1):S9-S13.
Middleton, J. P.; "Ischemic Disease of the Kidney: How and Why to Consider Revascularization,"J. Nephrol., vol. 11, No. 3, pp. 123-136, May-Jun. 1998. Abstract Only.
Miller, et al., "Effects of Fenoldopam on Renal Blood Flow and Tubular Function Following Supraerenal Aortic Cross-Campling," *Ann Vasc Surg*, 2003, Published online Oct. 23, 2003. Abstract Only.
Mintz, et al., "Radiocontrast-Induced Nephropathy and Percutaneous Coronary Intervention," *Expert Opin. Pharmacother*., 2003; 4(5):639-652.
Mueller et al. Prevention of Contrast Media Associated Nephropathy, Arch Intern Med, Feb. 2002, vol. 162 pp. 329-336.
Murray et al., "Clinical Anesthesiology: Third Edition." McGraw-Hill Professional. New York. 2002.
Nohria et al. Medical Management of Advanced Heart Failure, JAMA, Feb. 6, 2002, vol. 162, pp. 628-640.
Novick, A.C.; "Atherosclerotic Ischemic Nephropathy. Epidemiology and Clinical Considerations," Urol. Clin. North Am., vol. 21, No. 2, pp. 195-200, May 1994. Abstract Only.
Paganini, et al., "Severity Scores and Outcomes With Acute Renal Failure in the ICU Setting," *Contrib Nephrol*, 2001; 132: 181-195.

Parfrey, et al., Contrast Material-Induced Renal Failure in Patients with Diabetes Mellitus, Renal Insufficiency, or Both, N Engl J Med, 1989, 320:149-153.

Patel, et al., Intravenous Fenoldopam Infusion in Severe Heart Failure, Cardiovasc Drugs Ther 1993; 7:97-101.

Pharmacy and Therapeutics Committe, Fenoldopam Mesylate (Corlopam) Usage Guidelines; Clinical Pharmacy Associaates, Inc. Feb. 2001. http://www.clinpharm.com/client_data/productfiles/fenoldopam%20usage%20guidelines.pdf Access Nov. 29, 2007.

Pierce, "Fenoldopam (Corlopam) DUE", Pharmacy & Therapeutics Committee, Jan. 2002, http://prodruginfo.com/Formulary/DUE/fenolddue.pdf, Accessed Sep. 12, 2007.

Postma, C.T. et al.; "Treatment of Renal Artery Stenosis with Intra-Arterial Stents," Ned Tijdshr Genneeskd., vol. 142, No. 39, pp. 2132-2137, Sep. 26, 1998. Abstract Only.

Ramanathan, et al., Ameliorating Contrast-Induced Nephropathy, Journal of Invasive Cardiology, Nov. 2001, Retrieved from the Internet [Online]: www.invasivecardiology.comlfic_20011/jic_200111f6.html.

Rebeiz, et al., "Radiocontrast Nephropathy: a Time for Affirmative Action, *J Invasive Cardiology*," Jan. 2003, vol. 15, No. 1, pp. 23-24.

Rihal, et al., "Incidence and Prognostic Importance of Acute Renal Failure After Percutaneous Coronary Intervention," *Circulation*, (May 14, 2002),105:2259-2264.

Ritchie, et al., "Use of nonionic or Low Osmolar Contrast Agents in Cardiovascular Procedures," Retrieved from the Internet [Online] www.acc.org/clinical/position/72543.htm, Jan. 22, 2003.

Robinson, et al., "Congestive Heart Failure: Targeted Drug Therapy and Invasive Interventions", Retrieved from the Internet [Online] www.speroff.com/articiesITextbook/66_CHF2.htm, printed Sep. 4, 2002.

Rudnick, et al., Nephortoxicity of Ionic and Noionic Contrast Media in 1196 Patients: A Randomized Trial, Kidney International, 1995; 47:254-261.

Schwab, et al., Contrast Nephrotoxicity: A Randomized Controlled Trial of a Nonionic and an Ionic Radiographic Contrast Agent, N Engl J Med, 1989, 320:149-153.

Seiter, H. et al.; "Modified T-Catheter and its use for Transvenous Hypothemic in Situ Perfusion in the Surgical Restoration of the Kidney with Staghorn calculi," Z. Uro Nephrol., vol. 76, No. 6, pp. 403-406, Jun. 1983. Abstract Only.

Sheifer, "Sex Differences in Coronary Atery Size", American Heart Journal, 2000; 139(4):649-653.

Shusterman, et al., Fenoldopam, But Not Nitroprusside, Improves Renal Function etc. Am J of Medicine, 95:161-168 (1993).

U.S. Appl. No. 09/165,333—Leschinsky, Boris—"Method and Apparatus for Treating Aneurysms".

Solomon, et al., Effects of Saline, Mannitol, and Furosemide on Acute Decreases in Renal Function etc., N Engl J Med 1994; vol. 331 No. 21 pp. 1416-1420.

Stevens, et al., A Prospective Randomized Trail of Prevention Measures in Patients at High Risk for Contrast Nephropathy, J Am Coll Cardiol, 1999; 33:403-411.

Strick, et al., Direct Measurement of Renal Medullary Blood Flow in the Dog, Am J. Physiol. 267 (Regulatory Integrative Comp. Physiol. 36): R253-R2259, 1994.

Suehiro, et al., "Selective Renal Vasodilation and Active Renal Artery Perfusion Improve Renal Function in Dogs with Acute Heart Failure," *The Journal of Pharmacology and Experimental Therapeutics*, vol. 298, No. 3 pp. 1154-1160 (2001).

Taliercio, et al., Risks for Renal Dysfunction with Cardiac Angiography, Annals of Internal Medicine, 1986; 104:501-504.

Thatipelli et al., "CT Angipgraphy of Renal Artery Anantomy for Evaluating Embolic Protection Devices." Journal of Vascular and Interventional Radiology. 2007; 18(7): 842-846.

Thomas, et al., Glomerrular Filtration Dynamics During Renal Vasodilation etc. Am. J. Physiol. 244:F606-F611 (1983).

Thomas, et al., Influence of Bradykinin and Papaverine on Renal etc., Renal Physiology, Basel 5:197-205 (1982).

Tumlin et al., "Fenoldopam Mesylate Blocks Reductions in Renal Plasma Flow After Radiocontrast Dye Infusion: A Pilot Trial in the Prevention of Contrast Nephropathy," The American Heart Journal, 2002; 143:5:894-903.

UIC Collge of Pharmacy, "Is Fenoldopam (Corlopam) Useful for the Prevention Of Contrast Media Associated Nephrotoxicity?", Retrieved from the Internet [Online] www.uic.edu/pharmacy/services/di/fenoldopam.htm, Jan. 2003.

Umrani et al., Beneficial effects of fenoldopam treatment of renal function in streptozotocin-induced diabetic rats, Clin Exp Hypertens, Apr. 24, 2002 (3): 207-19 Abstract only.

Van Der Zander et al., "Hypertension: Does Brain Natrriuretic Paptide Have a Direct Renal Effect in Human Hypertensives?", American Heart Association, 2003, 41, 119-123.

Vari, et al., Induction, Prevention and Mechanisms of Contrast Media-Induced Acute Renal Failure, Kidney International, 1988; 33:669-707.

Venkataramaran, "Prevention of acute renal failure," Crit. Care Clin., 2005, 21(2), 281-289 (abstract).

Walker, H.S. et al.; "Use of a Balloon-Tipped Profusion Catheter for Renal Preservation During Suprarenal Abdominal Aortic Operations," J. Vasc. Surg., vol. 2, No. 2, pp. 337-339, Mar. 1985. Abstract Only.

Weisberg et al., Risk of radiocontrast nephropathy in patients with and without diabetes mellutus, Kidney International, 1994, 45:259-265.

White, C.J. et al.; "Renal Artery Stent Placement: Utility in Lesions Difficult to Treat with Balloon Angioplasty," Am. Coll. Cardiol., vol. 30, No. 6, pp. 1445-1450, Nov. 15, 1997. Abstract Only.

Williams, D.M. et al.; "Design and Testing of a High-FLo2 Autoperfusion Catheter: An Experimental Study," J. Vasc. Interv. Radiol., vol. 3, No. pp. 285-290, May 1992. Abstract Only.

Zacherl, et al. Periarterial Papverine Applications Improves Intraoperative Kidney Function etc. Journal of Surgical Research 103:268-271 (2002).

Madyoon et al., "Fenoldopam for prevention of contrast-induced renal dysfunction in a high risk angiography population: A historically-controlled case series", Circulation vol. 104, No. Suppl. 17, XP00908219, Oct. 23, 2001, p. II-185.

Mathur, V.S., "Pathophysiology of radiocontrast nephropathy and use of fenoldopam for its prevention", Reviews in Cardiovascular Medicine, vol. 2, No. Suppl. 1, 2001, pp. 54-58, XP009098238.

Stone, G.W. et al., "Design and rationale of CONTRAST—a prospective, randomized, placebo-controlled trial of fenoldopam mesylate for the prevention of radiocontrast nephropathy", Reviews in Cardiovascular Medicine, vol. 2, No. Suppl. 1, pp. 531-536, XP009098217.

Tumlin et al., "A multicenter, double-blind, placebo-controlled trial of fenoldopam meysylate in the prevention of radiocontrast nephropathy in patients with moderate to severe renal insufficiency" Journal of the American Society of Nephrology, Vo. 11, Sep. 2000, p. 135A, XP009098223.

Tumlin, J.A. et al., Fenoldopam mesylate blocks reductions in renal plasma flow after radiocontrast dye infusion: a pilot trial in the prevention of contrast nephropathy:, American Heart Jouornal, vol. 143, No. 5, May 2002, pp. 894-903, XP002475379.

* cited by examiner

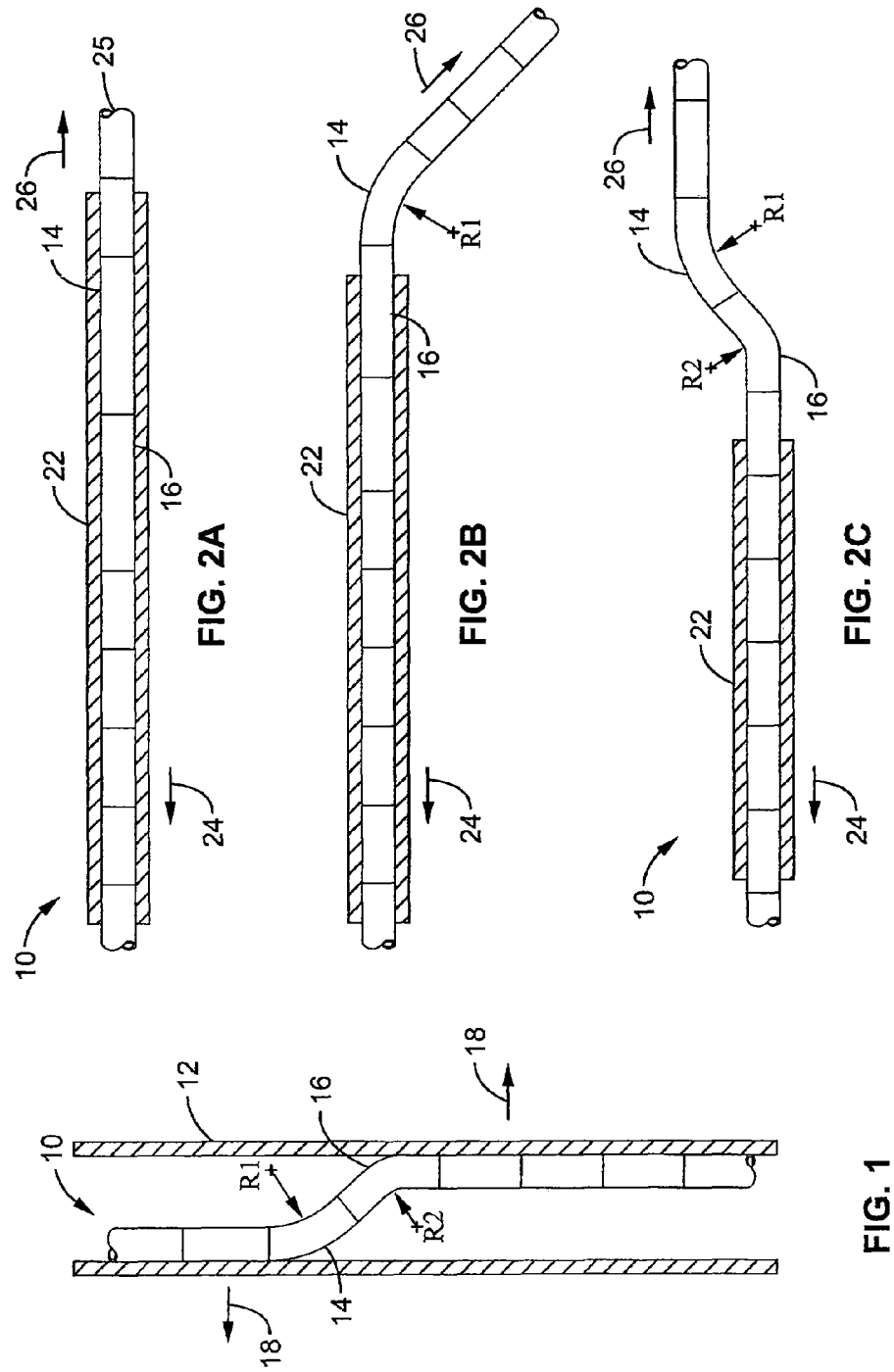

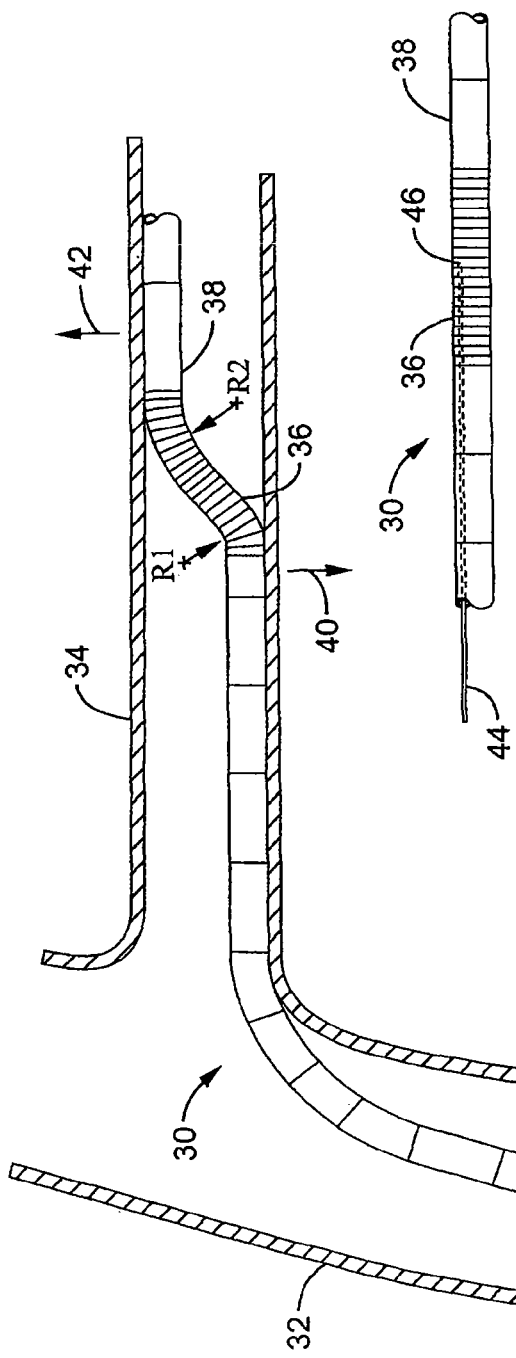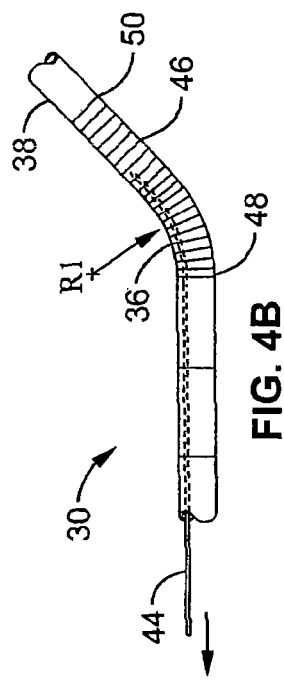

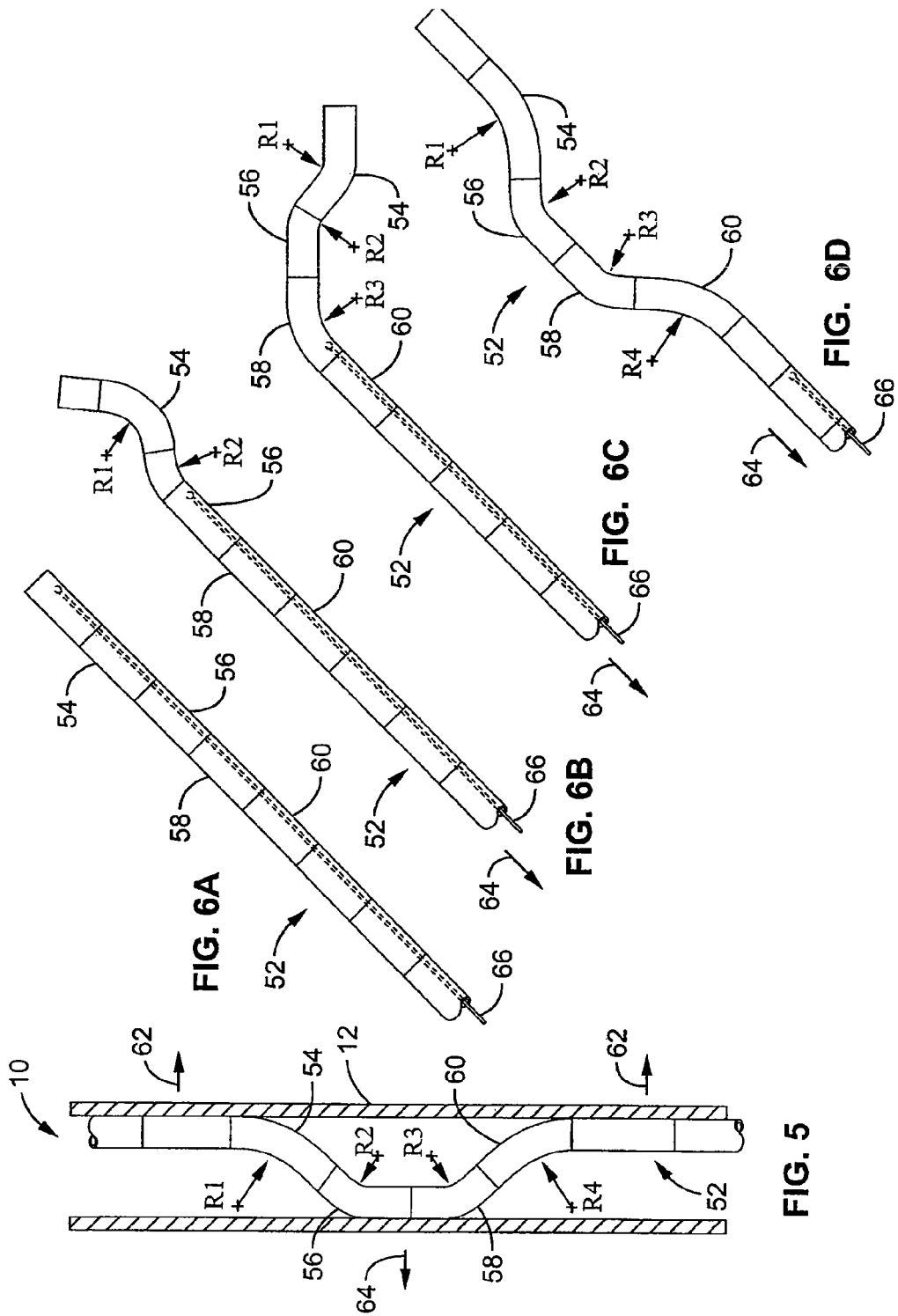

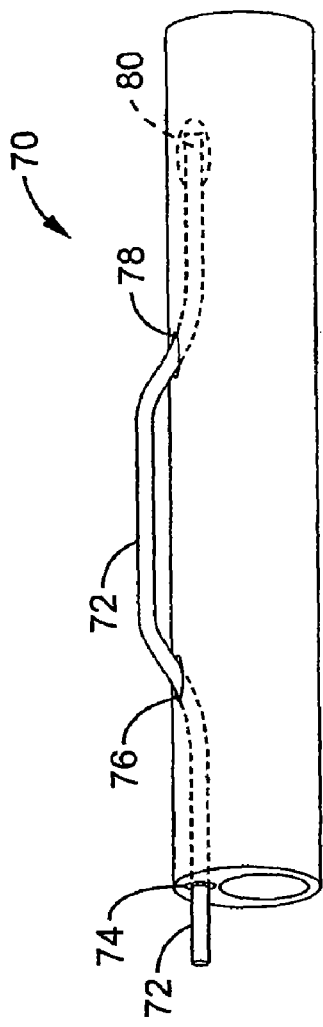
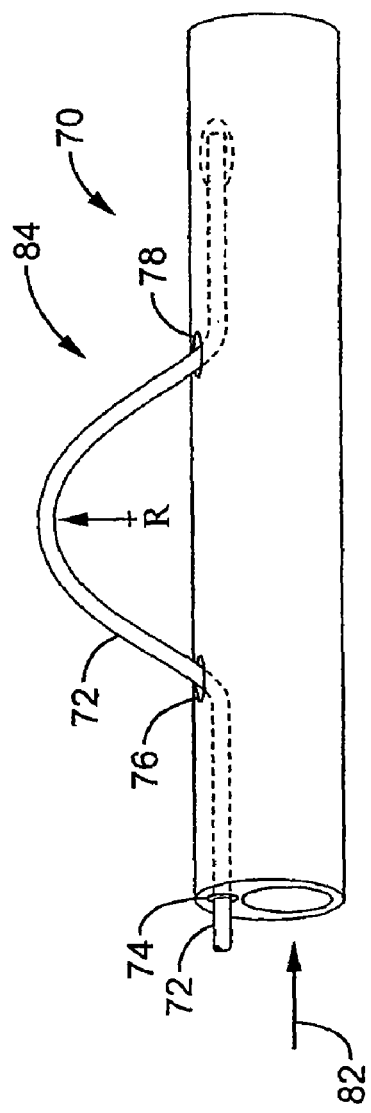

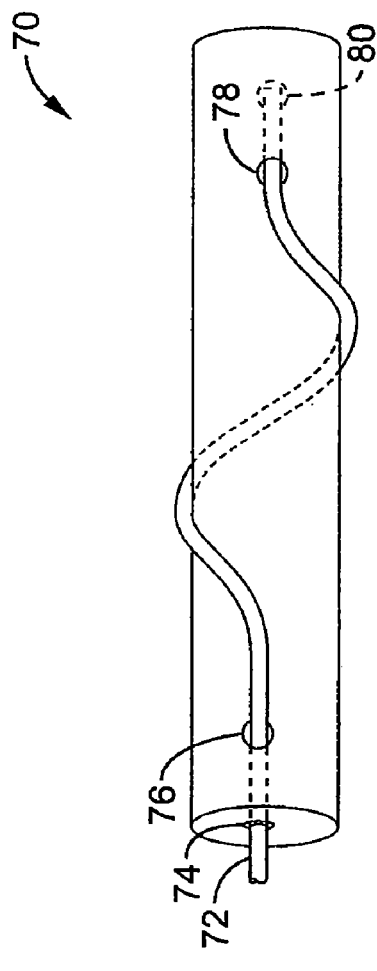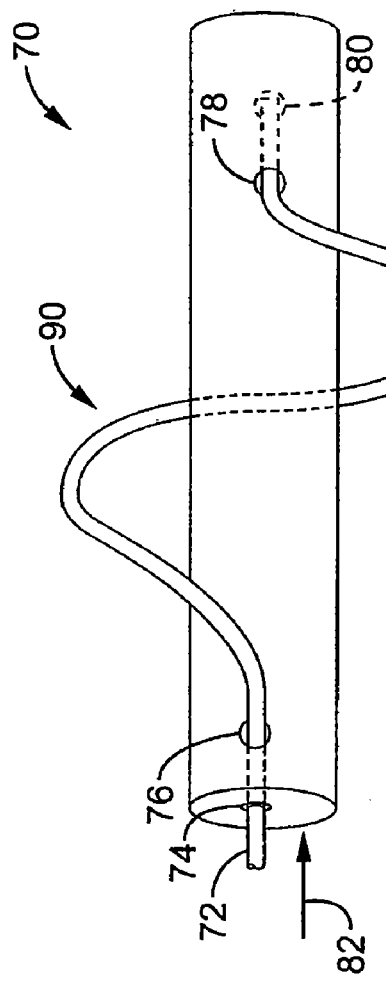

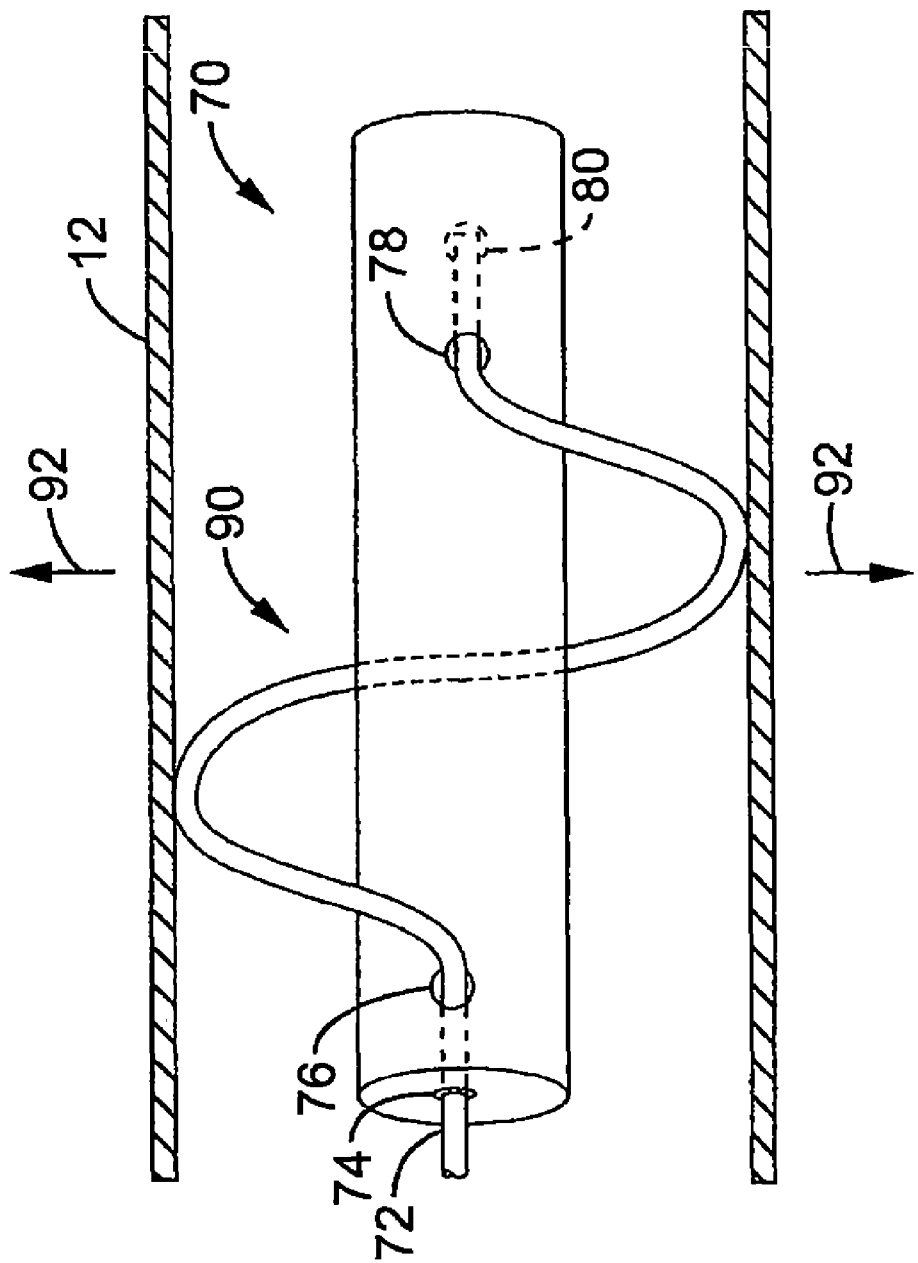

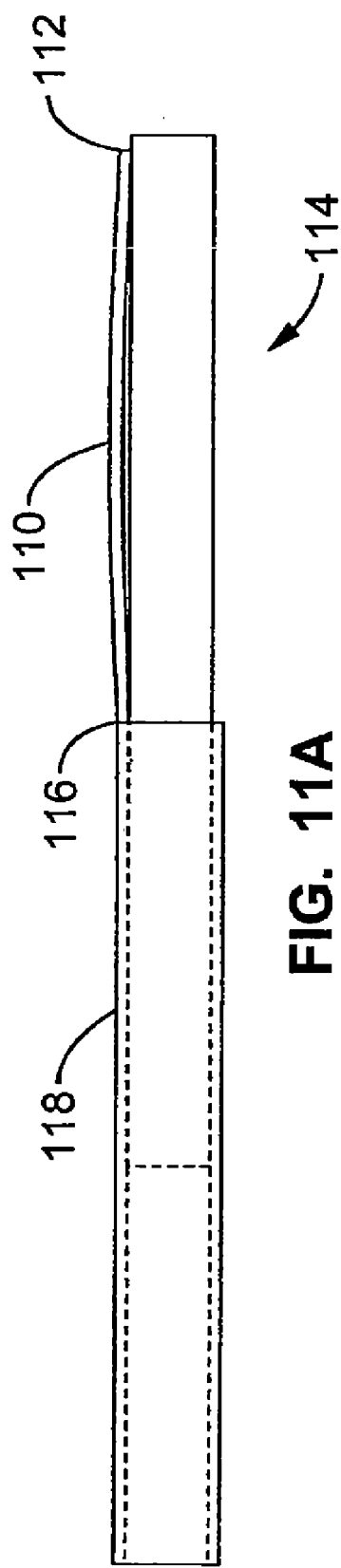
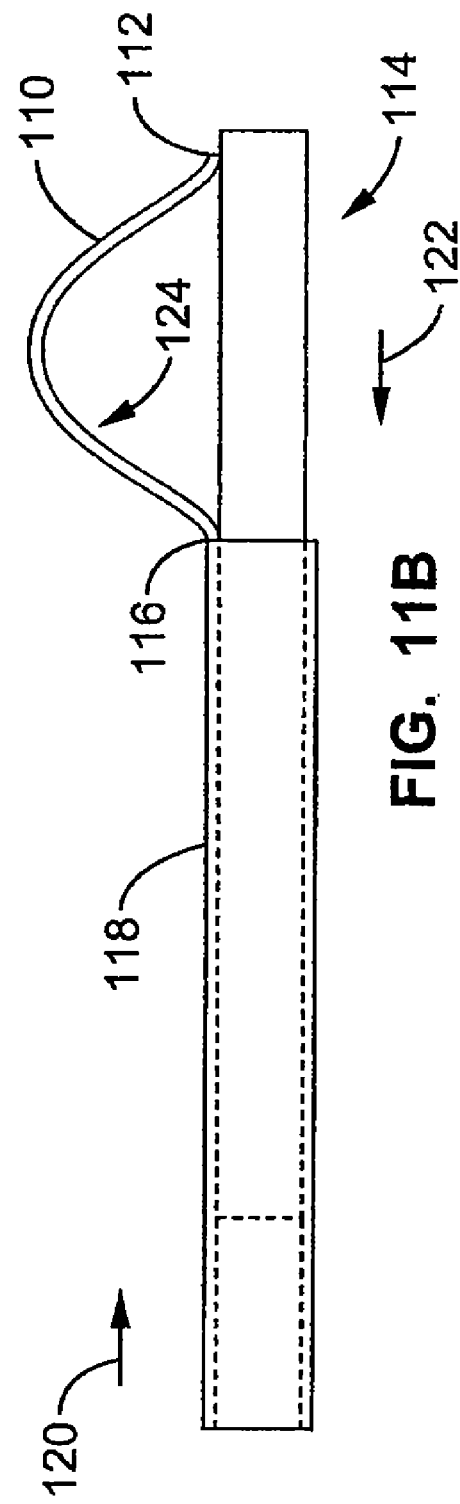

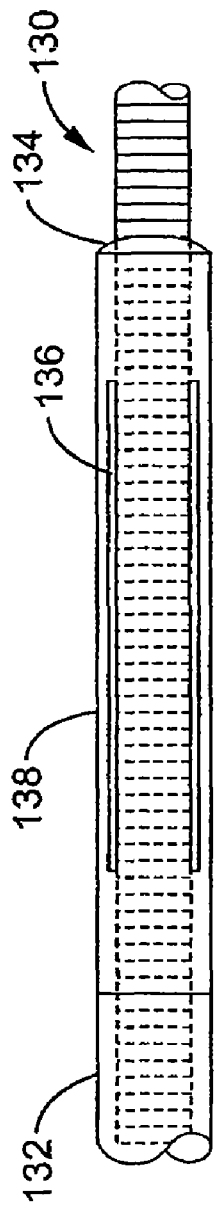
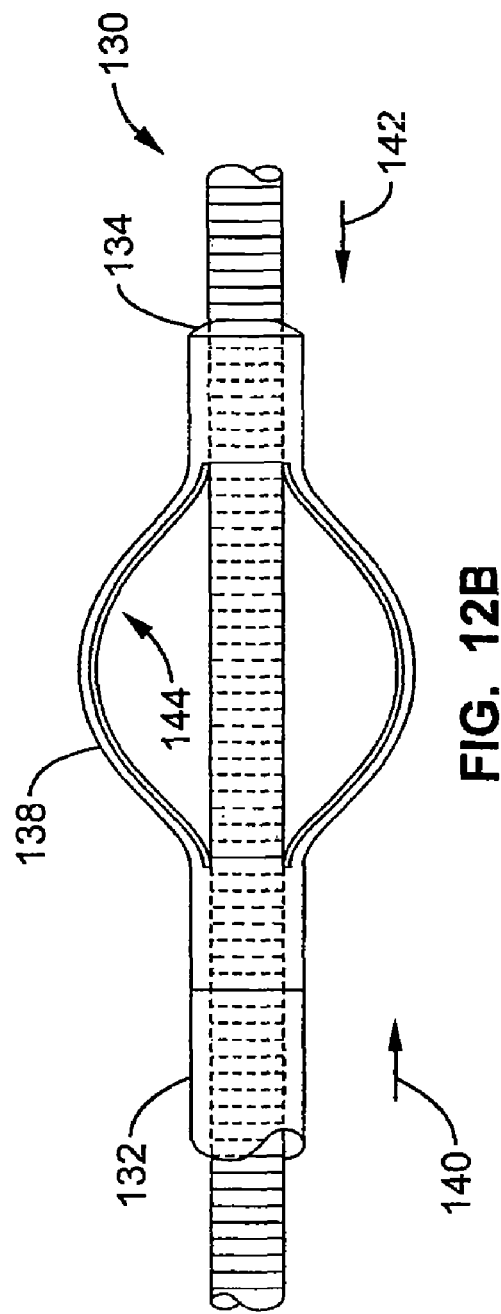

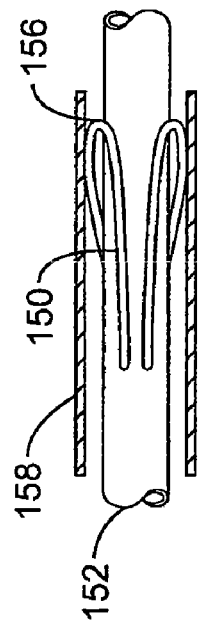
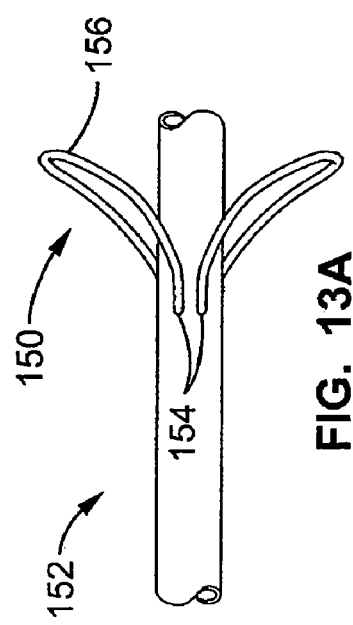
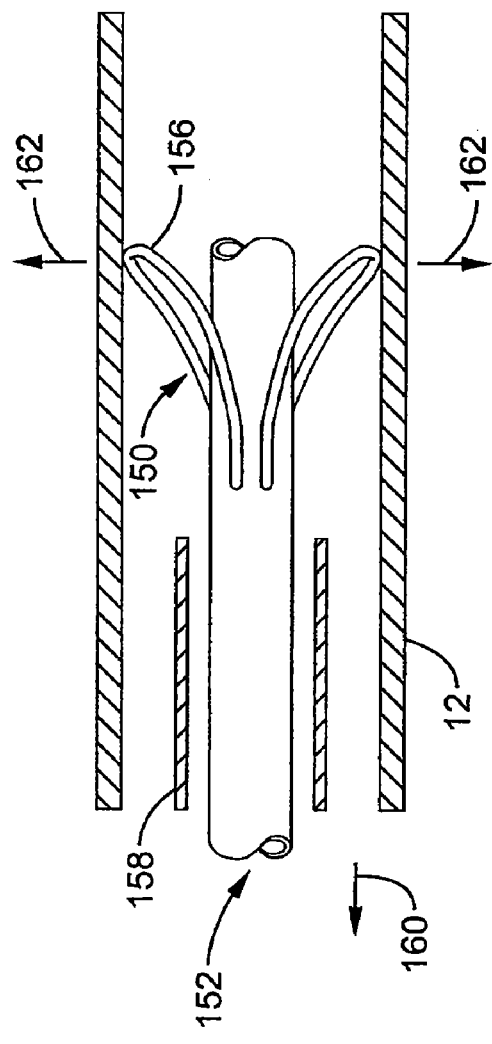

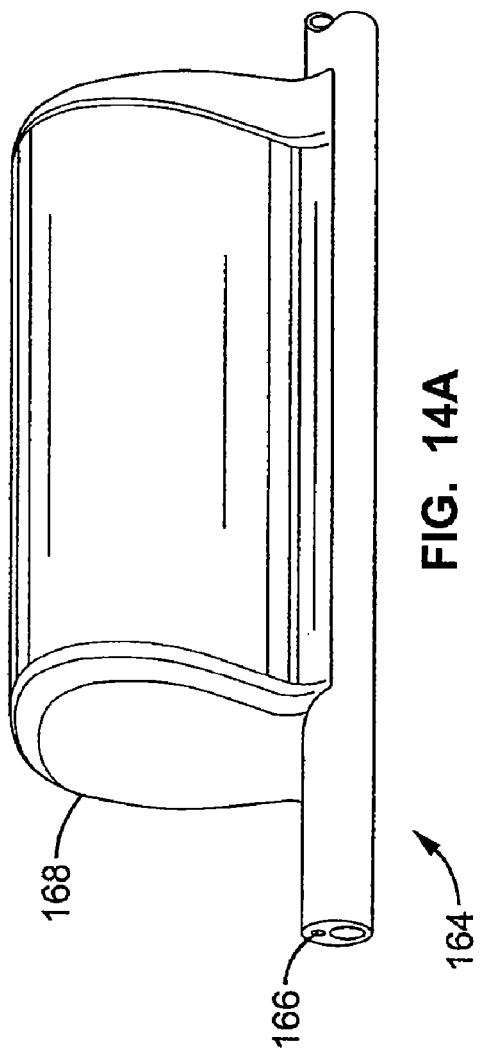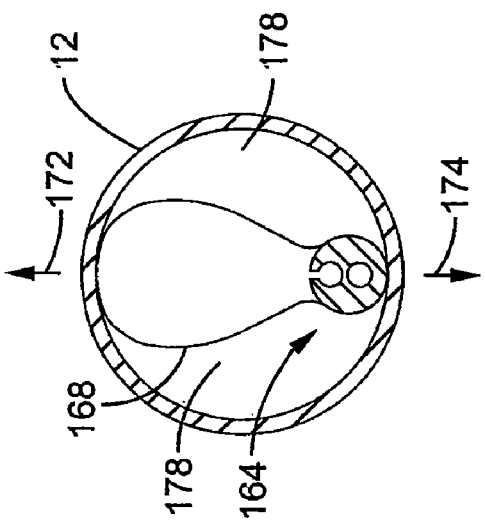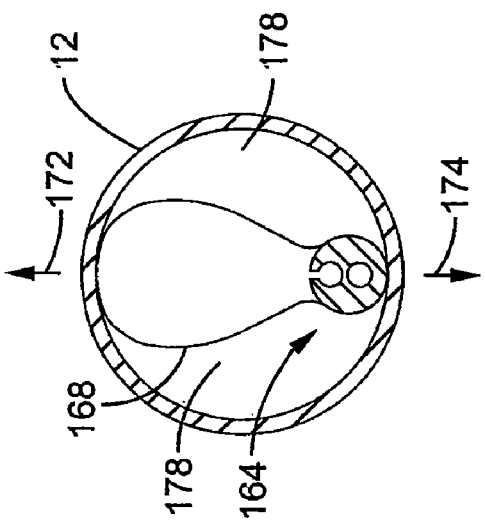

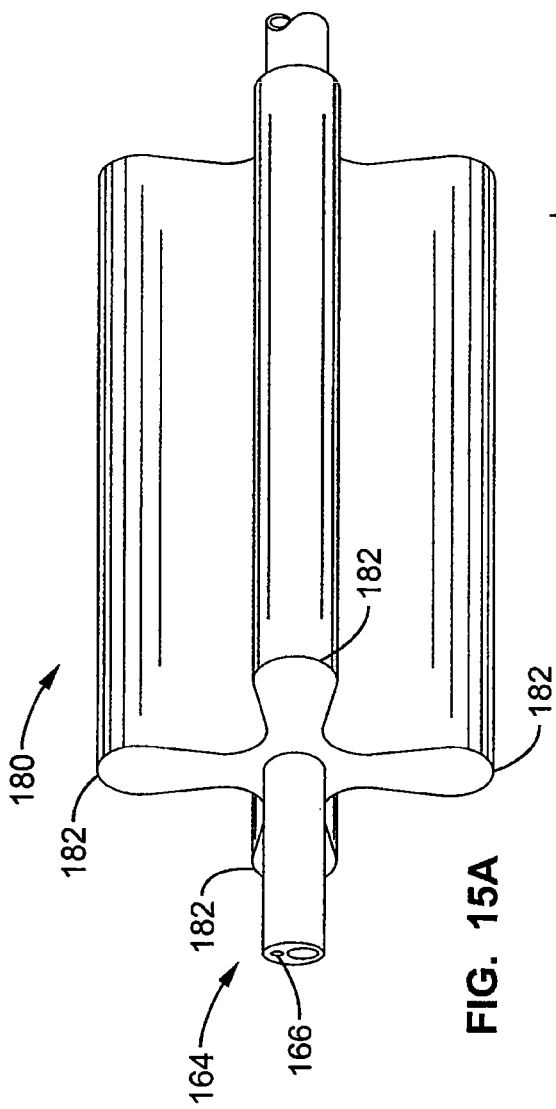
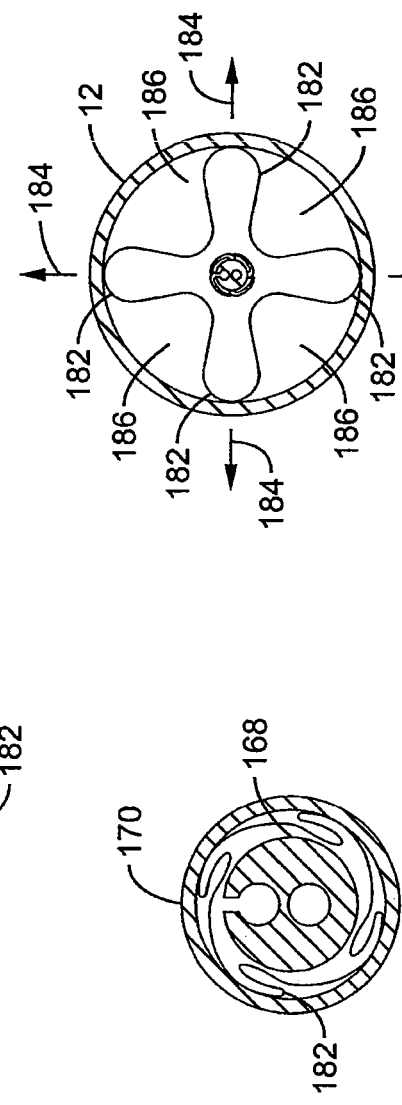
FIG. 15A
FIG. 15B
FIG. 15C

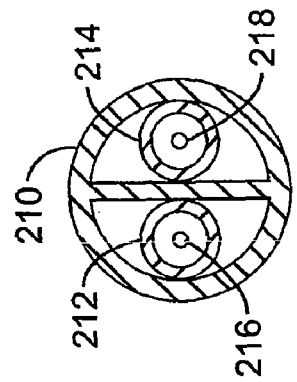
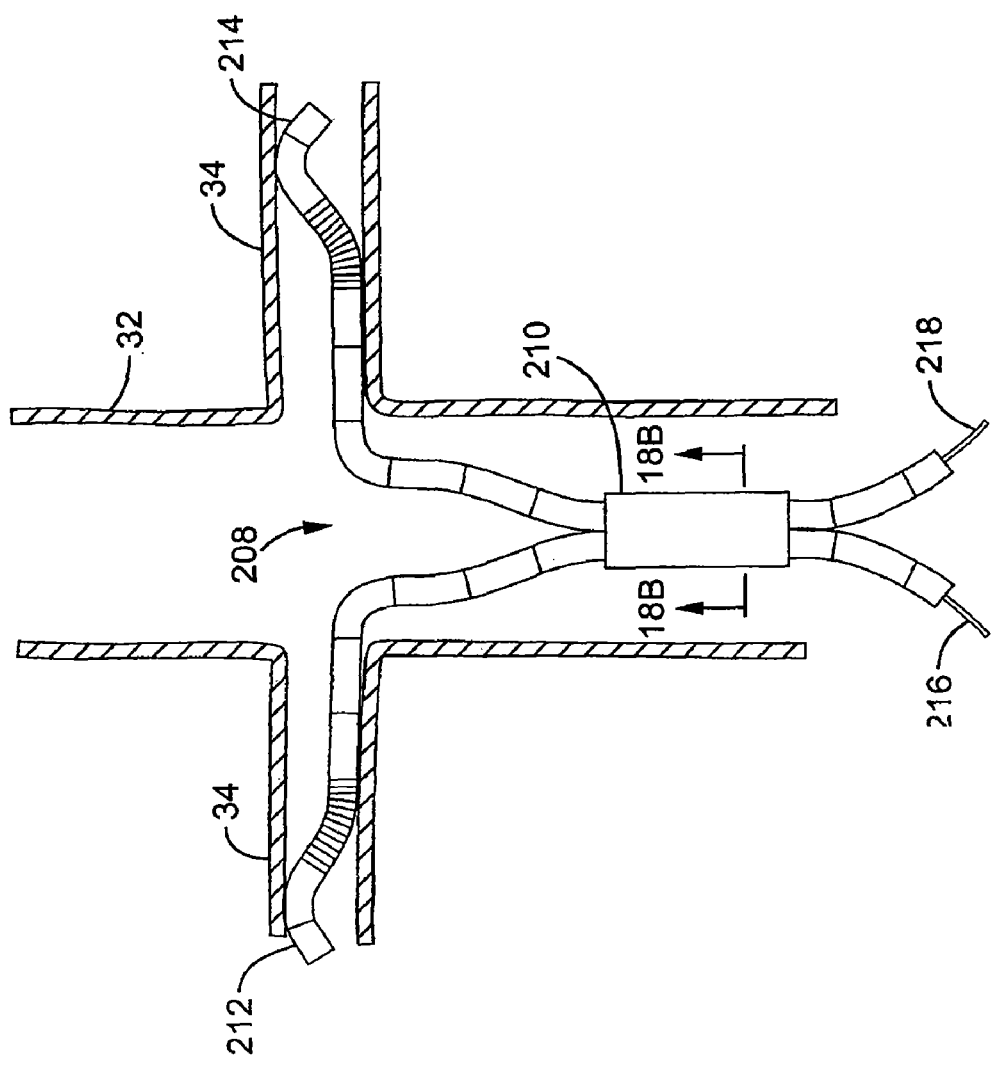

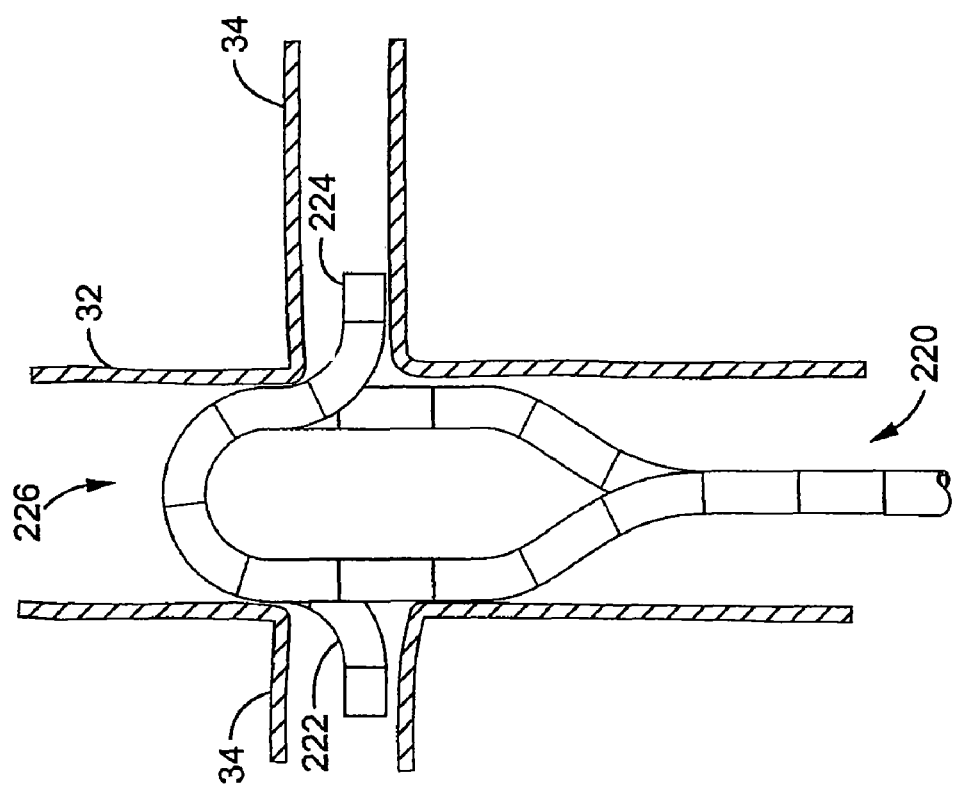

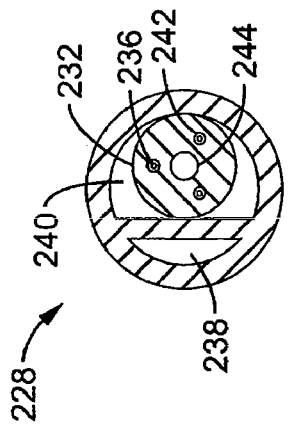
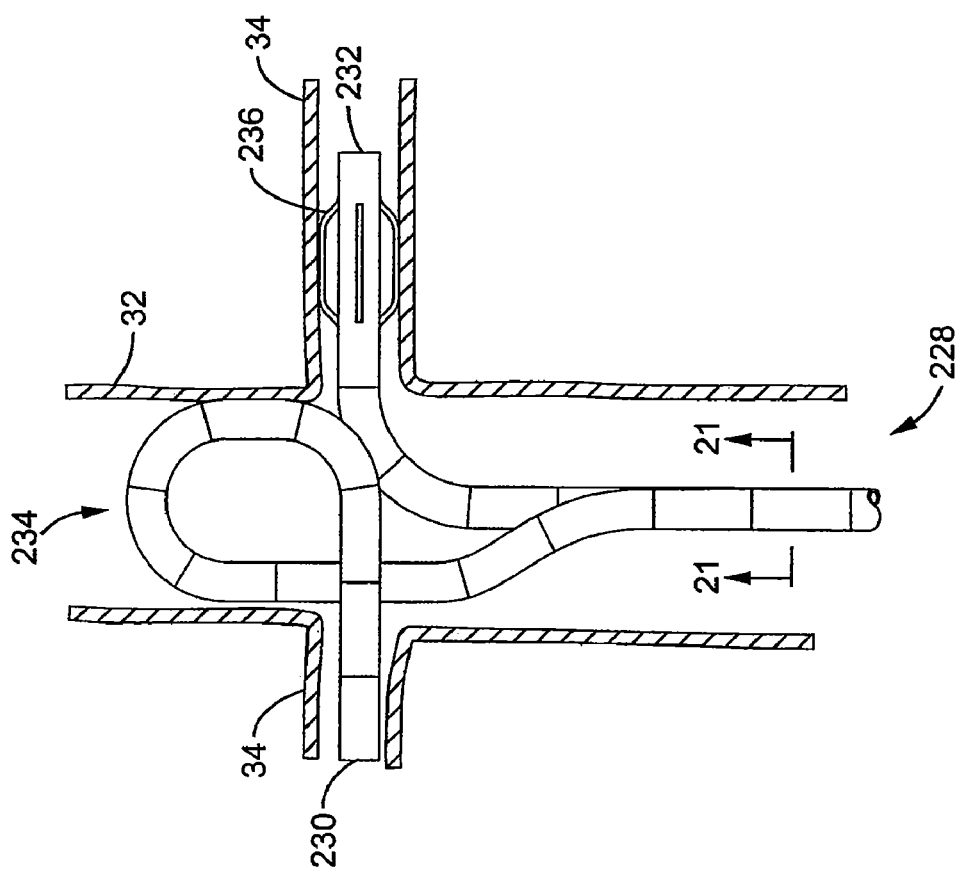

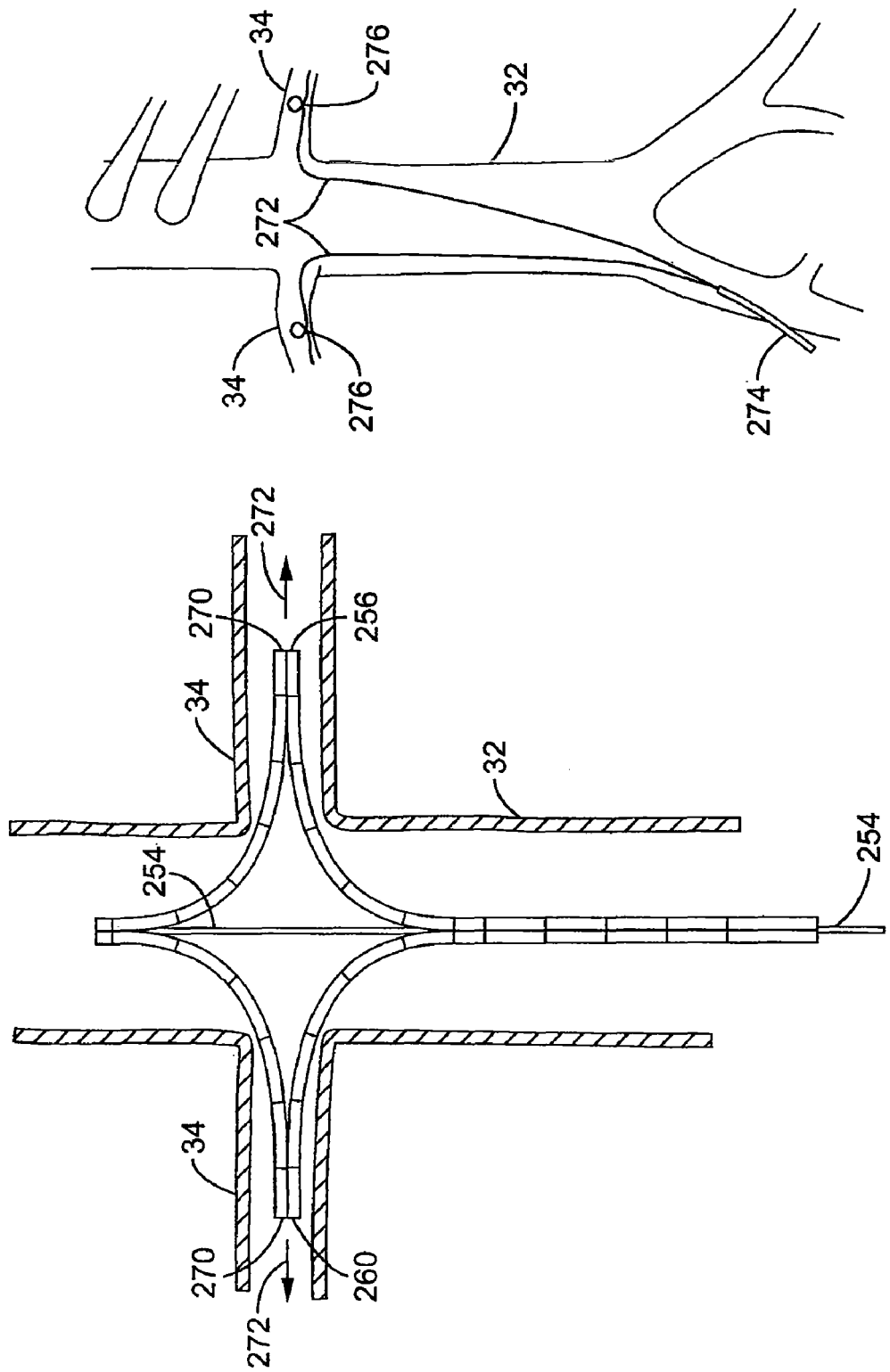

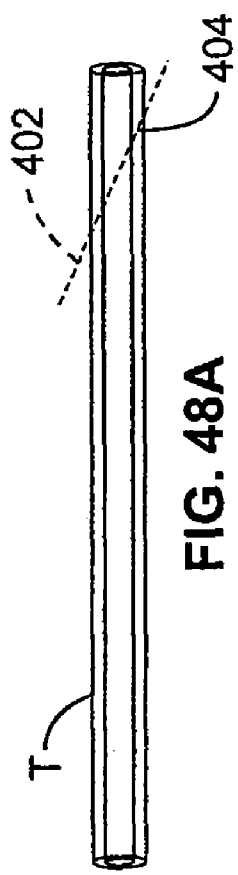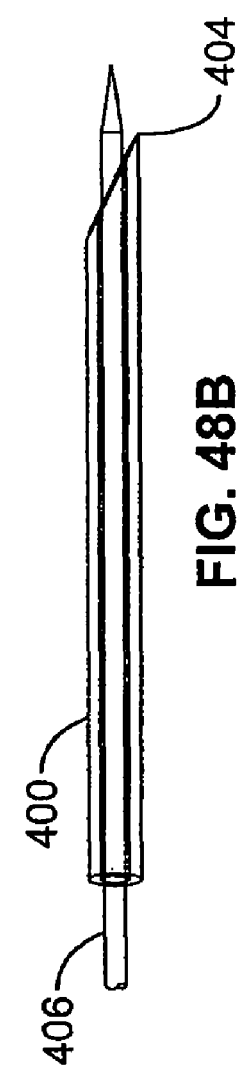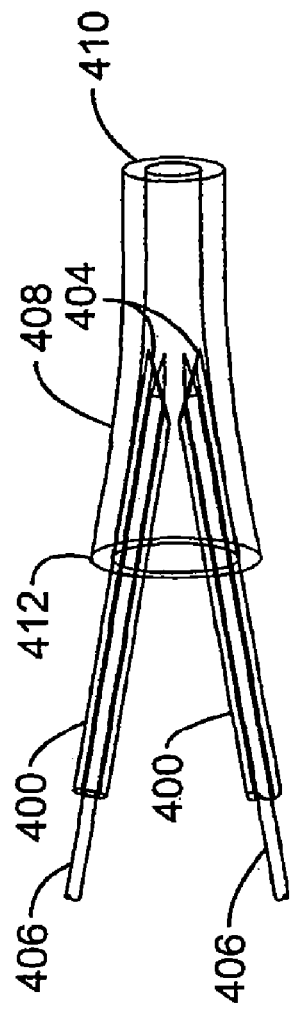

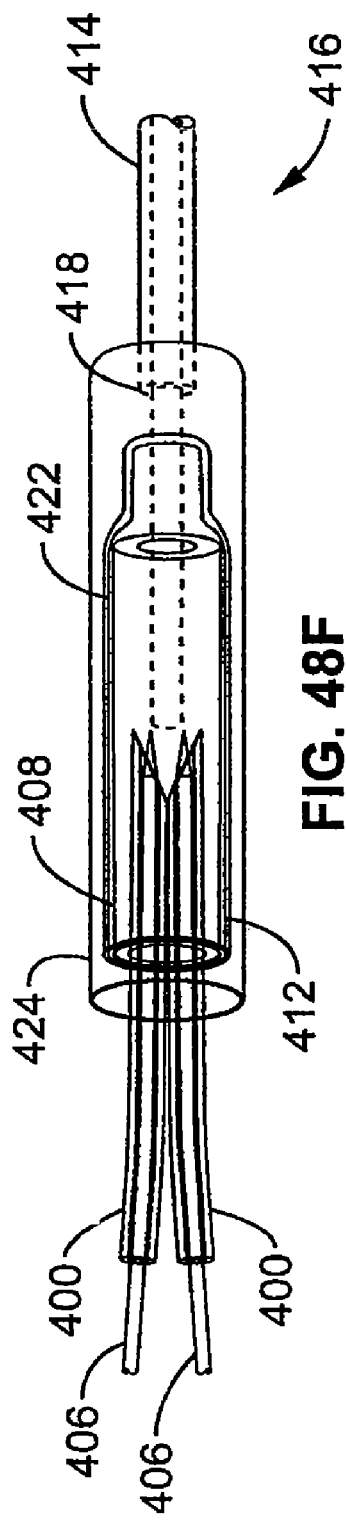
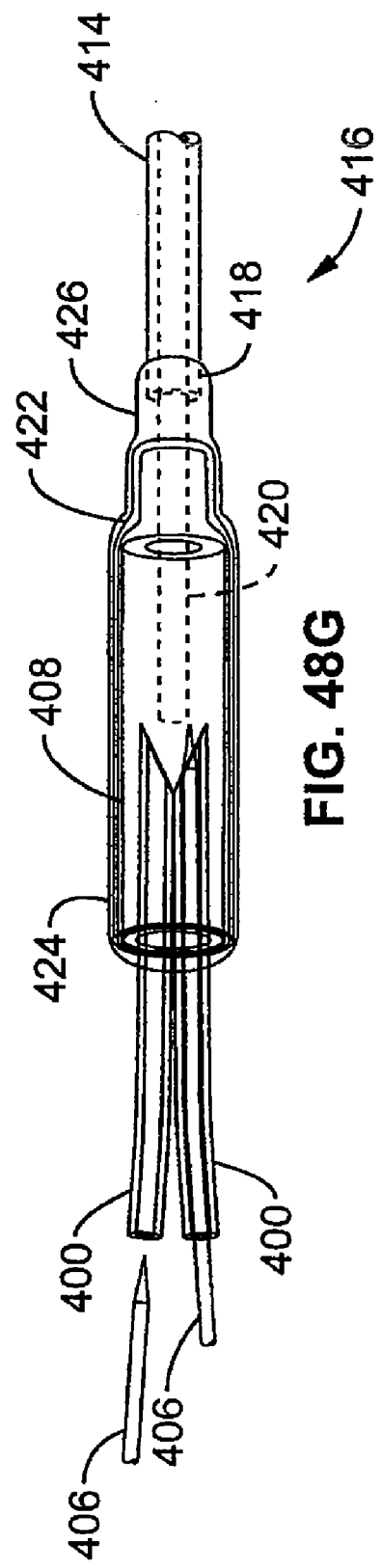
FIG. 48F
FIG. 48G

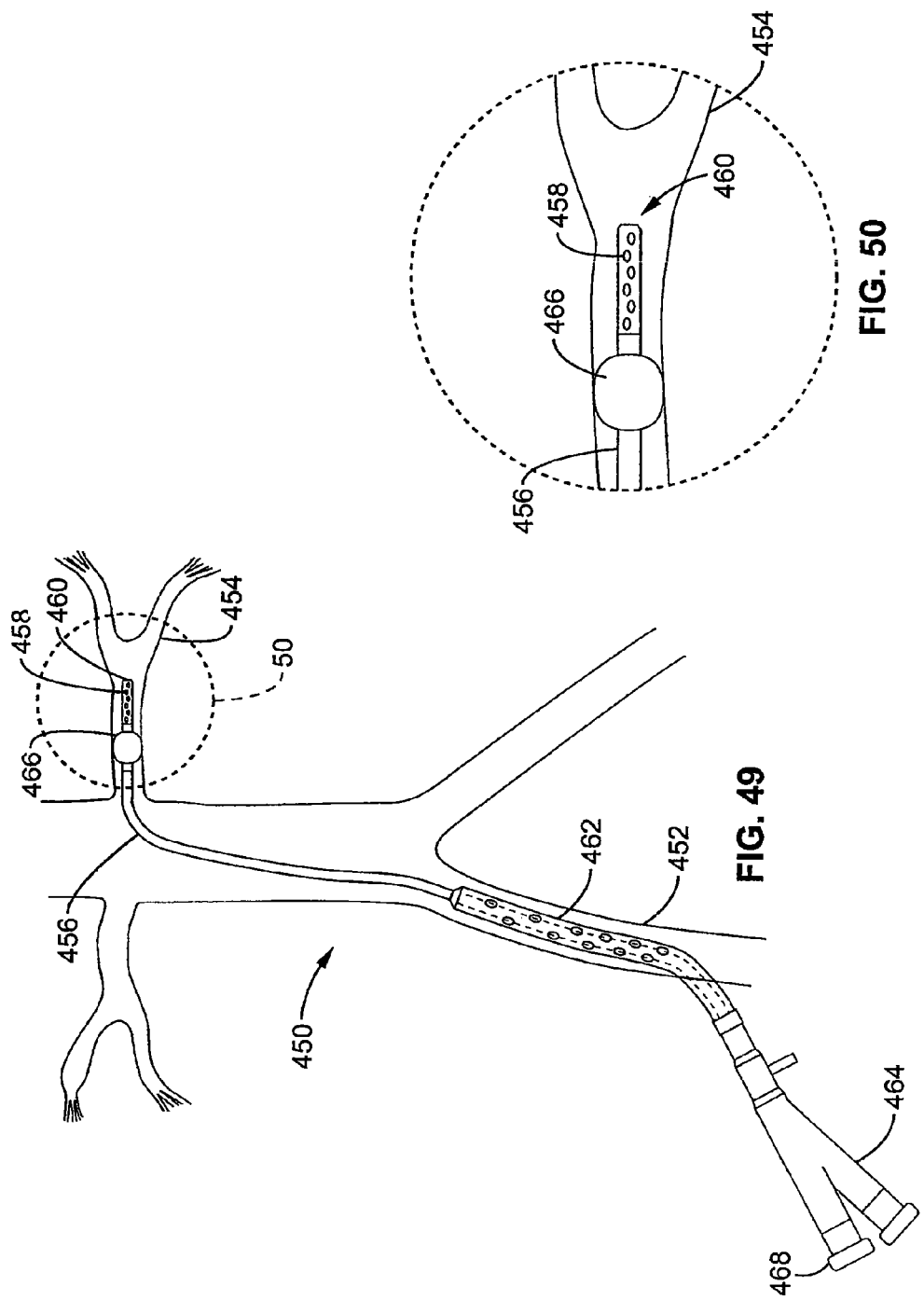

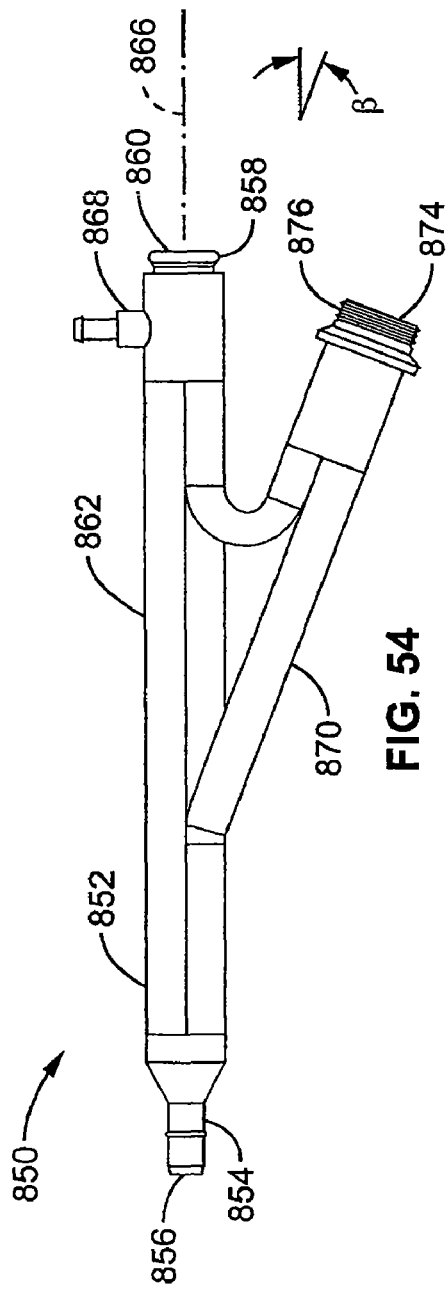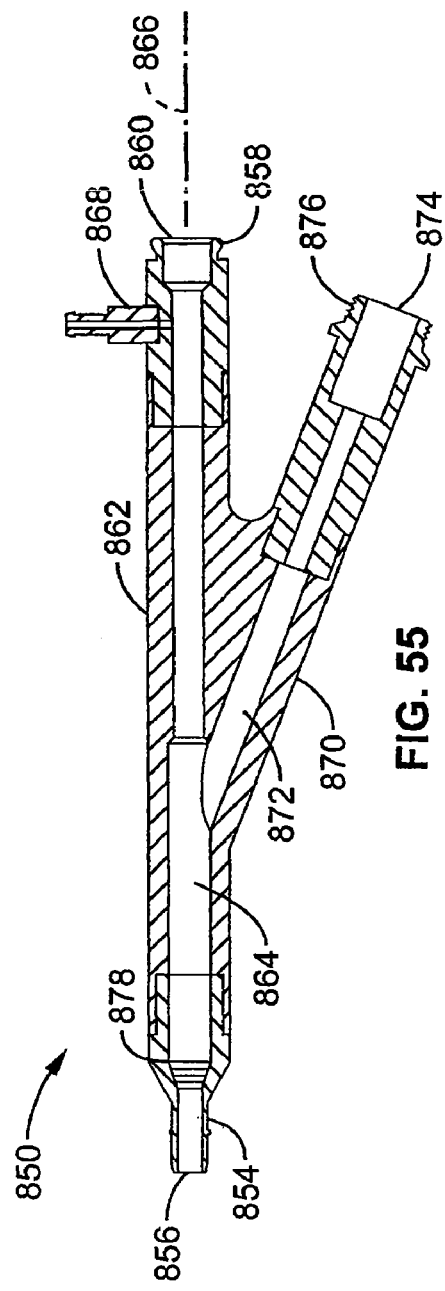

METHOD AND APPARATUS FOR SELECTIVE MATERIAL DELIVERY VIA AN INTRA-RENAL CATHETER

CROSS-REFERENCES TO RELATED APPLICATIONS

This application is divisional application of U.S. patent application Ser. No. 11/084,738, filed Mar. 16, 2005, which is a continuation-in-part of PCT Patent Application No. PCT/US03/029744, filed Sep. 22, 2003, which claims priority from U.S. Provisional Patent Application Ser. Nos. 60/412,343, filed Sep. 20, 2002; 60/412,476, filed Sep. 20, 2002; 60/476,347, filed Jun. 5, 2003; and 60/502,600, filed Sep. 13, 2003, the full disclosures of which are all hereby incorporated by reference.

BACKGROUND OF THE INVENTION

1. Field of the Invention

This invention relates to the field of medical devices, and more particularly to a system and method for locally delivering fluids or agents within the body of a patient. Still more particularly, it relates to a system and method for locally delivering fluids or agents into branch blood vessels or body lumens from a main vessel or lumen, respectively, and in particular into renal arteries extending from an aorta in a patient.

2. Description of Related Art

Many different medical device systems and methods have been previously disclosed for locally delivering fluids or other agents into various body regions, including body lumens such as vessels, or other body spaces such as organs or heart chambers. Local "fluid" delivery systems may include drugs or other agents, or may even include locally delivering the body's own fluids, such as artificially enhanced blood transport (e.g. either entirely within the body such as directing or shunting blood from one place to another, or in extracorporeal modes such as via external blood pumps etc.). Local "agent" delivery systems are herein generally intended to relate to introduction of a foreign composition as an agent into the body, which may include drug or other useful or active agent, and may be in a fluid form or other form such as gels, solids, powders, gases, etc. It is to be understood that reference to only one of the terms fluid, drug, or agent with respect to local delivery descriptions may be made variously in this disclosure for illustrative purposes, but is not generally intended to be exclusive or omissive of the others; they are to be considered interchangeable where appropriate according to one of ordinary skill unless specifically described to be otherwise.

In general, local agent delivery systems and methods are often used for the benefit of achieving relatively high, localized concentrations of agent where injected within the body in order to maximize the intended effects there and while minimizing unintended peripheral effects of the agent elsewhere in the body. Where a particular dose of a locally delivered agent may be efficacious for an intended local effect, the same dose systemically delivered would be substantially diluted throughout the body before reaching the same location. The agent's intended local effect is equally diluted and efficacy is compromised. Thus systemic agent delivery requires higher dosing to achieve the required localized dose for efficacy, often resulting in compromised safety due to for example systemic reactions or side effects of the agent as it is delivered and processed elsewhere throughout the body other than at the intended target.

Various diagnostic systems and procedures have been developed using local delivery of dye (e.g. radiopaque "contrast" agent) or other diagnostic agents, wherein an external monitoring system is able to gather important physiological information based upon the diagnostic agent's movement or assimilation in the body at the location of delivery and/or at other locations affected by the delivery site. Angiography is one such practice using a hollow, tubular angiography catheter for locally injecting radiopaque dye into a blood chamber or vessel, such as for example coronary arteries in the case of coronary angiography, or in a ventricle in the case of cardiac ventriculography.

Other systems and methods have been disclosed for locally delivering therapeutic agent into a particular body tissue within a patient via a body lumen. For example, angiographic catheters of the type just described above, and other similar tubular delivery catheters, have also been disclosed for use in locally injecting treatment agents through their delivery lumens into such body spaces within the body. More detailed examples of this type include local delivery of thrombolytic drugs such as TPA™, heparin, cumadin, or urokinase into areas of existing clot or thrombogenic implants or vascular injury. In addition, various balloon catheter systems have also been disclosed for local administration of therapeutic agents into target body lumens or spaces, and in particular associated with blood vessels. More specific previously disclosed of this type include balloons with porous or perforated walls that elute drug agents through the balloon wall and into surrounding tissue such as blood vessel walls. Yet further examples for localized delivery of therapeutic agents include various multiple balloon catheters that have spaced balloons that are inflated to engage a lumen or vessel wall in order to isolate the intermediate catheter region from in-flow or out-flow across the balloons. According to these examples, a fluid agent delivery system is often coupled to this intermediate region in order to fill the region with agent such as drug that provides an intended effect at the isolated region between the balloons.

The diagnosis or treatment of many different types of medical conditions associated with various different systems, organs, and tissues, may also benefit from the ability to locally deliver fluids or agents in a controlled manner. In particular, various conditions related to the renal system would benefit a great deal from an ability to locally deliver of therapeutic, prophylactic, or diagnostic agents into the renal arteries.

Acute renal failure ("ARF") is an abrupt decrease in the kidney's ability to excrete waste from a patient's blood. This change in kidney function may be attributable to many causes. A traumatic event, such as hemorrhage, gastrointestinal fluid loss, or renal fluid loss without proper fluid replacement may cause the patient to go into ARF. Patients may also become vulnerable to ARF after receiving anesthesia, surgery, or α-adrenergic agonists because of related systemic or renal vasoconstriction. Additionally, systemic vasodilation caused by anaphylaxis, and anti-hypertensive drugs, sepsis or drug overdose may also cause ARF because the body's natural defense is to shut down, i.e., vasoconstriction of non-essential organs such as the kidneys. Reduced cardiac output caused by cardiogenic shock, congestive heart failure, pericardial tamponade or massive pulmonary embolism creates an excess of fluid in the body, which can exacerbate congestive heart failure. For example, a reduction in blood flow and blood pressure in the kidneys due to reduced cardiac output can in turn result in the retention of excess fluid in the patient's body, leading, for example, to pulmonary and systemic edema.

Previously known methods of treating ARF, or of treating acute renal insufficiency associated with congestive heart failure ("CHF"), involve administering drugs. Examples of such drugs that have been used for this purpose include, without limitation: vasodilators, including for example papavarine, fenoldopam mesylate, calcium channel blockers, atrial natriuretic peptide (ANP), acetylcholine, nifedipine, nitroglycerine, nitroprusside, adenosine, dopamine, and theophylline; antioxidants, such as for example acetylcysteine; and diuretics, such as for example mannitol, or furosemide. However, many of these drugs, when administered in systemic doses, have undesirable side effects. Additionally, many of these drugs would not be helpful in treating other causes of ARF. For example, a septic shock patient with profound systemic vasodilation often has concomitant severe renal vasoconstriction, administering vasodilators to dilate the renal artery to a patient suffering from systemic vasodilation would compound the vasodilation system wide. In addition, for patients with severe CHF (e.g., those awaiting heart transplant), mechanical methods, such as hemodialysis or left ventricular assist devices, may be implemented. Surgical device interventions, such as hemodialysis, however, generally have not been observed to be highly efficacious for long-term management of CHF. Such interventions would also not be appropriate for many patients with strong hearts suffering from ARF.

The renal system in many patients may also suffer from a particular fragility, or otherwise general exposure, to potentially harmful effects of other medical device interventions. For example, the kidneys as one of the body's main blood filtering tools may suffer damage from exposed to high-density radiopaque contrast dye, such as during coronary, cardiac, or neuro angiography procedures. One particularly harmful condition known as "radiocontrast nephropathy" or "RCN" is often observed during such procedures, wherein an acute impairment of renal function follows exposure to such radiographic contrast materials, typically resulting in a rise in serum creatinine levels of more than 25% above baseline, or an absolute rise of 0.5 mg/dl within 48 hours. Therefore, in addition to CHF, renal damage associated with RCN is also a frequently observed cause of ARF. In addition, the kidneys' function is directly related to cardiac output and related blood pressure into the renal system. These physiological parameters, as in the case of CHF, may also be significantly compromised during a surgical intervention such as an angioplasty, coronary artery bypass, valve repair or replacement, or other cardiac interventional procedure. Therefore, the various drugs used to treat patients experiencing ARF associated with other conditions such as CHF have also been used to treat patients afflicted with ARF as a result of RCN. Such drugs would also provide substantial benefit for treating or preventing ARF associated with acutely compromised hemodynamics to the renal system, such as during surgical interventions.

There would be great advantage therefore from an ability to locally deliver such drugs into the renal arteries, in particular when delivered contemporaneous with surgical interventions, and in particular contemporaneous with radiocontrast dye delivery. However, many such procedures are done with medical device systems, such as using guiding catheters or angiography catheters having outer dimensions typically ranging between about 4 French to about 12 French, and ranging generally between about 6 French to about 8 French in the case of guide catheter systems for delivering angioplasty or stent devices into the coronary or neurovascular arteries (e.g. carotid arteries). These devices also are most typically delivered to their respective locations for use (e.g. coronary ostia) via a percutaneous, translumenal access in the femoral arteries and retrograde delivery upstream along the aorta past the region of the renal artery ostia. A Seldinger access technique to the femoral artery involves relatively controlled dilation of a puncture hole to minimize the size of the intruding window through the artery wall, and is a preferred method where the profiles of such delivery systems are sufficiently small. Otherwise, for larger systems a "cutdown" technique is used involving a larger, surgically made access window through the artery wall.

Accordingly, a local renal agent delivery system for contemporaneous use with other retrogradedly delivered medical device systems, such as of the types just described above, would preferably be adapted to allow for such interventional device systems, in particular of the types and dimensions just described, to pass upstream across the renal artery ostia (a) while the agent is being locally delivered into the renal arteries, and (b) while allowing blood to flow downstream across the renal artery ostia, and (c) in an overall cooperating system that allows for Seldinger femoral artery access. Each one of these features (a), (b), or (c), or any sub-combination thereof, would provide significant value to patient treatment; a local renal delivery system providing for the combination of all three features is so much the more valuable.

Notwithstanding the clear needs for and benefits that would be gained from such local drug delivery into the renal system, the ability to do so presents unique challenges as follows.

In one regard, the renal arteries extend from respective ostia along the abdominal aorta that are significantly spaced apart from each other circumferentially around the relatively very large aorta. Often, these renal artery ostia are also spaced from each other longitudinally along the aorta with relative superior and inferior locations. This presents a unique challenge to locally deliver drugs or other agents into the renal system on the whole, which requires both kidneys to be fed through these separate respective arteries via their uniquely positioned and substantially spaced apart ostia. This becomes particularly important where both kidneys may be equally at risk, or are equally compromised, during an invasive upstream procedure—or, of course, for any other indication where both kidneys require local drug delivery. Thus, an appropriate local renal delivery system for such indications would preferably be adapted to feed multiple renal arteries perfusing both kidneys.

In another regard, mere local delivery of an agent into the natural, physiologic blood flow path of the aorta upstream of the kidneys may provide some beneficial, localized renal delivery versus other systemic delivery methods, but various undesirable results still arise. In particular, the high flow aorta immediately washes much of the delivered agent beyond the intended renal artery ostia. This reduces the amount of agent actually perfusing the renal arteries with reduced efficacy, and thus also produces unwanted loss of the agent into other organs and tissues in the systemic circulation (with highest concentrations directly flowing into downstream circulation).

In still a further regard, various known types of tubular local delivery catheters, such as angiographic catheters, other "end-hole" catheters, or otherwise, may be positioned with their distal agent perfusion ports located within the renal arteries themselves for delivering agents there, such as via a percutaneous translumenal procedure via the femoral arteries (or from other access points such as brachial arteries, etc.). However, such a technique may also provide less than completely desirable results.

For example, such seating of the delivery catheter distal tip within a renal artery may be difficult to achieve from within the large diameter/high flow aorta, and may produce harmful intimal injury within the artery. Also, where multiple kidneys must be infused with agent, multiple renal arteries must be cannulated, either sequentially with a single delivery device, or simultaneously with multiple devices. This can become unnecessarily complicated and time consuming and further compound the risk of unwanted injury from the required catheter manipulation. Moreover, multiple dye injections may be required in order to locate the renal ostia for such catheter positioning, increasing the risks associated with contrast agents on kidney function (e.g. RCN)—the very organ system to be protected by the agent delivery system in the first place. Still further, the renal arteries themselves, possibly including their ostia, may have pre-existing conditions that either prevent the ability to provide the required catheter seating, or that increase the risks associated with such mechanical intrusion. For example, the artery wall may be diseased or stenotic, such as due to atherosclerotic plaque, clot, dissection, or other injury or condition. Finally, among other additional considerations, previous disclosures have yet to describe an efficacious and safe system and method for positioning these types of local agent delivery devices at the renal arteries through a common introducer or guide sheath shared with additional medical devices used for upstream interventions, such as angiography or guide catheters. In particular, to do so concurrently with multiple delivery catheters for simultaneous infusion of multiple renal arteries would further require a guide sheath of such significant dimensions that the preferred Seldinger vascular access technique would likely not be available, instead requiring the less desirable "cut-down" technique.

In addition to the various needs for locally delivering agents into branch arteries described above, much benefit may also be gained from simply locally enhancing blood perfusion into such branches, such as by increasing the blood pressure at their ostia. In particular, such enhancement would improve a number of medical conditions related to insufficient physiological perfusion into branch vessels, and in particular from an aorta and into its branch vessels such as the renal arteries.

Certain prior disclosures have provided surgical device assemblies and methods intended to enhance blood delivery into branch arteries extending from an aorta. For example, intra-aortic balloon pumps (IABPs) have been disclosed for use in diverting blood flow into certain branch arteries. One such technique involves placing an IABP in the abdominal aorta so that the balloon is situated slightly below (proximal to) the branch arteries. The balloon is selectively inflated and deflated in a counterpulsation mode (by reference to the physiologic pressure cycle) so that increased pressure distal to the balloon directs a greater portion of blood flow into principally the branch arteries in the region of their ostia. However, the flow to lower extremities downstream from such balloon system can be severely occluded during portions of this counterpulsing cycle. Moreover, such previously disclosed systems generally lack the ability to deliver drug or agent to the branch arteries while allowing continuous and substantial downstream perfusion sufficient to prevent unwanted ischemia.

It is further noted that, despite the renal risks described in relation to radiocontrast dye delivery, and in particular RCN, in certain circumstances local delivery of such dye or other diagnostic agents is indicated specifically for diagnosing the renal arteries themselves. For example, diagnosis and treatment of renal stenosis, such as due to atherosclerosis or dissection, may require dye injection into a subject renal artery. In such circumstances, enhancing the localization of the dye into the renal arteries may also be desirable. In one regard, without such localization larger volumes of dye may be required, and the dye lost into the downstream aortic flow may still be additive to impacting the kidney(s) as it circulates back there through the system. In another regard, an ability to locally deliver such dye into the renal artery from within the artery itself, such as by seating an angiography catheter there, may also be hindered by the same stenotic condition requiring the dye injection in the first place (as introduced above). Still further, patients may have stent-grafts that may prevent delivery catheter seating.

Notwithstanding the interest and advances toward locally delivering agents for treatment or diagnosis of organs or tissues, the previously disclosed systems and methods summarized immediately above generally lack the ability to effectively deliver agents from within a main artery and locally into substantially only branch arteries extending therefrom while allowing the passage of substantial blood flow and/or other medical devices through the main artery past the branches. This is in particular the case with previously disclosed renal treatment and diagnostic devices and methods, which do not adequately provide for local delivery of agents into the renal system from a location within the aorta while allowing substantial blood flow continuously downstream past the renal ostia and/or while allowing distal medical device assemblies to be passed retrogradedly across the renal ostia for upstream use. Much benefit would be gained if agents, such as protective or therapeutic drugs or radiopaque contrast dye, could be delivered to one or both of the renal arteries in such a manner.

Several more recently disclosed advances have included local flow assemblies using tubular members of varied diameters that divide flow within an aorta adjacent to renal artery ostia into outer and inner flow paths substantially perfusing the renal artery ostia and downstream circulation, respectively. Such disclosures further include delivering fluid agent primarily into the outer flow path for substantially localized delivery into the renal artery ostia. These disclosed systems and methods represent exciting new developments toward localized diagnosis and treatment of pre-existing conditions associated with branch vessels from main vessels in general, and with respect to renal arteries extending from abdominal aortas in particular.

However, while these approaches in one regard provide benefit by removing the need to cannulate each renal artery of the bi-lateral renal system, substantial benefit would still be gained conversely from a device system and method that allows for direct bi-lateral renal artery infusion without the need to deploy flow diverters or isolators into the high-flow abdominal aorta. In one particular example, patients that suffer from abdominal aortic aneurysms may not be suitable for standard delivery systems with flow diverters or isolators that are sized for normal arteries. In another regard, direct renal artery infusion allows for reduced occlusion to downstream aortic blood flow, or conversely more downstream flow may be preserved. Still further, the ability to truly isolate drug to only the renal system, without the potential for downstream leaking or loss into the systemic circulation, may be maximized.

A need therefore still exists for improved devices and methods for locally delivering agents bi-laterally into each of two renal arteries perfusing both kidneys of a patient while a substantial portion of aortic blood flow is allowed to perfuse downstream across the location of the renal artery ostia and into the patient's lower extremities.

A need still exists for improved devices and methods for efficiently gaining percutaneous translumenal access into each side of the kidney system via their separate renal artery ostia along the abdominal aortic wall, so that procedures such as fluid agent delivery may be performed locally within both sides of the renal system.

A need still exists for improved devices and methods for locally delivering fluid agents into a renal artery from a location within the aorta of a patient adjacent the renal artery's ostium along the aorta wall.

A need still exists for improved devices and methods for locally isolating delivery of fluids or agents into the renal arteries of a patient, and while allowing other treatment or diagnostic devices and systems, such as angiographic or guiding catheter devices and related systems, to be delivered across the location.

A need still exists for improved devices and methods for locally delivering fluids or agents into the renal arteries of a patient, for prophylaxis or diagnostic procedures related to the kidneys.

A need still exists for improved devices and methods for locally isolating delivery of fluids or agents into the renal arteries of a patient in order to treat, protect, or diagnose the renal system adjunctive to performing other contemporaneous medical procedures such as angiograms other translumenal procedures upstream of the renal artery ostia.

A need still exists for improved devices and methods for delivering both a local renal drug delivery system and at least one adjunctive distal interventional device, such as an angiographic or guiding catheter, through a common delivery sheath.

A need also still exists for improved devices and methods for delivering both a local renal drug delivery system and at least one adjunctive distal interventional device, such as an angiographic or guiding catheter, through a single access site, such as a single femoral arterial puncture.

A need also still exists for improved devices and methods for treating, and in particular preventing, ARF, and in particular relation to RCN or CHF, by locally delivering renal protective or ameliorative drugs into the renal arteries, such as contemporaneous with radiocontrast injections such as during angiography procedures.

In addition to these particular needs for selective fluid delivery into a patient's renal arteries via their ostia along the aorta, other similar needs also exist for locally isolated fluid delivery into other branch vessels or lumens extending from other main vessels or lumens, respectively, in a patient.

BRIEF SUMMARY OF THE INVENTION

Accordingly, various aspects of the invention are to be appreciated as follows.

One aspect of the invention is a local renal delivery system with two renal delivery members adapted to be positioned within first and second renal arteries and are both coupled to a proximal coupler assembly located externally of the patient's body for material delivery into the two separate arteries via the two delivery members.

In one mode of this aspect, a first renal delivery member has a first port that is adapted to be delivered to a first delivery position within a first renal artery via a first corresponding renal ostium located at a first location along an abdominal aorta wall of the abdominal aorta in a patient. A second renal delivery member has a second port that is adapted to be delivered to a second delivery position within a second renal artery via a second corresponding renal ostium located at a second location along the abdominal aorta wall that is different than the first location. The proximal coupler assembly is adapted to be located externally of the patient when the first and second ports are positioned at the first and second delivery positions, respectively. The proximal coupler assembly is also coupled to the first and second ports so as to deliver material from outside the patient's body via the proximal coupler assembly, through the first and second ports at the first and second delivery positions, respectively, and into the first and second renal arteries, also respectively.

In another mode of this aspect, the system further includes an anchor that is adjustable from a first configuration to a second configuration as follows. The anchor in the first configuration is adapted to be delivered to an anchoring position along one of the abdominal aorta or the first renal artery within the patient. The anchor is adjustable to the second configuration at the anchoring position and is thus adapted to secure the first renal delivery member with the first port substantially retained at the first delivery position within the first renal artery. The anchor in the second configuration at the anchoring position is also adapted to allow substantial blood flow across the anchoring position.

In another mode of this aspect, the first and second renal delivery assemblies together comprise a bi-lateral renal delivery system that cooperates with a vascular access system and a percutaneous translumenal interventional device as follows. The vascular access system has an elongate tubular body with at least one lumen extending between a proximal port and a distal port that is adapted to be positioned within a vessel having translumenal access to a location along the abdominal aorta associated with the first and second renal ostia when the proximal port is located externally of the patient. The percutaneous translumenal interventional device is adapted to be delivered to an intervention location across the location while the first and second ports are located at the first and second delivery positions, respectively. The bilateral renal delivery assembly and percutaneous translumenal interventional device are adapted to be delivered percutaneously into the vessel through the vascular access device, and are also adapted to be simultaneously engaged within the vascular access device.

Another aspect of the invention is a local renal delivery system with a renal delivery member adapted to be positioned within a renal artery via its ostium along an abdominal aorta wall and that is adapted to be coupled to a proximal coupler assembly located externally of the patient. An anchor is also provided to secure the renal delivery member within the renal artery without substantially occluding blood flow across the anchor.

In one mode of this aspect, the renal delivery member has a distal port that is adapted to be delivered to a delivery position within the renal artery via a corresponding renal ostium along an abdominal aorta wall. The proximal coupler assembly is adapted to be located externally of the patient when the distal port is positioned at the delivery position. The proximal coupler assembly is also fluidly coupled to the distal port so as to deliver material from outside the patient's body via the proximal coupler assembly, through the distal port at the delivery position and into the renal artery. The anchor is adjustable from a first configuration to a second configuration as follows. The anchor in the first configuration is adapted to be delivered to an anchoring position along one of the abdominal aorta or the renal artery within the patient. The anchor is adjustable from the first configuration to the second configuration at the anchoring position where it is adapted to secure the renal delivery member with the distal port substantially retained at the delivery position within the renal artery. In addition, the anchor in the second configuration at the anchoring position is adapted to allow substantial blood flow across the anchoring position.

In one embodiment of this mode, the system further includes a second renal delivery member with a second port. The second renal delivery member is adapted to be positioned at least in part within a second renal artery across a second renal ostium having a unique location with respect to the first location along an abdominal aorta wall of an abdominal aorta in the patient with respect, and such that the second port is located at a second position within the renal artery. The proximal coupler assembly is fluidly coupled to each of the first and second ports so as to deliver material from outside the patient's body via the proximal coupler assembly, through the first and second ports at the first and second respective delivery positions and into the first and second renal arteries, respectively.

Another aspect of the invention is a local renal delivery system with a vascular access system, a bi-lateral renal delivery assembly, and a percutaneous translumenal interventional device. The vascular access system is adapted to deliver the bi-lateral renal delivery assembly and the percutaneous translumenal interventional device simultaneously into the vasculature such that they can perform their respective functions.

In one mode of this aspect, the vascular access system has an elongate tubular body with at least one lumen extending between a proximal port and a distal port that is adapted to be positioned within a vessel when the proximal port is located externally of the patient. The bi-lateral renal delivery assembly includes first and second renal delivery members with first and second ports, respectively, that are adapted to be delivered to first and second respective delivery positions within first and second renal arteries, respectively, via first and second corresponding renal ostia, respectively, at unique relative locations along an abdominal aorta wall of the patient. The percutaneous translumenal interventional device is adapted to be delivered to an intervention location across the location while the first and second ports are located at the first and second delivery positions, respectively. The bi-lateral renal delivery assembly is adapted to simultaneously deliver material from an external location relative to the patient and directly into each of first and second renal arteries via first and second ports at the first and second delivery positions, respectively. The bilateral renal delivery assembly and percutaneous translumenal medical device are adapted to be delivered percutaneously into a vessel having translumenal access to the location through the vascular access device, and are also adapted to be simultaneously engaged within the vascular access device.

According to another mode, the system further includes an anchor that is adjustable from a first configuration to a second configuration as follows. The anchor in the first configuration is adapted to be delivered to an anchoring position along one of the abdominal aorta or the first renal artery within the patient. The anchor is adjustable to the second configuration at the anchoring position such that it is adapted to secure the first renal delivery member with the first port substantially retained at the first delivery position within the first renal artery. The anchor in the second configuration at the anchoring position is also constructed so as to allow substantial blood flow across the anchoring position.

According to a further embodiment of the foregoing aspects, modes, or embodiments providing first and second renal delivery members, an elongate body is provided that has a proximal end portion and a distal end portion that is adapted to be delivered to a location within the abdominal aorta when the proximal end portion extends externally from the patient. The first and second renal delivery members extend from the distal end portion of the elongate body.

In one beneficial variation of this embodiment, the first and second renal delivery members extend distally from the distal end portion of the elongate body in a bifurcated fashion.

In another beneficial variation, the distal end portion of the elongate body comprises first and second ports, and the first and second renal delivery members are moveable relative to the elongate body and are adjustable to extend from the elongate body through the first and second ports, respectively. According to a further feature of this variation, the distal end portion of the elongate body may terminate at a distal tip, the first and second ports are located at the distal tip, and the first and second renal delivery members are adjustable to extend distally from the distal tip of the elongate body through the first and second ports, respectively. According to another feature, the first and second ports are located at different positions spaced around the circumference of the elongate body proximally of the distal tip, and the first and second renal delivery members are adjustable to extend laterally from the elongate body relative to the longitudinal axis through the first and second ports.

In another beneficial variation, the first renal delivery member is substantially fixed and un-adjustable with respect to the elongate body, and the second renal delivery member is adjustable relative to the elongate body.

In another variation, a cannulation assembly is located along the distal end portion of the elongate body with a distal end, a proximal end, a length between the proximal and distal ends along a longitudinal axis, a circumference around the longitudinal axis. The first and second renal delivery members are located along the cannulation assembly at first and second circumferential locations spaced around the circumference. The cannulation assembly is adapted to be positioned at a location within the abdominal aorta associated with the first and second renal ostia. The cannulation assembly is longitudinally collapsible at the location such that the distal and proximal ends of the first and second renal delivery members are brought together with respect to each other. Accordingly, upon longitudinal collapse of the cannulation assembly, the first and second renal delivery members are biased to extend radially outward from the longitudinal axis at their respective circumferential locations such that the radially extended delivery members are adapted to cannulate the first and second renal arteries via their respective renal ostia along the location, respectively.

In another beneficial variation, the first and second delivery members are two of a plurality of more than two renal delivery members. Each delivery member extends laterally from the elongate body with a memory shape such that each terminates at a respective distal tip having a unique position circumferentially about the longitudinal axis. The memory shape of each of the plurality of renal delivery members is adapted to bias the renal delivery member against the abdominal aorta wall at a location along the abdominal aorta corresponding with the first and second renal ostia such that each renal delivery member contacts the wall at a unique lateral location around the circumference of the abdominal aorta wall relative to the other renal delivery members. The first and second renal delivery members are those renal delivery members of the plurality having their unique lateral locations corresponding with the unique locations of the first and second renal ostia, respectively. The system is further adapted to isolate delivery of material from outside the patient to only the first and second renal delivery members cannulated into the first and second renal arteries, respectively.

In still further variants to this feature, the distal tips of multiple ones of the pluralities of renal delivery members are further adapted to have unique longitudinal locations along the longitudinal axis. Or, in another regard, the first and second renal delivery members may be adjustable from a first orientation to a second orientation relative to the distal end portion of the elongate body upon cannulation of the first and second renal arteries as follows. In the first orientation the first and second ports of the first and second renal delivery members are not fluidly coupled to the proximal coupler assembly. In the second orientation the first and second ports of the first and second renal delivery members are fluidly coupled to the proximal coupler assembly.

According to another embodiment of the various aspects, modes, or embodiments providing two renal delivery members to cannulate and delivery material simultaneously to each of two renal arteries, one or both of the two renal delivery members is substantially self-cannulating with respect to the respective renal artery via the corresponding ostium along the abdominal aorta wall such that the member does not require controlled manipulation of its shape within the abdominal aorta for cannulation.

In one variation of this embodiment, the self-cannulating renal delivery member is flow-directed with respect to self-cannulation of the respective renal artery via the corresponding renal ostium along the abdominal aorta wall. In another variation, the self-cannulating renal delivery member is adapted to passively take a shape within the abdominal aorta that is adapted to self-cannulate the respective renal artery. In another variation, the self-cannulating renal delivery member is adjustable between a first shape and a second shape that is a memory shape configuration. It takes the first shape during placement within a radially confining outer sheath, and is self-adjustable from the first shape to the second shape when released from radial confinement outside of the radially confining outer sheath. The memory response toward the second shape is adapted to self-cannulate the respective renal artery.

According to another embodiment of the foregoing aspects, modes, or embodiments providing a bi-lateral renal infusion system with two renal delivery members, one or both of the renal delivery members is adapted to have a controllable shape and is selectively steerable when positioned within the abdominal aorta so as to selectively cannulate the respective renal artery via its corresponding renal ostium along the abdominal aorta wall.

According to one feature of this embodiment, a pull-wire has a distal end portion secured to the renal delivery member at a location so as to be positioned with the renal delivery member within the abdominal aorta, and a proximal end portion of the pull-wire extends proximally therefrom. Upon manipulation of the proximal end portion of the pull-wire, the distal end portion of the pull-wire manipulates the shape of the steerable renal delivery member such that it may selectively cannulate the respective renal artery via its corresponding renal ostium.

In another feature, the controllable renal delivery member has an elongate body with a stylet passageway that houses a stylet that is moveable relative to the elongate body of the at least one renal delivery member. The elongate body is adjustable from a first shape to a second shape by relative movement of the stylet between a first stylet position and a second stylet position, respectively, with respect to the elongate body of the at least one renal delivery member. The elongate body in the first shape is adapted to be delivered into the abdominal aorta through a radially confining outer sheath. The elongate body in the second shape is adapted to cannulate the respective renal artery via the corresponding ostium. The relative movement of the stylet relative to the renal delivery member controls the shape of the renal delivery member. In one further variant of this feature, the stylet has a shape; and the elongate body of the renal delivery member takes the second shape based upon the shape of the stylet. In another variant, the second shape is a memory shape condition for the elongate body, and the elongate body is adjusted from the second shape to the first shape by deflection of the elongate body of the at least one renal delivery member from the memory shape condition with the stylet.

According to another embodiment of the foregoing aspects, modes, and embodiments with a bi-lateral renal delivery system provided with two renal delivery members, the first renal delivery member is substantially self-cannulating with respect to the first renal artery via the first ostium, and the second renal delivery member is not substantially self-cannulating with respect to the second renal artery via the second ostium and has a controllable shape and is steerable so as to controllably cannulate the second renal artery via the second ostium.

According to another bi-lateral renal delivery system embodiment, the proximal coupler assembly comprises first and second proximal couplers as follows. The first proximal coupler is fluidly coupled to the first port, and the second proximal coupler is fluidly coupled to the second port.

In another bi-lateral renal delivery system embodiment, the proximal coupler assembly is a single common coupler that is fluidly coupled to each of the first and second ports via a common fluid passageway.

According to a further embodiment of the foregoing aspects, modes, or embodiments providing an anchor in the system, the anchor is a renal anchor, and the anchoring position is located along the first renal artery.

In one variation of this embodiment, the anchor includes a shapeable section of the first delivery member that is adjustable between first and second shapes that correspond with the first and second configurations, respectively, for the anchor. The anchor is adjustable from the first shape to the second shape at the anchoring position such that the second shape is biased to radially extend from the longitudinal axis of the first delivery member and is adapted to engage a wall of the first renal artery with sufficient force to secure the first delivery member with the first port at the first delivery position.

According to one feature of this variation, the anchor may include a pull-wire with a distal end portion secured to the renal delivery member at a fixed location corresponding with the shapeable section of the first delivery member, and with a proximal end portion extending proximally from the fixed location. Upon manipulation of the proximal end portion of the pull-wire, the distal end portion of the pull-wire manipulates the shape of the first renal delivery member from the first shape to the second shape.

According to another feature of the variation, the first renal delivery member has a stylet passageway that houses a stylet that is moveable relative to the shapeable section. The shapeable section is adjustable from the first shape to the second shape by relative movement of the stylet between a first stylet position and a second stylet position, respectively, within the stylet passageway along the shapeable section. In one further variant of this feature, the stylet has a shape; and the shapeable section is deflectable from the first shape to the second shape by the shape of the stylet. In another variant, the second shape comprises a memory shape condition for the shapeable section, and the shapeable section is deflectable from the second shape to the first shape by adjusting the relative position of the stylet.

In another feature, the first delivery member includes proximal and distal sections that are located proximally and distally adjacent to the shapeable section. When the anchor is in the second shape at the anchoring position, the proximal and distal sections are positioned along opposite sides of the renal artery wall. In an alternative feature, when the anchor is in the second shape at the anchoring position, the proximal and distal sections are positioned along one side of the renal artery wall and the shapeable section is biased against a second opposite side of the renal artery wall.

In another variation, the anchor has a radially extendable member located along the elongate body and that is adjustable between first and second shapes that correspond with the first and second configurations for the anchor as follows. The radially extendable member in the second shape is biased to radially extend from the elongate body relative to the first shape and is adapted to radially engage a wall of the first renal artery with sufficient force to secure the first delivery member within the first renal artery with the first delivery port at the first delivery position.

According to one feature of this variation, the radially extendable member may extend at least in part between proximal and distal locations that are spaced by a distance along an outer surface of the elongate body and where the radially extendable member is respectively engaged with the elongate body as follows. The proximal location comprises a port that communicates with a lumen within the elongate body. The radially extendable member has a length between a proximal portion and a distal portion that is longer than the distance between proximal and distal locations, such that in the first shape the proximal portion of the radially extendable member extends proximally within the port and proximally along the lumen to an internal location such that the length extends between the internal location and the distal location. In the second shape the proximal portion of the radially extendable member is advanced distally from the internal location to generally correspond with the port at the proximal location such that the length of the radially extendable member extends along a radially extended path between the proximal and distal locations externally of the elongate body within the first renal artery.

In one variant of this feature, the radially extendable member extends directly between the proximal and distal locations in the first shape. In another variant, the radially extendable member extends around a circumference of the elongate body between the proximal and distal locations. The first shape of the radially extendable member is wrapped around the elongate body between the proximal and distal locations; the second shape includes an arc that is adapted to engage the wall of the first renal artery over a portion of the circumference of the first renal artery wall.

In another variant, the second shape is a memory shape for the radially extendable member, such that the radially extendable member is adjustable to the first shape within a radially confining outer sheath. The radially extendable member is self-adjustable at the anchoring position from the first shape to the second shape by releasing the radially extendable member from radial confinement. In still a further feature of this variant, the second shape may be a partial loop shape that extends along an arc between first and second locations around the circumference of the elongate body. In another, the anchor further comprises a second said radially extendable member with a second shape that is a partial loop shape that extends along an arc along an opposite side of the elongate body. The first and second partial loop shapes are adapted to engage the first renal artery wall on opposite sides with the elongate body located within the first renal artery therebetween.

According to another variant, the radially extendable member includes an inflatable balloon that is adjustable between a deflated configuration and an inflated configuration as follows. The deflated configuration characterizes the first shape, and the inflated configuration characterizes the second shape. In one feature of this variant, the second shape characterized by the inflated condition for the balloon may be a shape that is not round. Beneficially, it may be an oblong lobe with a first diameter that spans across the first renal artery transverse to the longitudinal axis of the first renal artery so as to engage to the first renal artery wall with sufficient force to anchor the first renal delivery member there, but with a second diameter transverse to the first diameter that is less than the diameter of the first renal artery. With this shape the oblong lobe does not completely occlude the first renal artery at the anchoring position.

The second shape may also include a plurality of such oblong lobes that are arranged about the circumference of the elongate body in spaced arrangement relative to each other. In this arrangement, in the second shape each oblong lobe is adapted to radially engage a unique portion of the first renal artery wall. Blood is thus allowed to flow in the spaces between the adjacent oblong lobes.

In yet another variation, the anchor includes a plurality of radially extendable members that are located at spaced intervals around the circumference of the elongate body. Each radially extendable member in the second shape is adapted to engage the wall of the first renal artery at a different location around the circumference of the first renal artery relative to the other radially extendable members.

According to another anchoring embodiment applicable to one or more of the various aspects, modes, or embodiments above, the system includes an anchor that is an aortic anchor deployable at an anchoring position that is located along the abdominal aorta.

In one variation of this embodiment, the aortic anchor includes a shapeable section of the first renal delivery member that is adjustable between first and second shapes that correspond with the first and second configurations, respectively, for the anchor as follows. The first delivery member has proximal and distal sections located proximally and distally adjacent the shapeable section and that includes the first port. The distal section includes the first port and is adapted to be positioned within the first renal artery with the first port at the first delivery location and with the shapeable section located along the anchoring position within the abdominal aorta. The proximal section extends along a longitudinal axis where it transitions to the shapeable section. The shapeable section is adjustable from the first shape to the second shape at the anchoring position such that the second shape is biased to radially extend from the longitudinal axis and is adapted to engage a wall of the abdominal aorta at the anchoring position with sufficient force to secure the first delivery member with the first port at the first delivery position.

According to one feature of this variation, the shapeable section has a proximal region and a distal region characterized as follows. In the second shape the proximal region is radially biased to a first side of the longitudinal axis so as to contact a first side of the abdominal aorta wall, and the distal region is radially biased to a second side generally opposite the first side of the longitudinal axis so as to contact a second side generally opposite the first side of the abdominal aorta wall. The proximal and distal regions cooperate to apply generally opposite forces against the first and second sides of the abdominal aorta wall to thereby anchor the first delivery member at that location.

In a further variant of this feature, the distal region forms a loop that extends from the proximal region along the first side of the abdominal aorta, arcs across the abdominal aorta to engage the second side of the abdominal aorta, and arcs back across the abdominal aorta from the second side toward the first side. The distal section extends from the distal region extending across the abdominal aorta and into the first renal artery via the first renal ostium.

According to another anchored bi-lateral renal delivery embodiment, a second anchor is provided that is adjustable from a first configuration to a second configuration as follows. The second anchor in its respective first configuration is adapted to be delivered to a second anchoring position along one of either the abdominal aorta or the second renal artery within the patient. The second anchor in its respective second configuration at the second anchoring position is adapted to secure the second renal delivery member with the second port substantially retained at the second delivery position within the second renal artery. In addition, the second anchor in its respective second configuration at the second anchoring position is constructed so as to allow substantial blood flow from the abdominal aorta and along the second renal artery to the kidney.

In one variation of this embodiment, the first anchor is a renal anchor and the first anchoring position is within the first renal artery, and the second anchor is a renal anchor and the second anchoring position is within the second renal artery. In another variation, the first anchor is an aortic anchor and the first anchoring position is within the abdominal aorta, and the second anchor is an aortic anchor and the second anchoring position is within the abdominal aorta. Or, the first anchor may be a renal anchor with the first anchoring position located within the first renal artery, and the second anchor is an aortic anchor with the second anchoring position being located within the abdominal aorta.

According to a further embodiment of the various aspects of the invention noted above, the system further includes a source of material, and the first delivery member is adapted to deliver the material from a location externally of the patient through the first delivery port at the first delivery position and into the first renal artery.

In one highly beneficial variation of this embodiment, the source of material comprises a fluid agent, and in particular may be a renal protective agent. The fluid agent may be a diuretic, such as in particular Furosemide or Thiazide, or analog or derivative thereof. The fluid agent may be a vasopressor, such as in one particular beneficial example Dopamine, or an analog or derivative thereof. The fluid agent may be a vasodilator or otherwise a vasoactive agent. In other particular beneficial examples, the fluid agent includes Papaverine, a calcium-channel blocker, Nifedipine, Verapamil, fenoldapam mesylate, a dopamine $DA_1$ agonist, or analogs or derivatives thereof, or combinations or blends thereof.

According to further embodiments providing a bilateral renal delivery system in combination with a vascular access device and percutaneous translumenal interventional device, the percutaneous translumenal interventional device may be a delivery device to enable interventional therapy or diagnosis, such as a guiding catheter or an angiographic catheter, or may be a direct interventional device such as a recanalization device, e.g. balloon angioplasty, stenting, or atherectomy device, etc. In further variations, the system is adapted to provide such cooperative operation between these components in particular where the percutaneous translumenal interventional device is between about 4 French and about 8 French.

Another aspect of the invention is a local renal vein deliver system that provides controlled retrograde flow of material to the kidney via the renal vein as follows. The renal vein delivery member has a distal port that is adapted to be delivered to a delivery position within a renal vein via its ostium along a vena cava in a patient. A proximal coupler assembly is adapted to be located externally of the patient when the distal port is at the delivery position, and is fluidly coupled to the distal port such that a material may be delivered from outside of the patient through the proximal coupler assembly, through the distal port at the delivery position, and into the renal vein. An occlusion member is adjustable between a first configuration and a second configuration as follows. The occlusion member in the first configuration is adapted to be delivered to an occlusion position located toward ostium from the delivery position, such that the distal port and occlusion members are located at the delivery and occlusion positions, respectively. The occlusion member in the second configuration at the occlusion position is adapted to substantially occlude flow from the renal vein and into the vena cava. A control system is provided and is adapted to control cooperative operation of the renal vein delivery assembly and the occlusion member between first and second modes of operation as follows. In the first mode the occlusion member is in the first configuration at the occlusion position and venous blood is allowed to flow from the kidney and along the renal vein and into the vena cava. In the second mode the occlusion member is in the second configuration at the occlusion position, venous blood is substantially occluded from flowing from the kidney along the renal vein and into the vena cava, and a volume of fluid agent flows through the distal port at the delivery position and into the renal vein at sufficient pressure to provide retrograde flow into the respective kidney coupled to the renal vein.

According to one further mode of this aspect, a second renal delivery member is also provided and has a second port that is adapted to be delivered to a second delivery position within a second renal vein via a second ostium having a unique location along the vena cava relative to the first ostium. The proximal coupler assembly is fluidly coupled to each of the first and second ports such that the material may be delivered from outside of the patient through the proximal coupler assembly, through both of the first and second ports at the first and second respective delivery positions, and into the first and second renal veins, respectively. A second occlusion member is adjustable between a first configuration and a second configuration as follows. The second occlusion member in the first configuration is adapted to be delivered to a second occlusion position located toward the second ostium from the second delivery position, such that the second port and second occlusion members are located at the second delivery and second occlusion positions, respectively. The second occlusion member in the second configuration at the second occlusion position is adapted to substantially occlude flow from the renal vein and into the vena cava. In addition, the control system is further adapted to control cooperative operation of the second renal delivery assembly and the second occlusion member between third and fourth modes of operation as follows. In the third mode the second occlusion member is in the first configuration at the second occlusion position and venous blood is allowed to flow from the kidney and along the second renal vein and into the vena cava. In the second mode the second occlusion member is in the second configuration at the second occlusion position, venous blood is substantially occluded from flowing from the kidney along the renal vein and into the vena cava, and a volume of fluid agent flows through the second port at the second delivery position and into the second renal vein with retrograde flow into the respective kidney coupled to the second renal vein.

In a further embodiment of this mode, the first and third modes of operation are at least in part simultaneous, and the second and fourth modes of operation are at least in part simultaneous.

Additional aspects of the invention include various methods for treating a renal system in a patient as follows.

One method aspect includes: positioning a first port of a first renal delivery member at a first delivery position within a first renal artery via a first corresponding renal ostium located at a first location along an abdominal aorta wall of an abdominal aorta in a patient, and also positioning a second port of a second renal delivery member at a second delivery position within a second renal artery via a second corresponding renal ostium located at a second location along the abdominal aorta wall that is different than the first location. This method also includes positioning a proximal coupler assembly externally of the patient when the first and second ports are positioned at the first and second delivery positions, respectively. Also included is the step of delivering a material from outside the patient's body via the proximal coupler assembly, through the first and second ports at the first and second delivery positions, respectively, and into the first and second renal arteries, also respectively.

Another method aspect includes: delivering a distal port of a renal delivery member to a delivery position within a renal artery via a corresponding renal ostium along an abdominal aorta wall, positioning a proximal coupler assembly externally of the patient when the distal port is positioned at the delivery position, delivering an anchor in a first configuration to an anchoring position along one of the abdominal aorta or the renal artery within the patient, and adjusting the anchor at the anchoring position from the first configuration to a second configuration that secures the renal delivery member with the distal port substantially retained at the delivery position within the renal artery. In addition, this method also includes allowing substantial blood flow across the anchoring position when the anchor is in the second configuration at the anchoring position, and delivering material from outside the patient's body via the proximal coupler assembly, through the distal port at the delivery position and into the renal artery.

Another method aspect of the invention includes: positioning a distal port of a tubular body of a vascular access system within a vessel having transvascular access to a location along an abdominal aorta associated with first and second renal ostia when a proximal port of the tubular body is located externally of the patient. Another step is introducing first and second renal delivery members of a bi-lateral local renal deliver assembly into the vessel through the tubular body. Another step is introducing a percutaneous translumenal interventional device into the vessel through the tubular body. A further step includes delivering first and second ports of the first and second renal delivery members, respectively, to first and second respective delivery positions within first and second renal arteries, respectively, via the first and second renal ostia, also respectively. Another step is delivering a distal end portion of the percutaneous translumenal interventional device to an intervention location across the location while the first and second ports are located at the first and second delivery positions, respectively. An additional step includes simultaneously delivering material from an external location relative to the patient and directly into each of first and second renal arteries via the first and second ports at the first and second delivery positions, respectively. Accordingly, the bi-lateral renal delivery assembly and a proximal end portion of the percutaneous translumenal interventional device are simultaneously engaged within the tubular body of the vascular access assembly when the first and second ports are at the first and second delivery positions and the distal end portion of the percutaneous translumenal interventional device is at the intervention location.

Another method aspect according to the invention includes a method for preparing a bi-lateral renal delivery system for use in treating a patient as follows. This method includes: introducing first and second renal delivery members of a bi-lateral local renal delivery assembly into a tubular body of a vascular access system, and introducing a percutaneous translumenal interventional device into the tubular body.

In a further mode of this aspect, the various components used in these method steps are further characterized as follows. The bi-lateral renal delivery assembly and the percutaneous translumenal interventional device are simultaneously engaged within the tubular body of the vascular access assembly. The first and second renal delivery members have first and second ports, respectively, that are adapted to be delivered to first and second respective delivery positions within first and second renal arteries, respectively, via first and second renal ostia, also respectively, having unique locations along the abdominal aortic wall. The percutaneous translumenal interventional device has a distal end portion that is adapted to be delivered to an intervention location across a location along the abdominal aorta associated with the first and second renal ostia while the first and second ports are located at the first and second delivery positions, respectively. The first and second renal delivery members are coupled to a proximal coupler assembly that is adapted to deliver material from an external location relative to the patient and to the first and second ports so as to deliver the material directly into each of first and second renal arteries via the first and second ports at the first and second delivery positions, respectively. In addition, the tubular body of the vascular access system has a distal port that is adapted to be positioned within a vessel having transvascular access to the location along the abdominal aorta when a proximal port of the tubular body is located externally of the patient.

Another method aspect of the invention is a method for treating a renal system in a patient via a renal vein as follows. This method includes: delivering a distal port of a renal delivery member to a delivery position within a renal vein via its ostium along a vena cava in a patient, and positioning a proximal coupler assembly externally of the patient when the distal port is at the delivery position. The method also includes fluidly coupling the proximal coupler assembly to the distal port such that a material may be delivered from outside of the patient through the proximal coupler assembly, through the distal port at the delivery position, and into the renal vein. Another step is delivering an occlusion member in a first configuration to an occlusion position located toward ostium from the delivery position, such that the distal port and occlusion members are located at the delivery and occlusion positions, respectively. A further step includes adjusting the occlusion member at the occlusion position from the first configuration to a second configuration so as to substantially occlude flow from the renal vein and into the vena cava. In addition, this method also includes controlling co-operative operation of the renal delivery assembly and the occlusion member between first and second modes of operation as follows. In the first mode the occlusion member is in the first configuration at the occlusion position and venous blood is allowed to flow from the kidney and along the renal vein and into the vena cava. In the second mode the occlusion member is in the second configuration at the occlusion position, venous blood is substantially occluded from flowing from the kidney along the renal vein and into the vena cava, and a volume of fluid agent flows through the distal port at the delivery position and into the renal vein at sufficient pressure to provide retrograde flow into the respective kidney coupled to the renal vein.

Another method aspect of the invention includes flow directing a local renal delivery member from a location within an abdominal aorta and into a renal artery via its renal ostium along the aorta wall. In one further mode, two renal delivery members are flow directed into each of two separate renal ostia, such that bi-lateral local renal delivery may be performed.

Another method aspect of the invention includes cannulating a plurality of x branch lumens from a main lumen or body space by delivering y delivery members to the main lumen or body space that are adapted to be positioned at y unique locations along the main lumen or body space, such that x ones of the y delivery members are located to correspond with the x branch lumens so as to cannulate those branch lumens, wherein x and y are integers and y is greater than x.

It is to be further appreciated that the various foregoing aspects, modes, embodiments, and variations, etc. providing bi-lateral renal delivery, though highly beneficial, are also illustrative of additional broader aspects which are such systems or methods that are adapted to cannulate and deliver therapy directly into bi-lateral branch lumens extending from other main lumens or body spaces from a location externally of a patient.

Another aspect of the invention is a method for treating a renal system in a patient that includes: positioning an introducer sheath within an abdominal aorta at a location associated with first and second renal artery ostia associated with first and second renal arteries that perfuse first and second kidneys in the patient, and delivering a bi-lateral renal delivery assembly in a first configuration under radial confinement through the introducer sheath and to a first position along the location. This method further includes withdrawing the introducer with respect to the bi-lateral renal delivery assembly so as to remove the radial confinement. After removing the bilateral renal delivery assembly from radial confinement, the method further includes allowing first and second bifurcating delivery members to self-expand apart from each other and radially against an abdominal aorta wall at the location with shape memory recovery force to a second configuration.

A further mode of this aspect includes modifying the position of the self-expanded renal delivery assembly so as to self-cannulate at least one of the delivery members into at least one of the renal arteries via its corresponding ostium along the abdominal aorta wall. In one particular further embodiment, the method further includes torquing the renal delivery assembly in the second configuration. In another embodiment, the method further includes modifying the longitudinal position of the renal delivery assembly in the second configuration.

Another aspect of the invention is a method for providing local therapy to a renal system in a patient that includes the following steps. A bi-lateral local renal delivery assembly is delivered to a location within an abdominal aorta corresponding with first and second renal ostium along an abdominal aorta wall of the patient. A percutaneous translumenal interventional device is delivered to an intervention location across the location corresponding with the renal ostia. A first delivery member of the bilateral local renal delivery assembly is positioned in a first renal artery via a first ostium along the abdominal aorta wall, whereas a second delivery member of the bilateral local renal delivery assembly is positioned within a second renal artery via a second ostium along the abdominal aorta wall. The bi-lateral local renal delivery assembly and percutaneous translumenal interventional device are inserted into the patient's vasculature through a common vascular access site.

A further mode of this aspect includes injecting radiocontrast dye into the patient at the intervention location with the percutaneous translumenal device.

Another aspect of the invention is a system for providing local renal therapy in a patient that includes an introducer sheath with a proximal end portion and a distal end portion that is adapted to be positioned at a location within an abdominal aorta associated with first and second renal ostia of first and second renal arteries, respectively, while the proximal end portion extends externally from the patient, and also with an introducer lumen extending between a proximal port located along the proximal end portion and a distal port located along the distal end portion. This system further includes a local injection assembly with an injection port assembly that is adapted to be delivered to the location through the introducer lumen and through the distal port in a first condition. The local injection assembly is adapted to be adjusted at the location from the first condition to a second condition that is advanced externally through the distal port at the location. In the second condition at the location the local injection assembly is adapted to be fluidly coupled to a source of fluid agent located externally from the patient. In the second condition at the location the local injection assembly is also adapted to position the injection port assembly so as to inject a volume of fluid agent substantially bilaterally into each of the two renal arteries. Further included in this system is a sensing mechanism that is adapted to sense a position of at least one of the injection port assembly or the distal port relative to at least one of the renal ostia without use of fluoroscopic or X-ray imaging.

According to one mode of this aspect, at least one marker is provided at a location that is adapted to indicate the location of at least one of the injection port assembly or the distal port with respect to a non-fluoroscopic sensor assembly located externally of the location.

In another mode, a marker assembly is located along the distal end portion of the introducer sheath and is adapted to indicate the relative location of the distal port within the location relative to at least one renal ostium.

In another mode, the local injection assembly includes first and second injection ports that are adapted to be delivered to first and second positions such that the volume of fluid agent is injected substantially into the first and second renal arteries via the first and second injection ports, respectively, at the first and second positions, also respectively. First and second markers are positioned relative to the first and second injection ports, respectively, so as to indicate the relative position of the injection ports relative to the first and second positions, also respectively.

In one beneficial embodiment of this mode, the local injection assembly includes first and second injection members, and the first and second injection ports are located along the first and second injection members, respectively. The first and second markers are located at first and second locations along the first and second injection members relative to the first and second injection ports.

In another mode, a sensor assembly is provided that is adapted to cooperate with at least one of the local injection assembly or the distal port of the introducer sheath such that the sensor assembly is adapted to be positioned within the location and to sense a parameter indicative of the relative position of the local injection assembly or distal port relative to the renal ostia at the location.

In one embodiment of this mode, a sensor is located along the distal end portion of the introducer sheath and is adapted to sense a parameter that is indicative of a relative location of the distal port relative to at least one renal ostium.

In another embodiment, at least one sensor is located relative to the injection port assembly so as to indicate the relative position of the injection port assembly.

According to one highly beneficial variation of this embodiment, the local injection assembly includes first and second injection ports that are adapted to be delivered to first and second positions such that the volume of fluid agent is injected substantially into the first and second renal arteries via the first and second injection ports, respectively, at the first and second positions, also respectively. First and second sensors are positioned relative to the first and second injection ports, respectively, so as to indicate the relative position of the injection ports relative to the first and second positions, also respectively. In still a further beneficial feature that may be incorporated according to this mode, the local injection assembly includes first and second injection members, and the first and second injection ports are located along the first and second injection members, respectively. Further to this feature, the first and second sensors are located at first and second locations along the first and second injection members relative to the first and second injection ports.

According to still further modes incorporating sensor assemblies, such may include an ultrasound sensor, a Doppler ultrasound sensor, an optical sensor, a pressure sensor, a flow velocity sensor, a flow rate sensor, or a chemical sensor, or combinations thereof.

Of further benefit, a monitoring assembly may also be provided for monitoring the sensed parameters externally of the patient.

Another aspect of the invention is a method for providing local renal therapy in a patient that includes in one regard delivering a distal end portion of an introducer sheath to a location within an abdominal aorta associated with first and second renal ostia of first and second renal arteries, respectively, while a proximal end portion of the introducer sheath extends externally from the patient, and also such that an introducer lumen within the introducer sheath extends between a proximal port located along the proximal end portion and a distal port located along the distal end portion at the location. A local injection assembly with an injection port assembly is delivered to the location through the introducer lumen and through the distal port in a first condition. The local injection assembly is adjusted at the location from the first condition to a second condition that is advanced externally through the distal port at the location. The local injection assembly in the second condition at the location is fluidly coupled to a source of fluid agent located externally from the patient. The injection port assembly is positioned so as to inject a volume of fluid agent from the source substantially bilaterally into each of the two renal arteries. In addition, a parameter indicative of a position of at least one of the injection port assembly or the distal port relative to at least one of the renal ostia is sensed without use of fluoroscopic or X-ray imaging.

According to further modes of this method, non-fluoroscopic positioning sensing the position may be accomplished an ultrasound sensor, a Doppler ultrasound sensor, by sensing an optical parameter with an optical sensor, by sensing a pressure parameter with a pressure sensor, by sensing a velocity of blood flow with a flow velocity sensor, by sensing a blood flow rate with a flow rate sensor, or by sensing a chemical parameter of blood with a chemical sensor, or by use of a combination of these modalities.

It is also to be appreciated that each of the foregoing aspects, modes, embodiments, variations, features, or variants on such features is to be considered independently beneficial without necessarily requiring combination with other such components or steps unless expressly stated so. Notwithstanding the foregoing, it is also further appreciated that the various combinations and sub-combinations of such components or steps as would be apparent to one of ordinary skill in the art are further considered independently beneficial and within the intended scope hereof.

Further aspects of the invention will be brought out in the following portions of the specification and accompanying claims below, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 1 illustrates the distal section of a fluid agent delivery catheter with a preformed shape to anchor in an artery according to the present invention.

FIG. 2A illustrates a method of deploying a preformed shaped catheter introduced in a sheath.

FIG. 2B illustrates the intermediate retraction of the sheath shown in FIG. 2A.

FIG. 2C illustrates further retraction of the sheath shown in FIG. 2A.

FIG. 3 illustrates a fluid delivery catheter extending into a branch artery with a high flexibility deflectable section.

FIG. 4A illustrates a method of inserting a catheter with a deflectable section as shown in FIG. 3 using a stylet.

FIG. 4B illustrates a method of deploying a catheter with a deflectable section as shown in FIG. 3 using a stylet FIG. 5 illustrates another embodiment of a fluid delivery catheter with a preformed anchoring shape.

FIG. 6A illustrates a first step for deploying a preformed shape catheter as shown in FIG. 5 with a stylet.

FIG. 6B illustrates another step for deploying a preformed shape catheter as shown in FIG. 5 with a stylet.

FIG. 6C illustrates a further step for deploying a preformed shape catheter as shown in FIG. 5 with a stylet.

FIG. 6D illustrates a preformed shape catheter, deployed with a stylet, in an anchoring shape as shown in FIG. 5.

FIG. 7A illustrates a multilumen catheter using a flexible reinforcing element as an anchoring device.

FIG. 7B illustrates distal motion of the reinforcing element forming an expanded loop.

FIG. 8A illustrates another embodiment of the catheter shown in FIG. 7A where the reinforcing element loops around the catheter in a helical configuration.

FIG. 8B illustrates the loop formed in FIG. 8A when the reinforcing element is extended.

FIG. 8C illustrates a section view of the catheter shown in FIG. 8B symmetrically anchored to the wall of an artery.

FIG. 11A illustrates an anchoring catheter with a reinforcing element to anchor near the distal end.

FIG. 11B illustrates the anchoring catheter shown in FIG. 11A with the reinforcing element deployed.

FIG. 12A illustrates a method of constructing an anchoring catheter to form loops that provide an anchoring force as shown previously in FIG. 10.

FIG. 12B illustrates the anchoring catheter in FIG. 12A with loops deployed to bow outward.

FIG. 13A illustrates another anchoring catheter using two loops of shape retaining material.

FIG. 13B illustrates the anchoring catheter shown in FIG. 13A restricted in a sheath.

FIG. 13C illustrates the anchoring catheter shown in FIG. 13A deployed in a blood vessel.

FIG. 14A illustrates a side view of multilumen catheter with an asymmetrical, inflatable anchoring member according to the present invention.

FIG. 14B is a cross sectional view of the catheter in FIG. 14A with the inflatable anchoring member folded in a sheath.

FIG. 14C is a cross sectional view of the catheter in FIG. 14A deployed in a blood vessel.

FIG. 15A illustrates a multilumen catheter with a multi-lobed, symmetrical, inflatable anchoring member.

FIG. 15B is a cross sectional view of the catheter in FIG. 15A with the inflatable anchoring member folded in a sheath.

FIG. 15C is a cross sectional view of the catheter in FIG. 15A deployed in a blood vessel.

FIG. 18A illustrates a bifurcated renal catheter with distal anchoring sections manipulated by control wires.

FIG. 18B illustrates a cross sectional view of the catheter shown in 18A taken along the lines 18B-18B.

FIG. 19 illustrates a preformed bifurcated catheter with distal sections having opposite preformed 90-degree loop shapes for anchoring.

FIG. 20 illustrates a variation of a preformed bifurcated catheter where one distal section is similar to that shown in FIG. 17 and the second distal section similar to that shown in FIG. 10.

FIG. 21 illustrates the cross section of bifurcated catheter as shown in FIG. 20 taken along the lines 21-21.

FIG. 22D illustrates the catheter shown in FIG. 22A inserted in a main artery with hinges flexed in the fully open position.

FIG. 23 illustrates two independent micro catheters each placed directly into a renal artery.

FIG. 48A illustrates a step in constructing a multiple distal extension catheter according to the present invention.

FIG. 48B illustrates another step in constructing a multiple distal extension catheter.

FIG. 48C illustrates a further step in constructing a multiple distal extension catheter.

FIG. 48F illustrates another step in constructing a multiple distal extension catheter.

FIG. 48G illustrates a further step in constructing a multiple distal extension catheter.

FIG. 49 is an illustration of a drain catheter system for use in the venous system according to the present invention.

FIG. 50 is a detailed view of the distal tip of the drain catheter system shown in FIG. 49 and deployed in a renal vein.

FIG. 54 illustrates a proximal coupler system for delivering aortic devices adjunctively with a catheter.

FIG. 55 illustrates a cross-sectional view of the proximal coupler system as shown in FIG. 54.

DETAILED DESCRIPTION OF THE INVENTION

As will be appreciated by reference to the detailed description below and in further respect to the Figures, the present invention is principally related to selective bi-lateral renal delivery systems and methods. Accordingly, the present invention is thus related to, and the present description is to be read in combination with, various aspects of the subject matter disclosed in the following prior filed, co-pending U.S. patent applications that are commonly owned with the present application (to the extent such disclosures are readily considered in conjunction with the present disclosure, as would be apparent to one of ordinary skill): Ser. No. 09/229,390 to Keren et al., filed Jan. 11, 1999; Ser. No. 09/562,493 to Keren et al., filed May 1, 2000; and Ser. No. 09/724,691 to Kesten et al., filed Nov. 28, 2000. The disclosures of these prior patent applications are herein incorporated in their entirety by reference thereto.

The invention is also related to, and the present description should be considered in conjunction with, certain aspects of the subject matter disclosed in the following Published International Patent Applications (to the extent such published disclosures are readily considered in conjunction with the present disclosure as would be apparent to one of ordinary skill): WO 00/41612 to Libra Medical Systems, published Jul. 20, 2000; and WO 01/83016 to Libra Medical Systems, published Nov. 8, 2001. The disclosures of these Published International Patent Applications are also herein incorporated in their entirety by reference thereto.

Figure 59:
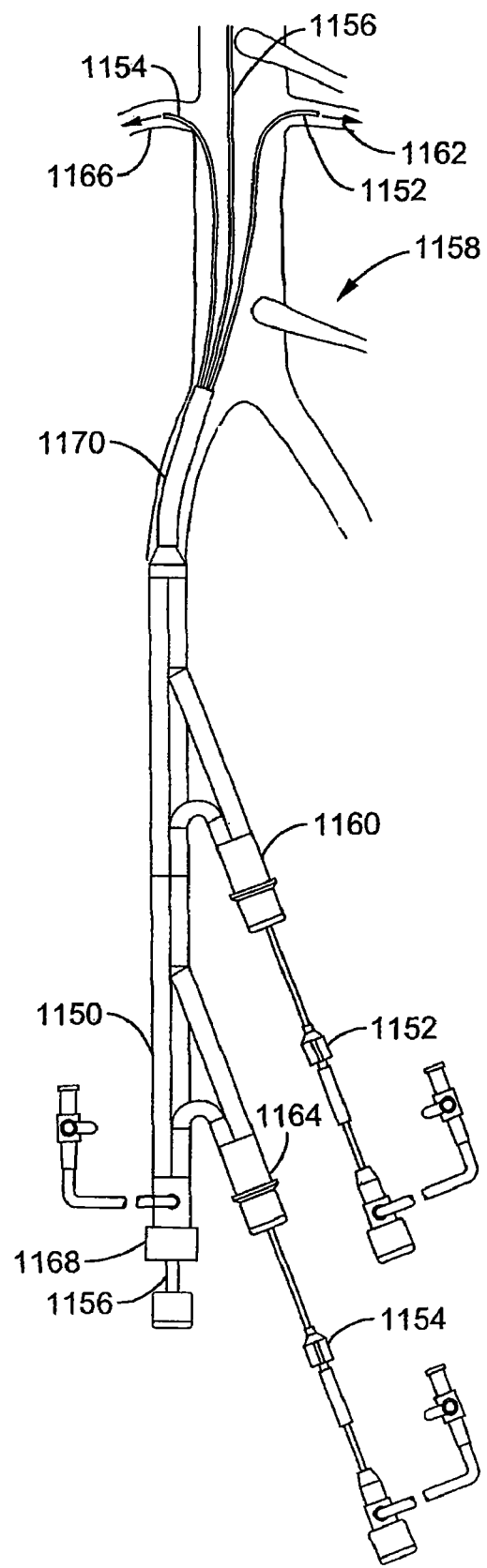
FIG. 59 is a stylized illustration of a double Y assembly with two local fluid delivery systems and an intervention catheter in an aorta system.

Referring more specifically to the drawings, for illustrative purposes the present invention is embodied in the apparatus generally shown in FIG. 1 through FIG. 59. It will be appreciated that the apparatus may vary as to configuration and as to details of the parts, and that the method may vary as to the specific steps and sequence, without departing from the basic concepts as disclosed herein.

The description herein provided relates to medical material delivery systems and methods in the context of their relationship in use within a patient's anatomy. Accordingly, for the purpose of providing a clear understanding, the term proximal should be understood to mean locations on a system or device relatively closer to the operator during use, and the term distal should be understood to mean locations relatively further away from the operator during use of a system or device. These present embodiments below therefore generally relate to local renal drug delivery generally from within the renal arteries themselves; however, it is contemplated that these systems and methods may be suitably modified for use in other anatomical regions and for other medical conditions without departing from the broad scope of various of the aspects illustrated by the embodiments.

In general, the disclosed material delivery systems will include a fluid delivery assembly, a proximal coupler assembly and one or more elongated bodies, such as catheters. These elongated bodies may contain one or more delivery lumens and generally consist of a proximal region, a mid-distal region, and a distal tip region or regions in the case of multi-tipped embodiments. The distal tip region will typically have means for anchoring and means for delivering a material such as a fluid agent. Radiopaque markers or other devices may be coupled to the specific regions of the elongated body to assist introduction and positioning.

The material delivery system is intended to be placed into position by a physician, typically either an interventionalist (cardiologist or radiologist) or an intensivist, a physician who specializes in the treatment of intensive-care patients. The physician will gain access to a femoral artery in the patient's groin, typically using a Seldinger technique of percutaneous vessel access or other conventional method.

Turning now to FIG. 1, an embodiment of the distal section of an anchoring material delivery catheter 10 with a preformed shape to anchor in an artery 12 to prevent movement during medical procedures is generally shown. Material delivery catheters may move during medical procedures due to blood flow, body movement and movement of interventional catheters. It is highly beneficial that the distal portion of a catheter remain stationary within the branch blood vessel and deliver therapeutic agent throughout the procedure. The proximal shaft will play a significant role in the maintenance of catheter position within the patient anatomy. The mechanical characteristics of the proximal shaft region will influence the magnitude of the "anchoring" forces required on the wall of the main or branch artery by the apparatus discussed below. Therefore, the proximal shaft section of the catheter will require greater stiffness and column strength to withstand the forces imparted on the catheter by blood flow in the main vessel and possible patient repositioning or movement that can occur throughout the course of treatment. The pre-formed shape in this embodiment comprises a near distal section 14 with a memory shape defined by R1 and an adjacent second section 16 with memory shape defined by radius R2. Radius R1 and radius R2 are biased in the opposite direction so catheter 10 forms a generally S shape and exerts opposite spring forces in the direction of arrows 18 against the walls of artery 12 when section 14 and section 16 are in their natural state.

In one exemplary embodiment, the wall of the proximal shaft region includes a stainless-steel braid, coil or multiple independent longitudinal wire inclusions to increase column strength and flexural rigidity. The proximal shaft region is preferably constructed of a higher durometer polymeric material such as 60D to 70D polyurethane or a poly-ether-block-amide copolymer such as PEBAX.

FIG. 2A through FIG. 2C illustrates sequential steps in a method of deploying a pre-formed catheter 10 introduced in a radially confining sheath 22. Distal end 25 of the catheter 10 is released from sheath 22 by moving sheath 22 proximally as shown by directional arrow 24 or alternatively by advancing catheter 10 distally through the sheath as shown by directional arrow 26. FIG. 2B illustrates the position of the pre-formed catheter 10 with section 14, formed with memory shape defined radius R1, exposed from sheath 22. FIG. 2C illustrates the position of the pre-formed catheter 10 with second section 16 formed with radius R2 exposed.

FIG. 3 through FIG. 4B illustrate an anchoring material delivery catheter 30 extending through a main artery 32 and into a branch artery 3 with a shapeable section 36 deployed to form an S configuration defined by radius R1 and radius R2. Radius R1 is formed when shapeable section 36 is deformed by a guide wire (shown in FIG. 4A and FIG. 4B) or other deployment means. Radius R2 is formed by the contact of the distal end 38 on the wall of branch artery 34. The "S" shape of catheter 30 exerts anchoring force 40 proximal of the deflectable section 36 and anchoring force 42 distal of the shapeable section 36.

FIG. 4A and FIG. 4B illustrate a method of anchoring catheter 30 with a shapeable section 36. Pull wire 44 is attached to an inner lumen wall of shapeable section 36 at approximately median position 46 and extends to a control point at the proximal end of catheter 30 (not shown). When pull wire 44 is retracted, proximal segment 48 of shapeable section 36 takes a shape defined by radius R1 as shown in FIG. 4B. Distal section 50 of shapeable section 36 takes a shape defined by radius R2 (shown in FIG. 3) by contact of distal end 38 of catheter to the artery wall 34. Control over anchor force 40 and anchor force 42 exerted on artery wall 34 (shown in FIG. 3) may be achieved by monitoring the tensile force exerted on pull wire 44.

Referring now to FIG. 5 through FIG. 6D, another embodiment of an anchoring material delivery catheter 52 with an anchoring memory shape is generally shown. In FIG. 5, catheter 52 is deployed in artery 12 where section 54 is configured with radius R1, section 56 is configured with radius R2 oriented opposite from R1, section 58 with radius R3 oriented towards R2 and section 60 with radius R4 oriented opposite from R3. The orientation of radii R1 through R4 create an anchor shape that exerts outward anchoring forces 62 and 64 and anchors catheter 52 in artery 12 when sections 54, 56, 58 and 60 assume their natural memory shape.

FIG. 6A through FIG. 6D illustrate a method of anchoring a pre-formed shaped material delivery member 52 as shown in FIG. 5. Stiff mandrel 66 is inserted in catheter 52 to position memory shaped sections 54, 56, 58, and 60 in a straightened configuration. In FIG. 6B, stiff mandrel 66 has been retracted proximally as shown by arrow 68 to allow section 54 to assume a memory shape defined by radius R1. Note that radius R1 may vary during deployment as the catheter 52 is positioned. In FIG. 6C, stiff mandrel 66 has been retracted proximally past section 58 and section 56 assumes memory shape defined by radius R2 and section 58 assumes memory shape with radius R4 In FIG. 6D stiff mandrel 66 has been retracted proximally past section 60 with radius R4 and delivery member 52 assumes an anchoring shape as illustrated in FIG. 5.

Figure 7C:
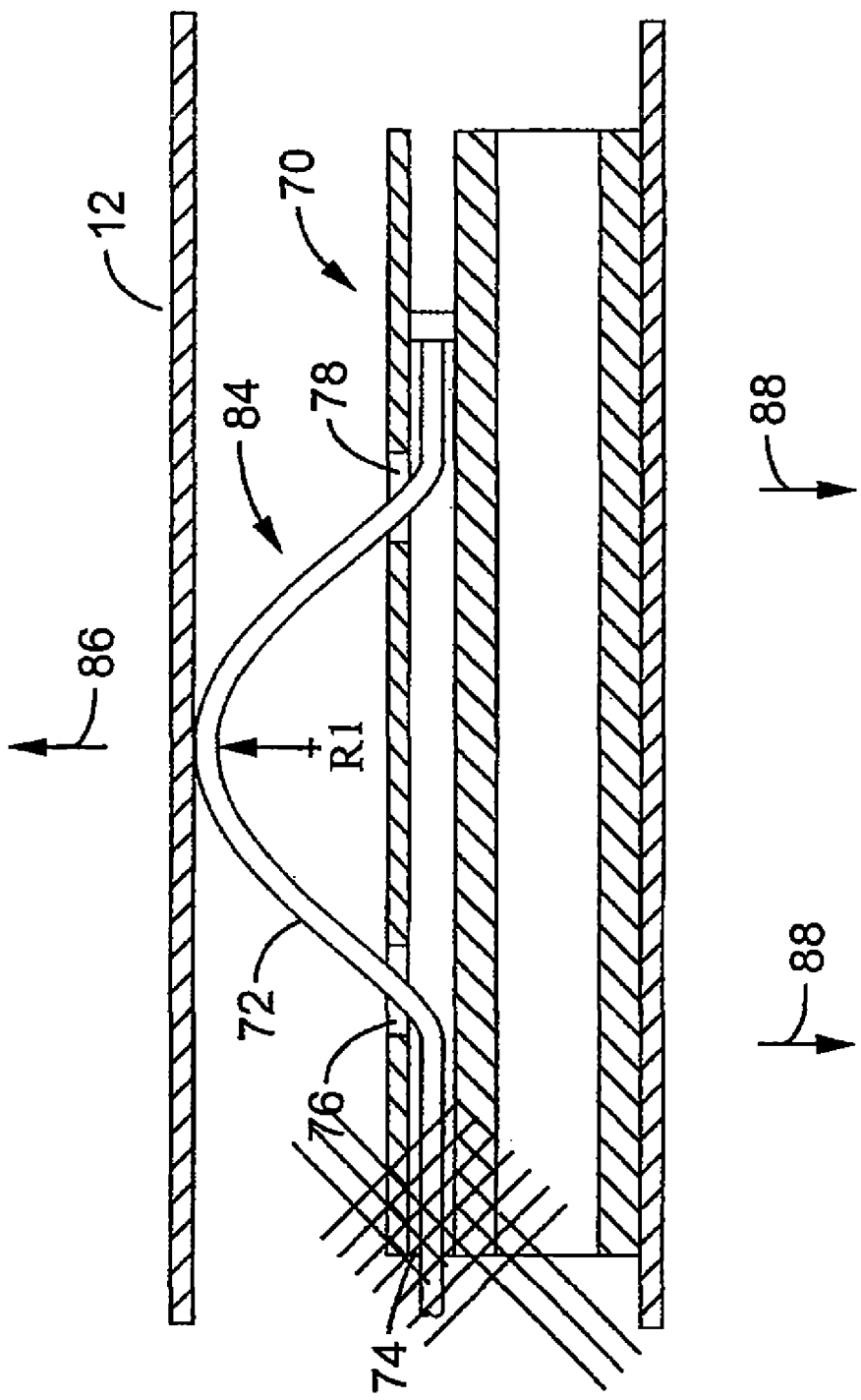
FIG. 7C illustrates a cross-sectional view of the catheter shown in FIG. 7B inserted in a body vessel.

FIG. 7A through FIG. 7C illustrate another embodiment of an anchoring multilumen delivery catheter 70 with a flexible reinforcing element 72 located in reinforcing element lumen 74 according to the present invention. In FIG. 7A, reinforcing element 72 exits the reinforcing element lumen 74 through first opening 76 and reenters the reinforcing element lumen 74 proximal of first opening 76 at second opening 78. Reinforcing element 72 is anchored in reinforcing element lumen 74 distal of second opening 78 at position 80.

FIG. 7B illustrates distal motion 82 of reinforcing element 72 in reinforcing element lumen 74 causing reinforcing element 72 to form an expanded loop 84 defined by radius R1 outside of catheter 70 and between first opening 76 and second opening 78.

FIG. 7C illustrates a section view of delivery member 70 shown in FIG. 7B asymmetrically anchored to a wall of artery 12 by force 86 exerted by expanded loop 84 and by force 88 exerted by the body of catheter 70.

FIG. 8A and FIG. 8B illustrate another embodiment of an anchoring multilumen delivery member 70 where reinforcing element 72 exits first opening 76 and loops around delivery member 70 in a helical configuration before entering second opening 78.

FIG. 8B illustrates the delivery member 70 in FIG. 8A with loop 90 formed around catheter 70 when reinforcing element 72 is pushed in direction 82.

FIG. 8C illustrates a sectional view of delivery member 70 shown in FIG. 8B symmetrically anchored to a wall of artery 12 by forces in the direction of arrow 92 that are exerted on the inner wall circumference artery 12 by expanded loop 90.

Figure 9:
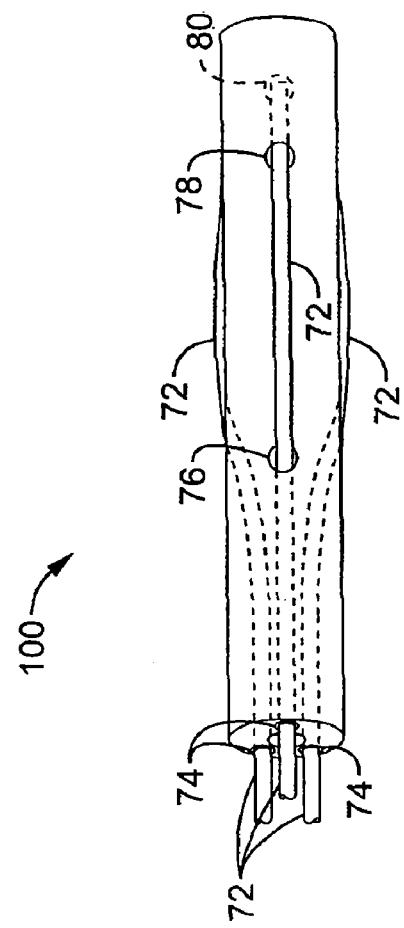
FIG. 9 is another embodiment of the device shown in FIG. 7A with two or more reinforcing elements for anchors.

FIG. 9 Is another embodiment of an anchoring delivery catheter shown in FIG. 7A with two or more reinforcing elements 72 in a multilumen catheter 100 with a first opening 76 and corresponding second opening 78 for each reinforcing element 72. Three reinforcing elements 72 are illustrated in FIG. 9 with phantom lines of the reinforcing element lumens 74 omitted for clarity.

Figure 10:
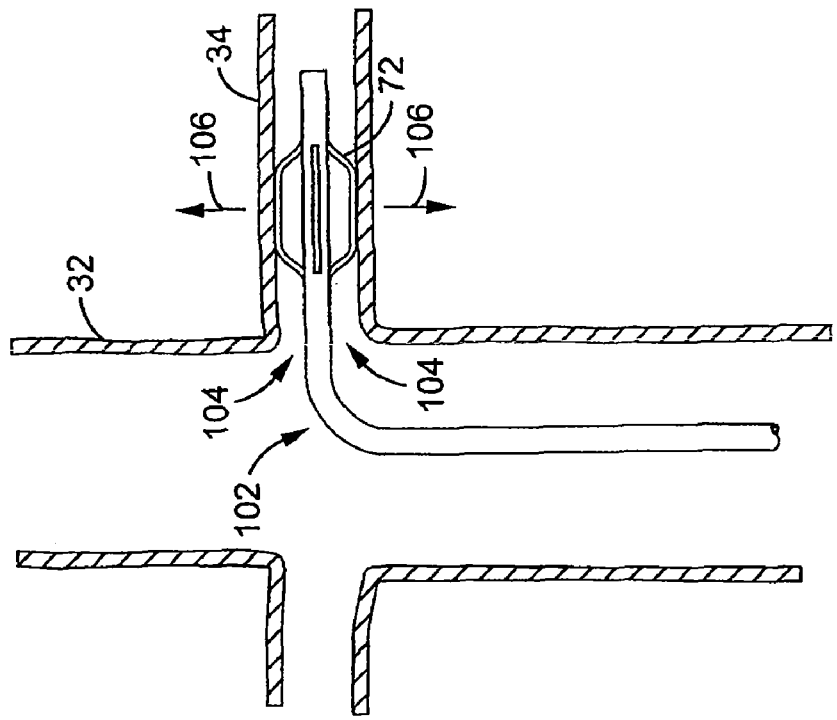
FIG. 10 illustrates a multilumen catheter shown in FIG. 9 with four reinforcing elements, inserted and anchored in a branch artery.

FIG. 10 illustrates a multilumen catheter 102, similar to catheter 100 in FIG. 9, with four reinforcing elements 72 inserted and anchored in a branch artery 34 of a main artery 32. When reinforcing elements 72 are extended, they bow outward into loops 104 which exert an anchoring force 106 against the inner wall of branch artery 34.

FIG. 11A and FIG. 11B illustrate an embodiment of an anchoring delivery catheter where reinforcing strut 110 is anchored near the distal end 112 of a catheter 114 and is attached to the distal end 116 of sheath 118 which encloses the catheter 114 proximal of distal end 112. In FIG. 11B, sheath 118 is advanced as shown by arrow 120 or alternatively, catheter 114 is retracted as shown by arrow 122. Reinforcing strut 110 bows outward as loop 124 which anchors the catheter 114 in similar to the anchor previously shown in FIG. 7C.

FIG. 12A and FIG. 12B illustrate a cut section view of an anchoring delivery catheter where catheter 130 is encased in flexible sheath 132 and anchored to sheath 132 at the distal end 134 near the distal end of catheter 130. Slits 136 are made in pairs lengthwise near the distal end of sheath 132 to form two or more struts 138. A pair of struts 138 is depicted in the embodiment shown in FIG. 12A and FIG. 12B. In FIG. 12B, sheath 132 is advanced in a distal direction shown by arrow 140 or alternatively, or in combination, catheter 130 is retracted in a proximal direction as shown by arrow 142. Sheath struts 138 bow outward to form loops 144 which anchor catheter 130 against a vessel wall as shown previously in FIG. 10.

FIG. 13A through FIG. 13C illustrates an anchoring delivery catheter where two or more loops 150 of shape retaining material, such as nickel titanium wire, are attached near the distal end of catheter 152 so the coupling 154 of metal loops are proximal of the apex 156 of loops 150. Loops 150 are configured to bias the apex 156 away from the surface of catheter 152 when loops 150 are in their free state.

FIG. 13B illustrates catheter 152 shown in FIG. 13A with loops 150 attached that are encased in a radially confining sheath 158, such as an introducer sheath, which compresses the apex 156 of loops 150 near the surface of catheter 152 within sheath 158.

FIG. 13C illustrates catheter 152 shown in FIG. 13A inserted in artery 12 with sheath 158 retracted in the proximal direction shown by arrow 160. Loops 150 flex outwardly and loop apex 156 exerts outward anchoring force 162 against the inner wall of artery 12. When medical procedures are complete, sheath 158 is advanced over catheter 152 to collapse loops 150 to permit the removal of catheter 152.

FIG. 14A through FIG. 14C illustrates the distal section of another embodiment of an anchoring multilumen catheter 164 according to the present invention. Catheter 164 has an inflation lumen 166 fluidly connected to asymmetrical inflatable member 168, with an oblong lobe shape, shown in an inflated state.

FIG. 14B illustrates a cross section of catheter 164 encased in sheath 170 with asymmetrical inflatable member 168 in a deflated state and folded around catheter 164.

FIG. 14C illustrates a cross section of catheter 164 inserted in artery 12 with asymmetrical inflatable member 168 in an inflated state and exerting anchoring force 172 and anchoring force 174 against the inner wall of artery 12. The cross section of asymmetrical inflatable member 168 is a lobe shape to contact inner wall of artery 12 in one location when inflated and simultaneously allow free area 178 for blood flow in artery 12.

FIG. 15A through FIG. 15C illustrate another embodiment of an anchoring multilumen catheter 164 with inflation lumen 166 fluidly connected to a symmetrical inflatable member 180 generally comprising two or more symmetrically positioned lobes 182. In the embodiment illustrated in FIG. 15A, inflatable member 180 has 4 symmetrical lobes 182.

FIG. 15B illustrates a cross section of catheter 164 encased in a radial confinement sheath 170 with lobes 182 of symmetrical inflatable member 168 in a deflated state and folded around catheter 164.

FIG. 15C illustrates a cross section of catheter 164 inserted in artery 12 with radial confinement sheath 170 shown in FIG. 15B removed and symmetrical inflatable member 180 in an inflated state and exerting force 184 at the contact point of each lobe 182 against the inner wall of artery 12. The cross section of lobes 182 is shaped so each lobe 182 contacts inner wall of artery 12 when inflated and allow free area 186 for blood flow in artery 12. Each inflated lobe 182 exerts radial outward anchoring force 184.

Figure 16:
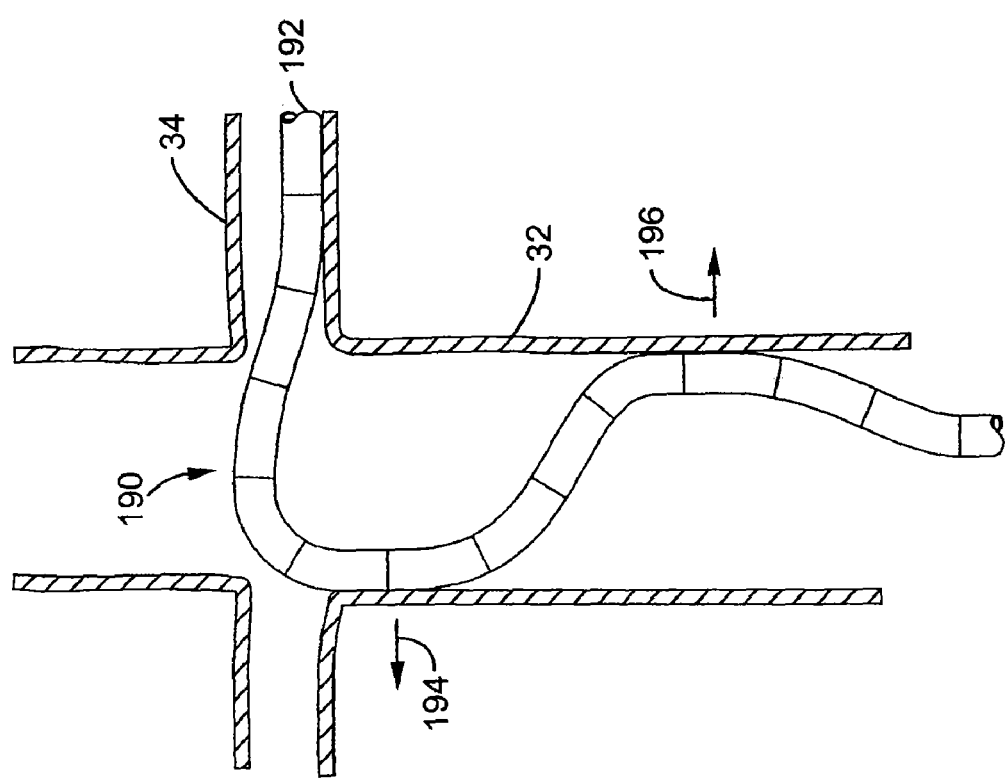
FIG. 16 illustrates the distal section of an anchoring renal catheter with a preformed compound shape.

FIG. 16 illustrates a distal section of an anchoring delivery catheter 190 of similar construction to one shown in FIG. 1 with a distal end 192. Radii R1 through R5 define a compound "S" anchoring shape, wherein R1 is generally configured to position distal end 192 of catheter 190 in artery 34 and against a wall of artery 34. Radii R2 and R3 are generally configured in an opposite direction of R1 and create a biased section that exerts outward force 194 against a wall of aorta 32. Radii R4 and R5 are generally configured opposite of radii R1 and R2 and create an adjacent section to exert an outward force 196 against a generally opposite wall of aorta 32. The specific configuration of radii R1 through R5 creates an anchoring shape that is generally larger than aorta 32 in its natural state.

Figure 17:
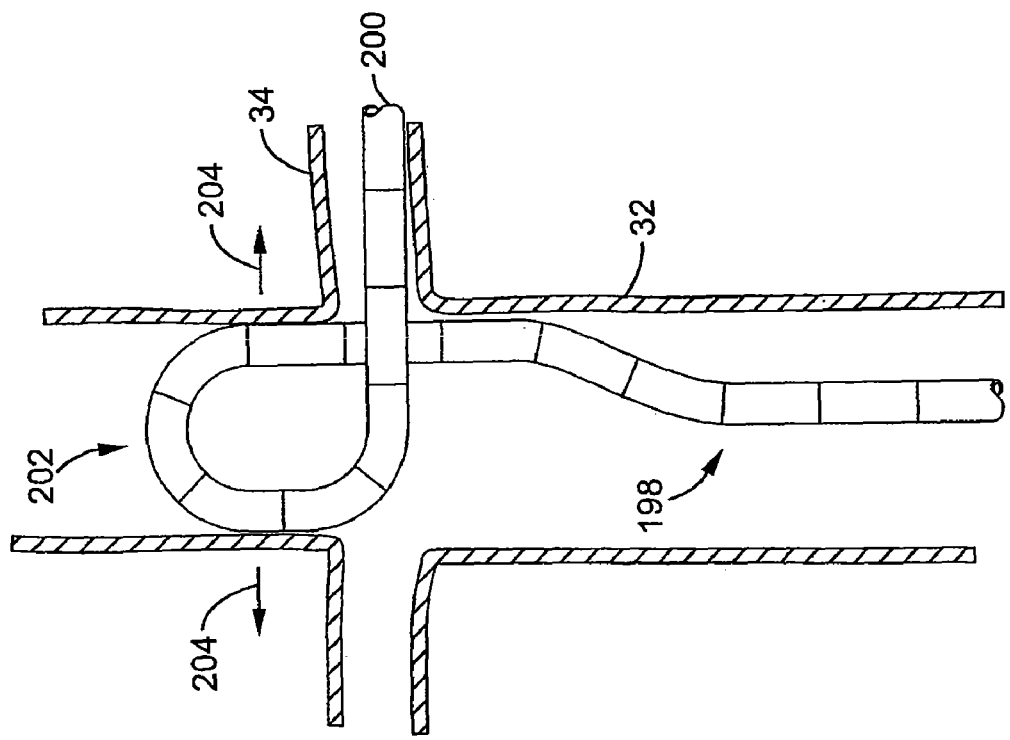
FIG. 17 illustrates another embodiment of the renal catheter shown in FIG. 16 where the compound shape comprises a 270-degree loop.

FIG. 17 illustrates another anchoring catheter 198 with a distal end 200 similar to that shown in FIG. 16, wherein a compound shape 202 is defined by radii R1 and R2, wherein R1 and R2 are generally configured to form a 270-degree loop. The natural diameter of the loop of compound shape 202 is generally larger than the diameter of aorta 32 and exerts anchoring forces 204 against opposite walls of aorta 32. Radii R3 and R4, proximal of compound shape 202 on catheter 198, are generally configured opposite each other to facilitate optimum positioning of compound shape 202 and distal end 200 of catheter 198 in artery 34.

FIG. 18A and FIG. 18B illustrate a bifurcated anchoring catheter 208 in main artery 32 with a delivery sheath 210, a left distal section 212 and right distal section 214 adapted to deliver a material. Distal sections 212, 214 are configured to preferentially select arteries 34 when delivery sheath 210 is retracted proximally. Distal section 212 is manipulated by control wire 216 and distal section 214 is independently manipulated by control wire 218, wherein distal sections 212, 214 are manipulated as previously described in FIG. 3 to anchor in arteries 34. FIG. 18B illustrates a cross section of bifurcated catheter 208 taken along the lines 18B-18B in FIG. 18A with multilumen delivery sheath 210 enclosing distal sections 212, 214 with control wires 216, 218. Each distal section 212, 214 is capable of independent insertion and manipulation in a branch artery 34. Cross section of delivery sheath 210 may also be a single lumen or more than two lumens.

FIG. 19 illustrates an embodiment of a preformed bifurcated delivery catheter 220 with distal section 222 having a preformed 90-degree loop shape 226 and distal section 224 having the same but opposing 90-degree loop shape 226. The diameter of preformed loop shape 226 of distal section 222, 224 is generally larger than the diameter of main artery 32 and thereby exerts an anchor force outward on main artery 32 as previously described in FIG. 17. Distal section 222 and distal section 224 are configured to preferentially insert into opposing branch arteries 34.

FIG. 20 illustrates a variation of a bifurcated anchoring delivery catheter 228 wherein distal section 230, similar to catheter 198 previously described in FIG. 17, is combined with a distal section 232, similar to catheter 102 previously described in FIG. 10. The diameter of the 270-degree loop shape 234 on distal section 230 is generally larger than the diameter of main artery 32 and anchors catheter 228 in main artery 32 with distal section 230 in branch artery 34. Distal section 232 is anchored in a branch artery 34 and with reinforcing element loops 236.

FIG. 21 is a cross section taken along the lines 21—21 in FIG. 20 of a bifurcated catheter 228 with lumen 238 fluidly connected to distal section 230. Lumen 240 contains distal section 232 with a plurality of lumens 242 for reinforcing elements 236 and a delivery lumen 244.

Figure 22C:
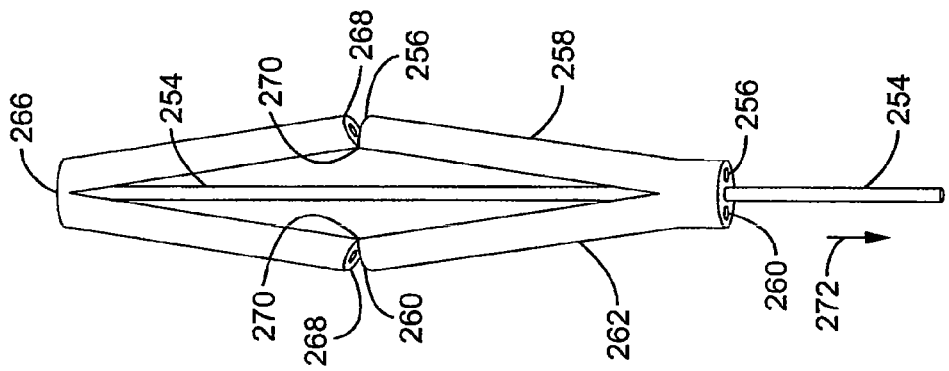
FIG. 22C illustrates a perforating crosscut forming hinges of the catheter shown in FIG. 22A with the hinges in the partly open position.
Figure 22B:
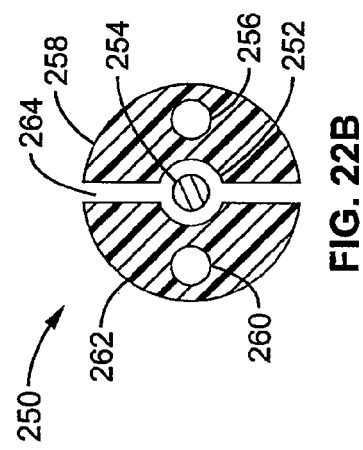
FIG. 22B illustrates a cross section view of FIG. 22A taken along the lines 22B-22B.
Figure 22A:
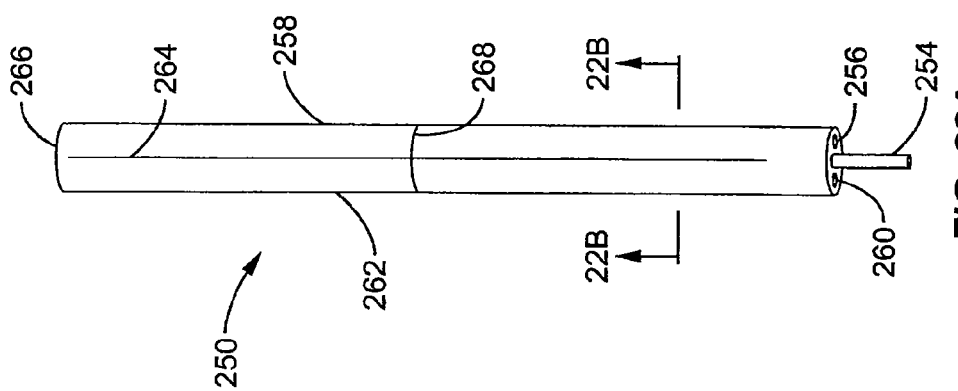
FIG. 22A illustrates a plan view of a multilumen catheter with a longitudinal slit near the distal end.

FIG. 22A illustrates a plan view and FIG. 22B illustrates a cross section view taken along the lines 22B—22B in FIG. 22A. A multilumen catheter 250 with a center lumen 252 with control wire 254 and delivery lumen 256 in the right side 258 of catheter 250 and delivery lumen 260 in the left side 262 of catheter 250 are shown. A longitudinal slit 264 of a predetermined length is made in catheter 250 near the distal end 266 to separate right side 258 from left side 262. Slit 264 terminates a predetermined distance from distal end 266. Control wire 254 is anchored (not shown) at distal end 266. A perforating crosscut 268, medial of slit 264 is made part way into right side 258 through lumen 256 and part way into left side 262 through lumen 260.

FIG. 22C illustrates that the perforating cross-cut 268 does not extend completely through right side 258 and left side 260, thus forming hinges 270 when control wire 254 is retracted in proximal direction 272. Lumen 256 and lumen 260 are bisected at hinges 270.

FIG. 22D illustrates the multilumen catheter 250 shown in FIG. 22A inserted in main artery 32 and positioned adjacent to branch arteries 34. Control wire 254 is retracted, retracting distal end 266 proximally to flex hinges 270 outward placing bisected lumens 256 and 260 into branch arteries 34. Material 272 is delivered through lumen 256 and lumen 260 and into branch arteries 32 at hinges 270.

FIG. 23 illustrates two independent micro catheters 272 introduced through aorta 32 with introducer sheath 274 and each positioned directly into a renal artery 34, by methods previously described, for material delivery. Each micro catheter 272 has a distal tip adaptation 276, such as a small loop, to anchor and prevent backing out during delivery. Each micro catheter may be optionally equipped with a guide wire (not shown) to assist placement in renal artery 34. Several advantages are gained by this embodiment. In one regard, it is a direct cannulation system and technique used to perfuse both sides of the renal system. There is generally no question that once placed, 100% of drug will bilaterally enter the cannulated renal arteries. Moreover, whereas certain improved devices as provided herein generally result in an improved procedure, more conventional tools may be employed in many circumstances, and the most difficult part of procedure (accessing renal arteries) relies on well-accepted techniques and equipment. Still further, according to this embodiment, device surface area is minimized with a reduced potential for clotting.

Figure 24:
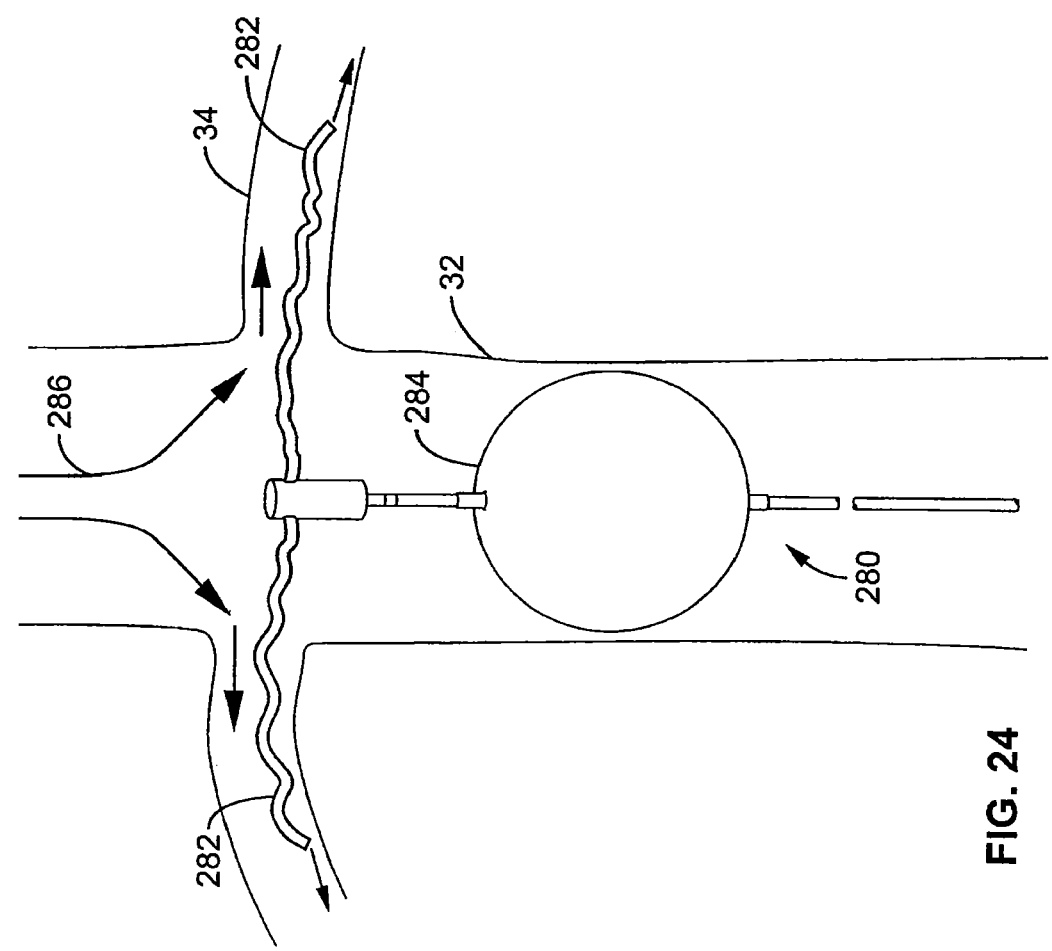
FIG. 24 illustrates a flow-guided catheter with flexible renal sub catheters and an inflatable member in an inflated state.

FIG. 24 illustrates a flow-guided catheter 280 with distal, flexible renal sub-catheters 282 and a mid-distal inflatable member 284 placed in aorta 32 proximal to renal arteries 34. When inflatable member 284 is in an inflated state, aortic blood flow 286 is diverted into renal arteries 34 and sub catheters 282 are flow guided into renal arteries 34.

The principle of operation requires the flow guided catheter 280 to be placed into the region above the renal arteries 34. Inflatable member 284 is inflated and positioned just below the renal arteries 34. When inflatable member 284 is inflated, aortic blood flow is temporarily diverted into the renal arteries, and thus the flow-guided sub-catheters 282 are then advanced through the main catheter. Because all of the aortic blood flow is now directed into the renal arteries 34, the flow will guide the sub-catheters directly into each renal artery. Once these sub-catheters are inserted to an adequate depth, the inflatable member 284 is deflated, returning all aortic blood flow to normal. However, the flow-guided sub-catheters 282 remain within the renal arteries 34, and fluid agent infusion can then be accomplished with 100% being directed to the target organ.

Because the aorta 32 remains fully open during the drug infusion, the standard coronary procedures can occur simultaneously without undue interference from the flow guided catheter 280 and sub-catheters 282. The device is 'forgiving' relative to positioning and placement, and does not require exact positioning to accomplish the drug infusion objective. Because the flow-guided sub-catheters are placed directly into the renal arteries, there are no issues relating to quality of 'seal' as there is no requirement for a seal and the fluid agent is unlikely to leak into the aorta as the infusion system is so deeply seated into the renal arteries. There is no ongoing occlusion or even diversion of the aortic flow.

Figure 25:
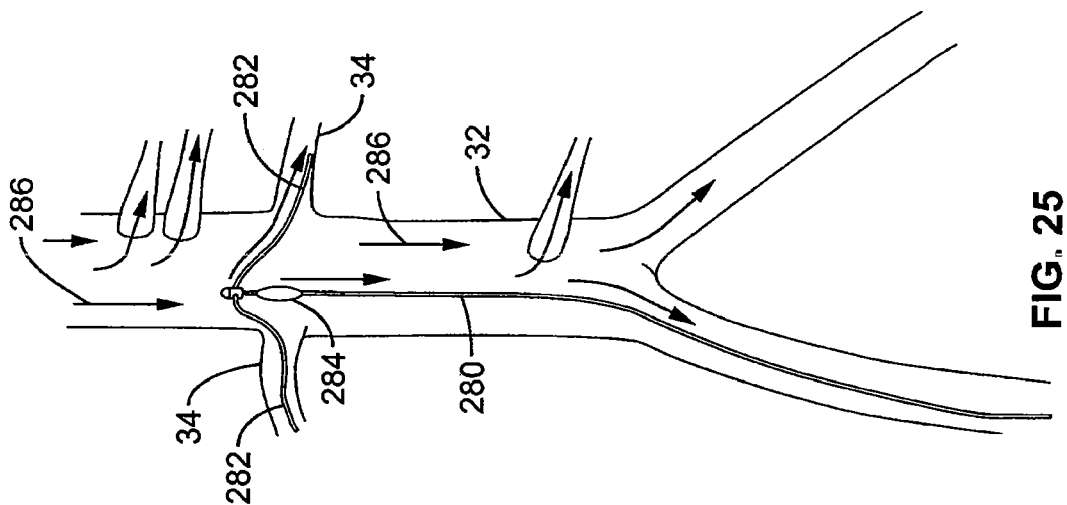
FIG. 25 illustrates the flow-guided catheter shown in FIG. 24 with the inflatable member in a deflated state.

FIG. 25 illustrates the flow-guided catheter 280 previously described in FIG. 24 with inflatable member 284 in a deflated state. Sub-catheters 282 remains in renal arteries 34 while blood flow 286 is normal. Intervention catheters (not shown) may pass guided catheter 280 with inflatable member 284 in a deflated state. Sub-catheters 282 may be equipped with distal tip adaptations for anchoring as previously described.

Figure 26:
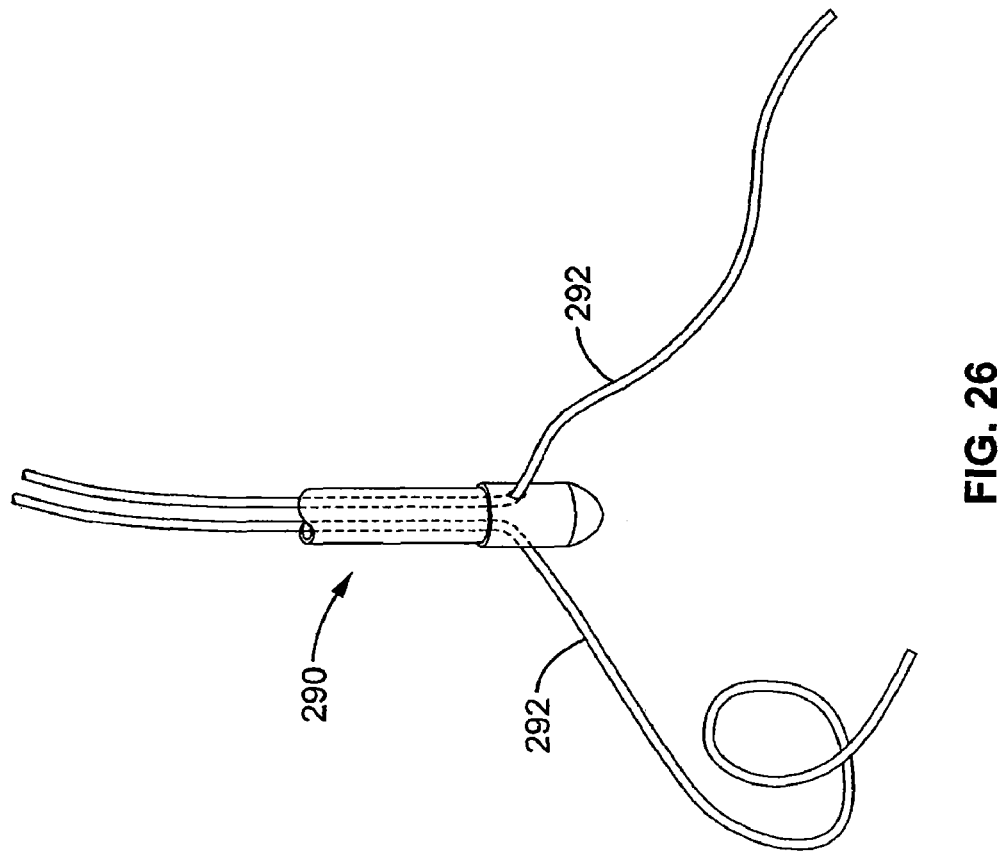
FIG. 26 illustrates a flow-guided catheter for use with a brachial approach from above the renal arteries.

FIG. 26 illustrates an embodiment of a flow-guided catheter 290 adapted for insertion from a brachial approach from above. Because approximately 30% of aortic blood flow enters the renal arteries, catheter 290 can be positioned just above the renal arteries and sub-catheters 292 will naturally flow into the renal arteries for material delivery. This embodiment has other advantages when the access and introduction occurs from the brachial approach, where the flow guided sub-catheters 292 have an even more natural 'flow' into the renal arteries. There is little risk of vessel trauma or other injury, as there are no 'seals' required, and thus any fitment issues and the associated risks of over sizing are eliminated.

Figure 27:
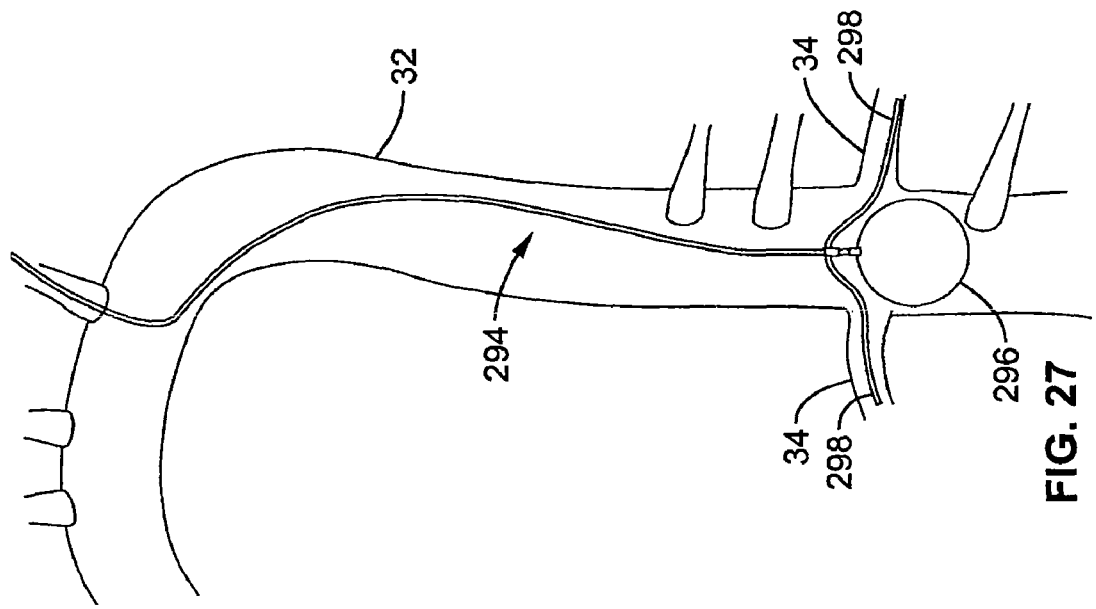
FIG. 27 is a flow-guided catheter for use with a brachial approach from above with an inflatable member.

FIG. 27 is another flow-guided catheter 294 adapted for a brachial approach configured with distal inflatable member 296. Inflatable member 296 is positioned in aorta 32 below renal arteries 34 in an inflated state. Increased blood flow to renal arteries 34 cause sub catheters 298 to flow naturally into renal arteries 34. When inflatable member 296 is in a deflated state, interventional catheters (not shown) can pass renal arteries 34 unobstructed for medical procedures.

Figure 28:
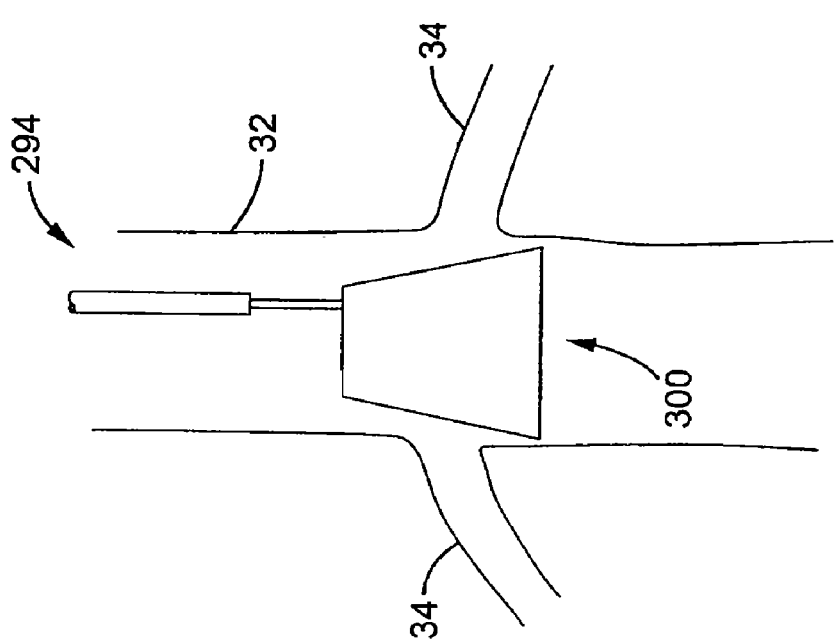
FIG. 28 illustrates a truncated cone flow diverter that may be used adjunctively with flow-guided catheters using a brachial approach.

FIG. 28 illustrates a catheter 294 adapted for a brachial approach and with a truncated cone flow diverter 300 that may be used to temporarily increase blood flow to renal arteries 34 adjunctively with flow guided renal catheters.

Figure 29:
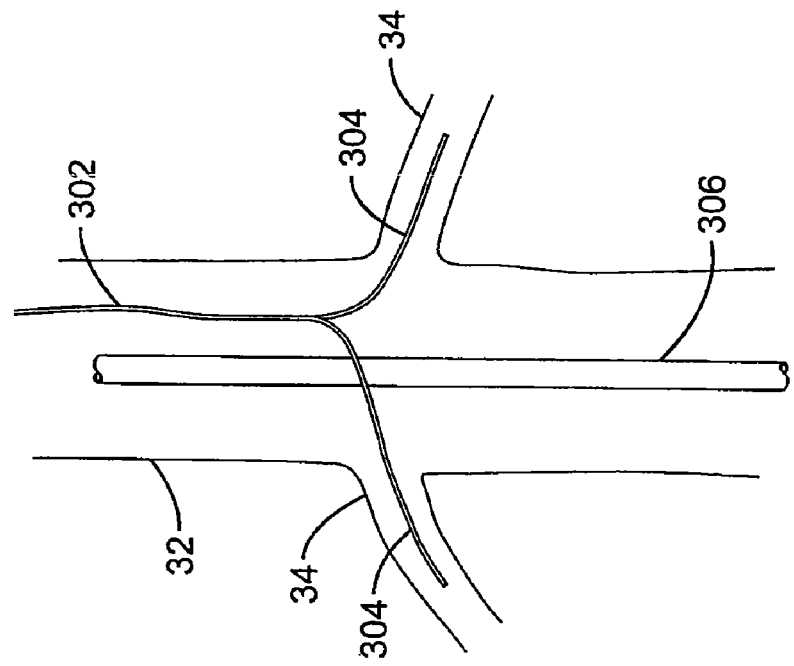
FIG. 29 illustrates a low profile flow-guided catheter using a brachial approach.

FIG. 29 illustrates a low profile flow-guided catheter 302 with distal sub-catheters 304 in renal arteries 34 and adjacent to interventional catheter 306. The position of flow-guided catheter 302 does not interfere with interventional catheter 306.

Figure 30:
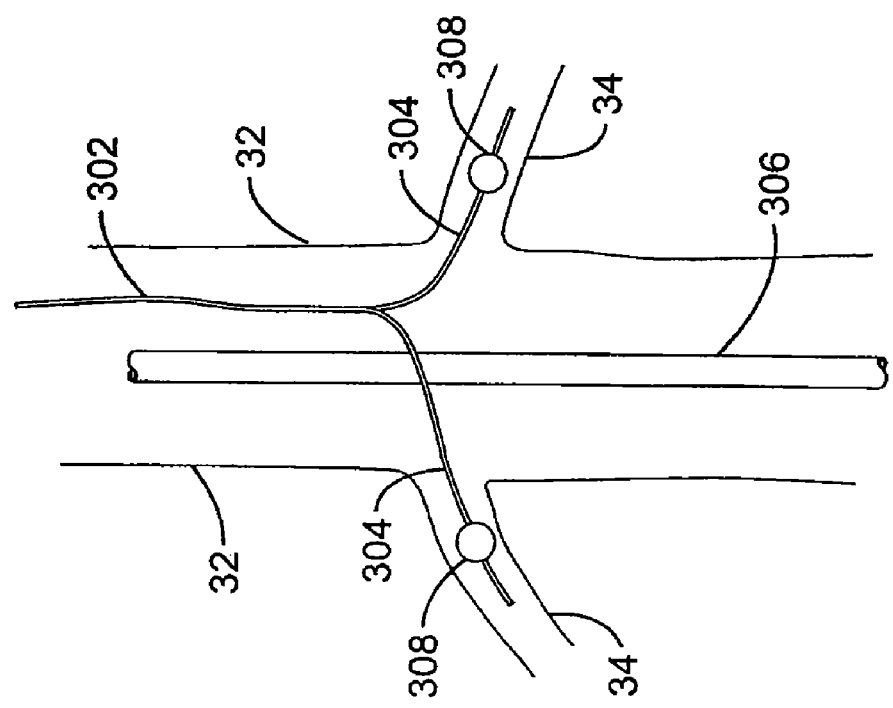
FIG. 30 illustrates the flow-guided catheter shown in FIG. 29 with sub catheters equipped with distal tip inflatable members.

FIG. 30 illustrates a variation of low profile flow-guided catheter 302 shown in FIG. 29 positioned with sub-catheters 304 in renal arteries 34. Sub-catheters 304 are equipped with distal tip inflatable members 308 to assist flow-guided placement and anchoring. Flow-guided catheter 302 does not interfere with interventional catheter 306.

Figure 31:
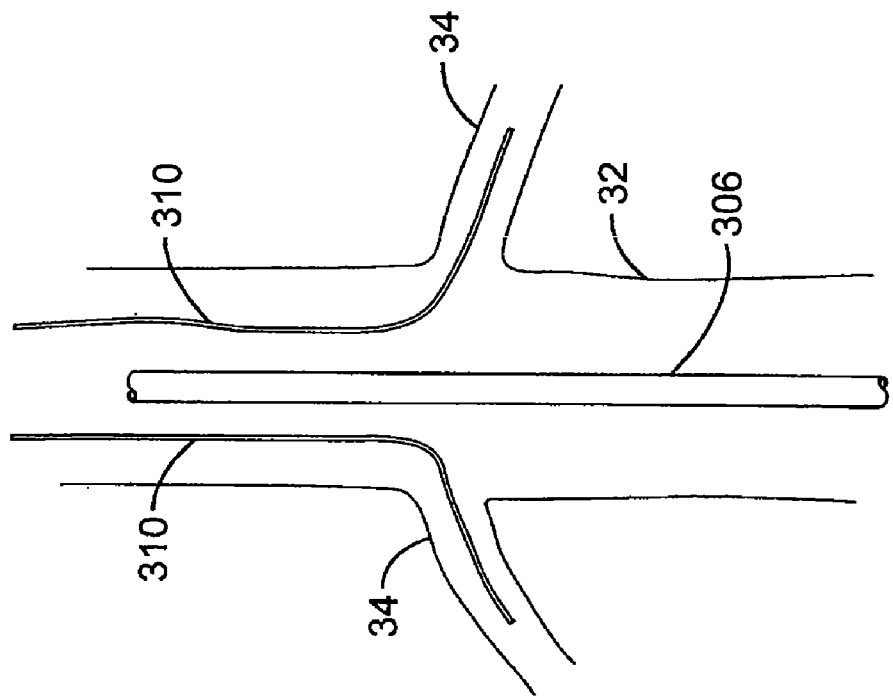
FIG. 31 illustrates independent low profile flow guided sub-catheters using a brachial approach.

FIG. 31 illustrates a brachial approach for independent low profile sub-catheters 310 positioned in renal arteries 34 without interfering with interventional catheter 306.

Figure 32:
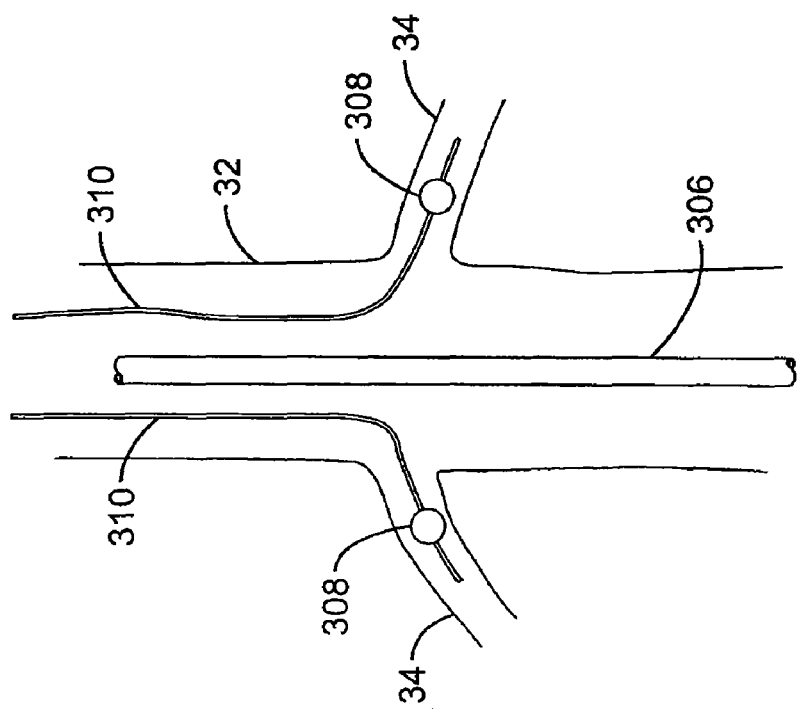
FIG. 32 illustrates the independent sub-catheters shown in FIG. 31 with distal tip inflatable members.

FIG. 32 illustrates a variation of independent low profile sub-catheters 310 shown in FIG. 31 with distal tip inflatable members 308 to assist flow-guided placement and anchoring in renal arteries 34 and positioned without interfering with intervention catheter 306.

Figure 33:
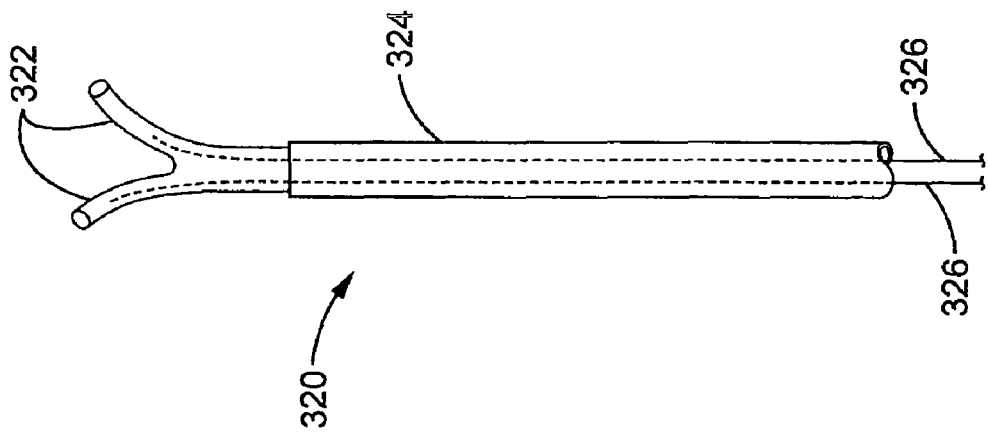
FIG. 33 illustrates the distal end of a bifurcated renal catheter.

FIG. 33 shows the distal section of a bifurcated catheter 320 with the bifurcated distal ends 322 positioned to insert into the renal arteries. Catheter 324 contains one or more lumens (not shown) for guide wire(s) 326 and material delivery. Guide wires 326 manipulate the bifurcated ends 322 from a straight insertion position (not shown) to the material delivery position shown here. In one beneficial embodiment, bifurcated ends 322 can be maintained in a straight position by guide wires 326 to allow advancement and positioning without a radially confining sheath. This embodiment takes advantage of human anatomy, which provides for renal arteries to originate within a few millimeters of each other along the aorta and generally laterally or slightly dorsally. The origins of the renal arteries are also generally set apart from other vessels originating in the same manner, thus making it easy to locate the renal arteries. This allows for a single bifurcated catheter 320 with a bifurcated distal section 322 to be placed with its distal tips into the renal arteries, negating the need for two separate catheters. It also allows for a single device to reach both renal arteries simultaneously and to be adaptable to a majority of patients with a single size, again because of the relative uniformity and consistency of human anatomy in this respect. The use of pull wires in this embodiment provides for a relatively more rigid distal (beyond the bifurcation) catheter, but also allows for active placement via manipulation of the proximal control mechanism. An advantage of the pull wires is that they may be configured so as to make the distal catheter sections straight, allowing for sheathless advancement, and then be manipulated to cause the bifurcated ends 322 to point toward the renal arteries.

Figure 34:
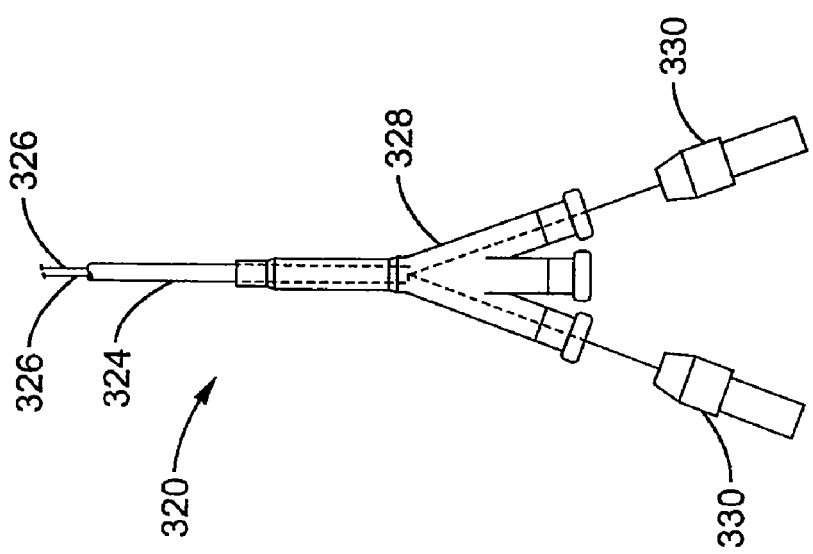
FIG. 34 illustrates the proximal end of the bifurcated catheter shown in FIG. 33 with a hub assembly and controls for pull wires.

FIG. 34 illustrates the proximal end of catheter 320 with guide wires 326 in sheath 324 extending down through a Y hub assembly 328. Guide wires 326 connect to respective handles 330 which are used for manipulation of the bifurcated distal ends 322 shown in FIG. 33. A proximal coupler assembly (not shown) is typically used for delivery of fluid agents through the catheter.

Figure 35:
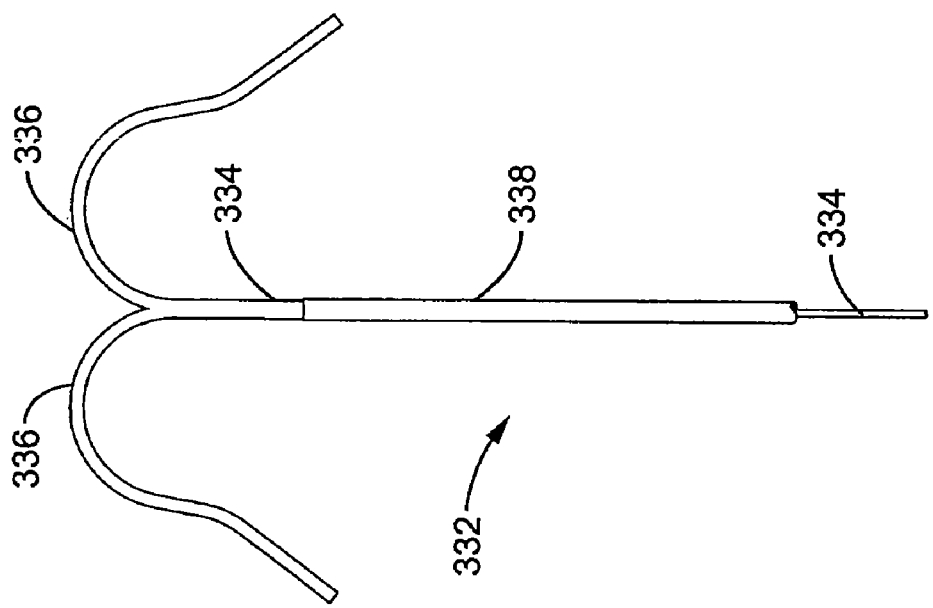
FIG. 35 illustrates the non-supported, pre-formed distal extensions of a bifurcated

FIG. 35 illustrates a bifurcated renal catheter 332 with material delivery catheter 334 and non-supported, pre-formed tubular distal extensions 336. Distal extensions 336 exhibit a variation of a pre-formed shape to enhance cannulation of the renal arteries. In an exemplary embodiment, pre-formed distal extensions are made of a medium durometer Pebax material that will pop into branch arteries and maintain their relative position, but still exhibit a softness that will not cause intimal trauma when the distal tips contact vessel walls. In one embodiment, distal extensions 336 have a plurality of infusion ports (not shown). In another embodiment, the distal extensions 336 have radiopaque marker bands (not shown) to aid in positioning and cannulation of the renal arteries. Proper radiopaque markings, allows for the placement of the distal extensions 334 without the need to use contrast, as the physician would be able to see the extensions "pop" into the renal arteries as it moves down the aorta. In one beneficial embodiment, polymer tube 338 is coupled to bifurcated catheter 332 proximal of distal extensions 334. In one embodiment, polymer tube has radiopaque marker bands (not shown) to assist in positioning and cannulation of the renal arteries.

An introducer sheath (not shown) radially confines the distal extensions 336 during insertion and is retracted after insertion to allow distal extensions 336 to extend to their pre-formed shape. Material delivery catheter 334 may have a single delivery lumen or separate lumens for each distal extension 336.

Figure 35A:
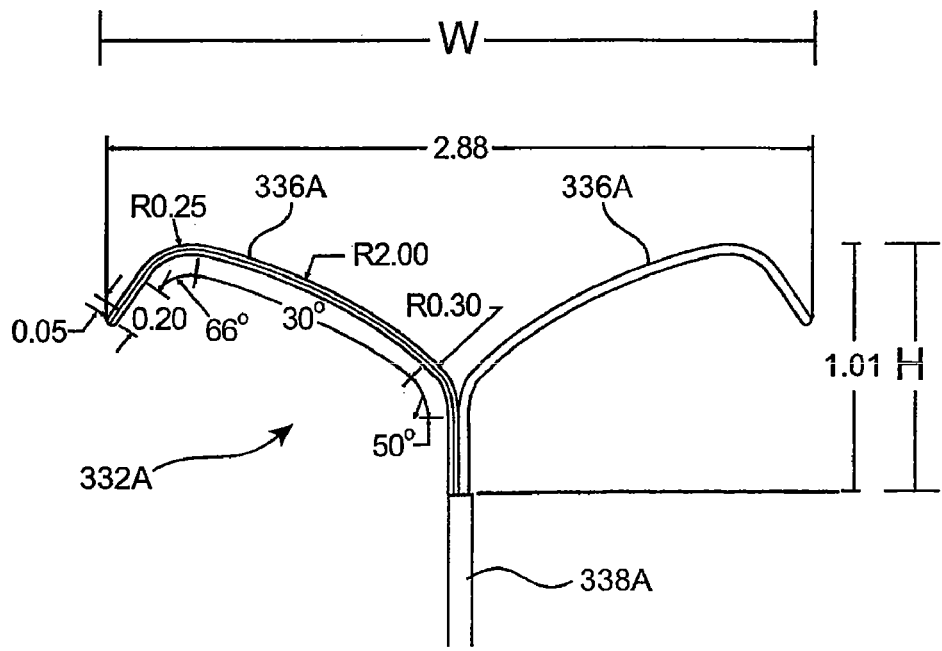
FIG. 35A illustrates the non-supported, pre-formed distal extensions of an alternative embodiment of a bifurcated renal infusion catheter.
Figure 35B:
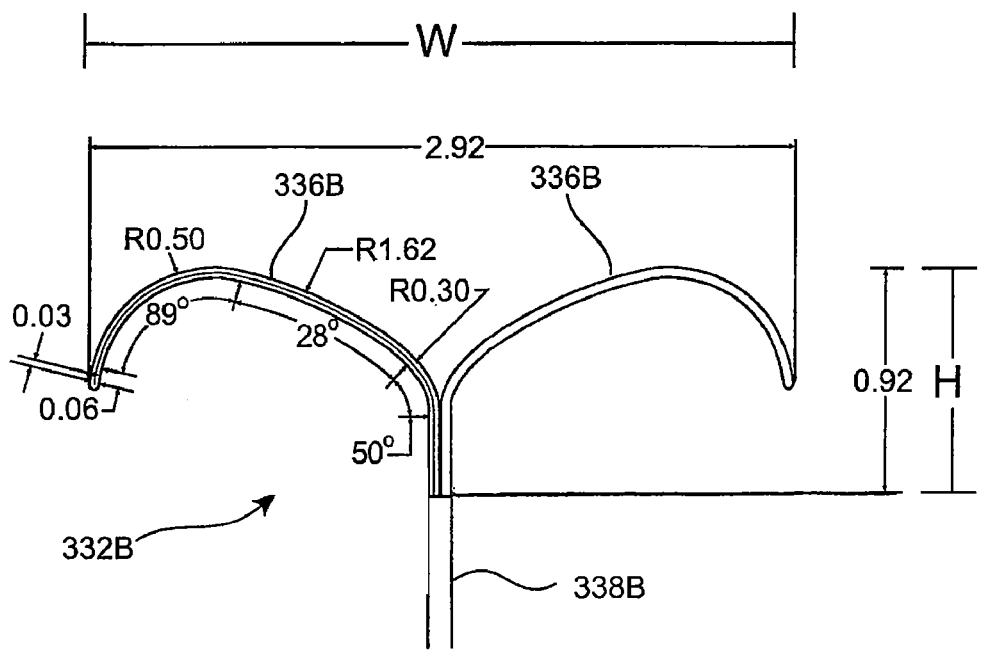
FIG. 35B illustrates the non-supported, pre-formed distal extensions of an alternative embodiment of a bifurcated renal infusion catheter.
Figure 35C:
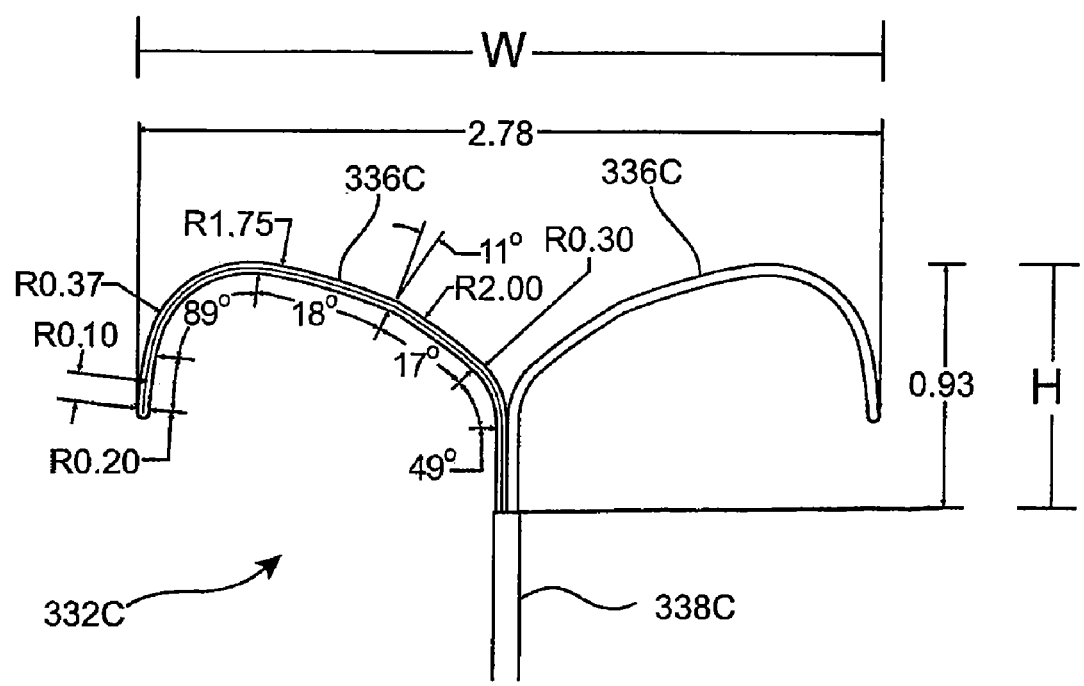
FIG. 35C illustrates the non-supported, pre-formed distal extensions of an alternative embodiment of a bifurcated renal infusion catheter.

FIGS. 35A-35C illustrate three different embodiments of a bifurcated renal catheter 332A, 332B, 332C with material delivery catheter 334 and non-supported, pre-formed tubular distal extensions 336. In each of the three embodiments of catheter 332A, 332B, 332C, distal extensions 336A, 336B, 336C have a different shape, angles of curvature and dimensions than in the other embodiments. Of course, these three embodiments are merely examples, and many other shapes, angles of curvature and dimensions may be used in alternative embodiments. In each of FIGS. 35A-35C, a "height" H may be measured from the distal end of polymer tube 338A, 338B, 338C to the part of distal extensions 336 that is farthest away from the polymer tube 338 distal end. A "wingspan" W may also be measured from a distal tip of one distal extension 336 to a distal tip of the opposite distal extension 336. In some embodiments, for example, the height H may range from about 0.75 inches to about 1.5 inches, and more preferably from about 0.85 inches to about 1.25 inches, and even more preferably from about 0.9 inches to about 1.15 inches. Wingspan W, in some embodiments, may range from about 2.0 inches to about 4.0 inches, and more preferably from about 2.5 inches to about 3.5 inches, and even more preferably from about 2.5 inches to about 3.0 inches. Alternative embodiments may have any of a number of suitable combinations of dimensions. Angles and radii of curvature of distal extensions 336 are also shown in FIGS. 35A-35C, though alternative embodiments may have different curvatures.

Figure 36:
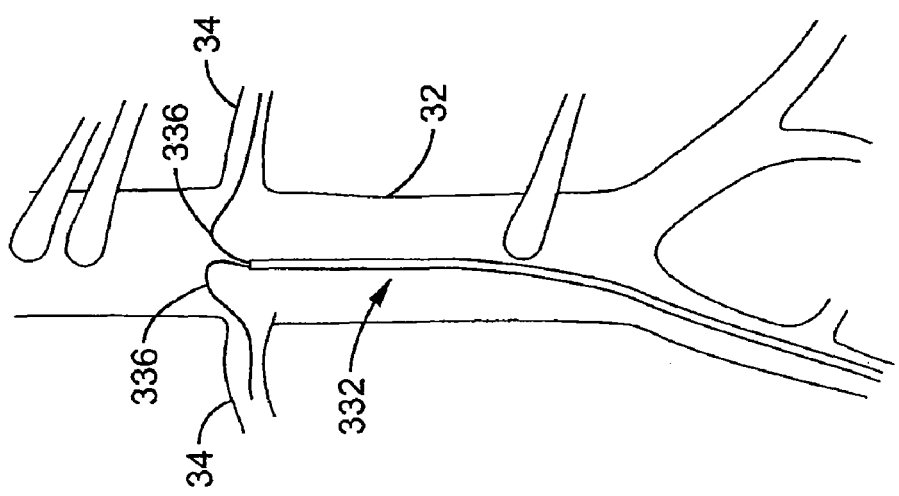
FIG. 36 is a stylized illustration of the bifurcated catheter of FIG. 35 with the distal extensions positioned in the renal arteries.

FIG. 36 illustrates bifurcated catheter 332 shown in FIG. 35 inserted into aorta 32 with the introducer sheath omitted for clarity. Bifurcated catheter 332 is manipulated in aorta 32 in the vicinity of renal arteries 34 until the preformed distal extensions 336 pop into and anchor in the renal arteries 34.

Figure 37:
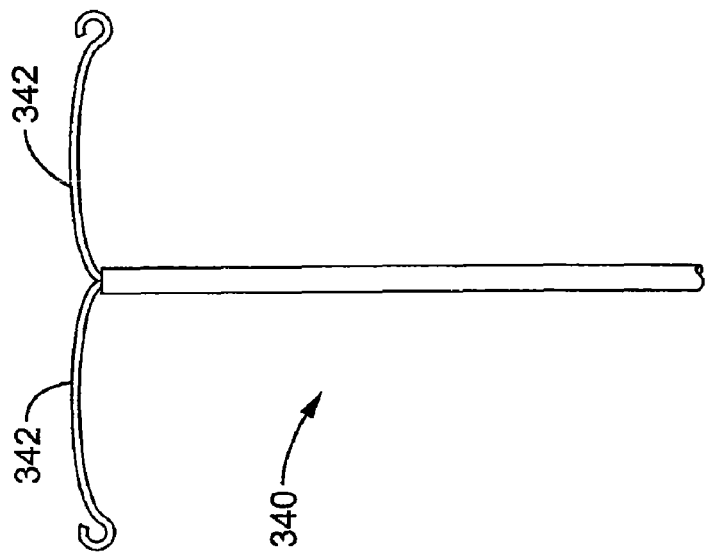
FIG. 37 is another bifurcated renal infusion catheter with pre-formed distal extensions.

FIG. 37 illustrates another embodiment of a bifurcated catheter 340 with preformed distal extensions 342 positioned for insertion into renal arteries. It is to be understood that variations of these preformed shapes for the distal extensions of bifurcated delivery catheters may be chosen for particular renal artery or ostial diameters. It is further understood that some variations of the pre-formed shapes enhance cannulation of branch arteries when moving up the aorta while other variations enhance cannulation moving down the aorta. Still further variations work equally well moving up or down the aorta. Testing has demonstrated the ability to "find" the renal ostia with these embodiments. Variations in the radius of the distal curves on the catheter extensions adapt the device to work particularly well for different shaped (e.g. diameter) renal arteries or ostia, and is generally considered to work in particular beneficial modes when the radius of curvature is smaller than the diameter of the renal arteries. Accordingly, kits may be provided to physicians with varied radii of curvature for the distal extensions and devices chosen to appropriately match the size of the vessel to cannulate.

Figure 38:
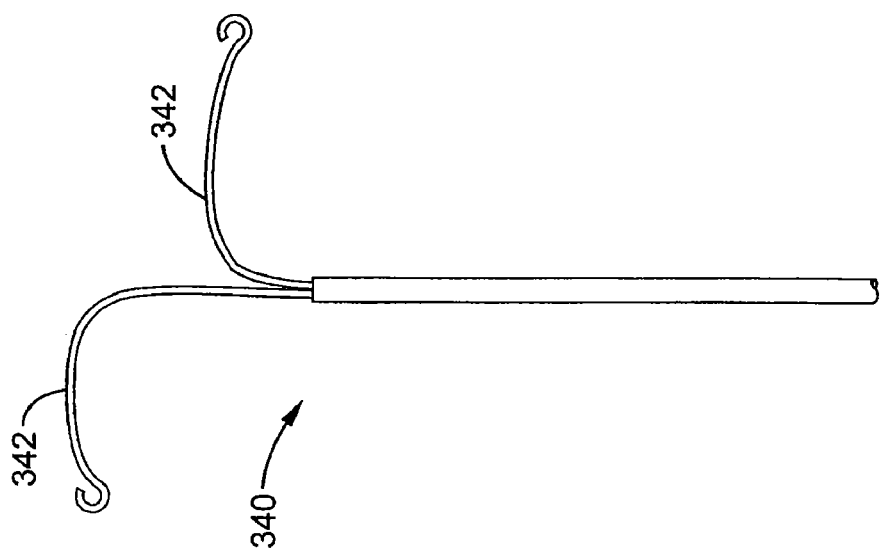
FIG. 38 is the bifurcated catheter as illustrated in FIG. 37 with offset distal extensions.

FIG. 38 is another embodiment of a bifurcated catheter 340 previously illustrated in FIG. 37 with distal extensions 342 offset to provide access to offset renal arteries.

Figure 39:
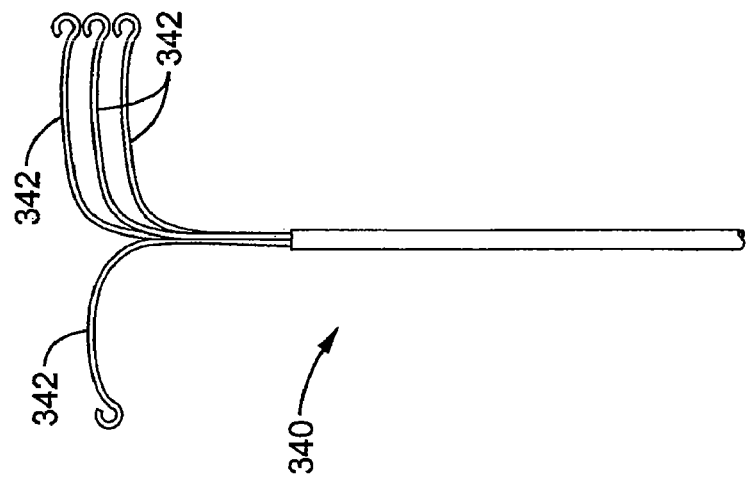
FIG. 39 is another embodiment of a bifurcated catheter as shown in FIG. 37 where a plurality of distal extensions are offset and located on one side.

FIG. 39 is a further alternative embodiment of a bifurcated catheter 340 as shown in FIG. 37 where a plurality of pre-formed distal extensions 342 are configured on one side to accommodate a plurality of renal artery offset conditions (not shown). These distal extensions 347 may incorporate unique radiopaque markings so as to make them individually identifiable under fluoroscopic visualization. This embodiment typically incorporates one or more proximal coupler assemblies (not shown) for properly directing drug infusion to the proper distal extensions (those which are placed into the renal arteries).

Figure 40:
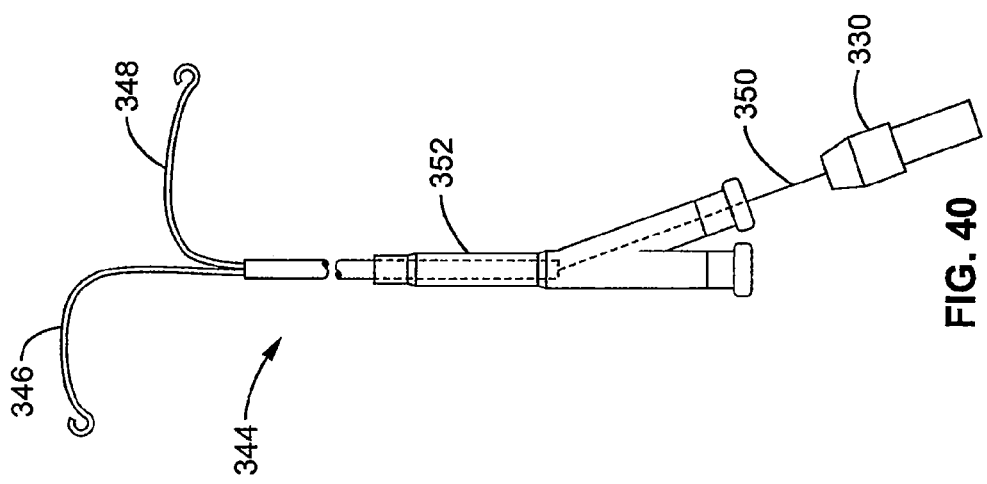
FIG. 40 is a bifurcated catheter with a moveable distal extension controlled by a guide wire.

FIG. 40 illustrates a bifurcated catheter 344 where distal end 346 is passive and distal extension 348 is movable through a guide wire 350 connected through a proximal coupler 352 to a handle 330 as shown previously in FIG. 34. In this embodiment, the "easier" cannulation is done first with the passive extension 346 and the second cannulation accomplished using manipulation of distal extension 348 through control wire 350.

Figure 41:
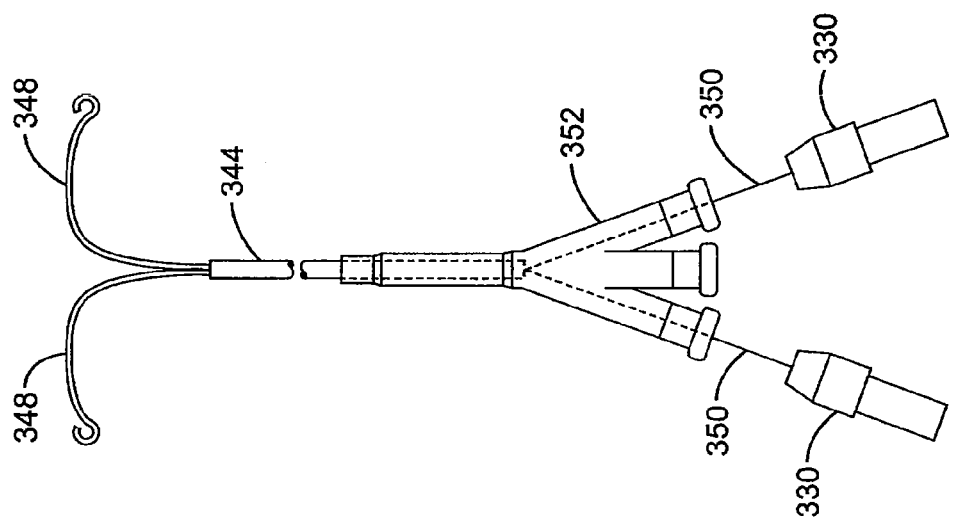
FIG. 41 is another bifurcated catheter as shown in FIG. 40 where both moveable distal extensions may be manipulated independently by guide wire.

FIG. 41 is another embodiment of a bifurcated catheter 344 shown in FIG. 40 where each moveable distal extensions 348 may be manipulated independently by respective guide wires 350 connected through proximal coupler 354 to respective handles 330. This configuration allows the physician to guide each distal extension 348 into its respective target artery (not shown).

Figure 42:
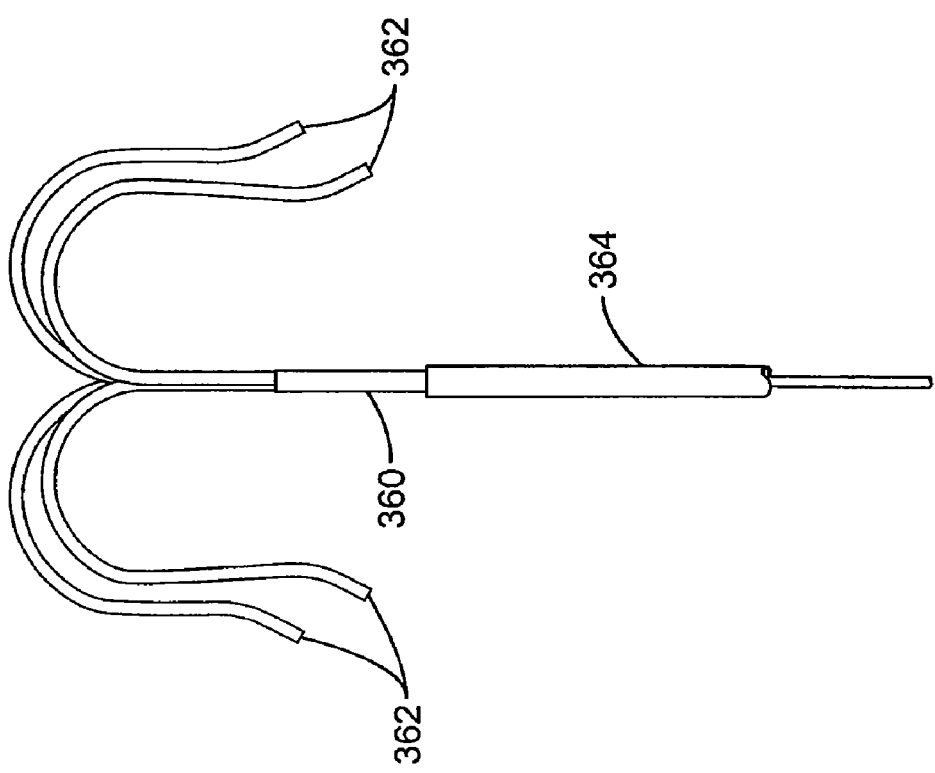
FIG. 42 illustrates a bifurcated infusion catheter with four preformed distal extensions.

FIG. 42 illustrates a delivery catheter 360 with four pre-formed distal extensions 362 in their free state with introducer sheath 364 retracted. Distal extensions 362 may be adapted to include unique radiopaque markings (not shown) such that each distal extension can be uniquely identified under fluoroscopy.

Figure 43:
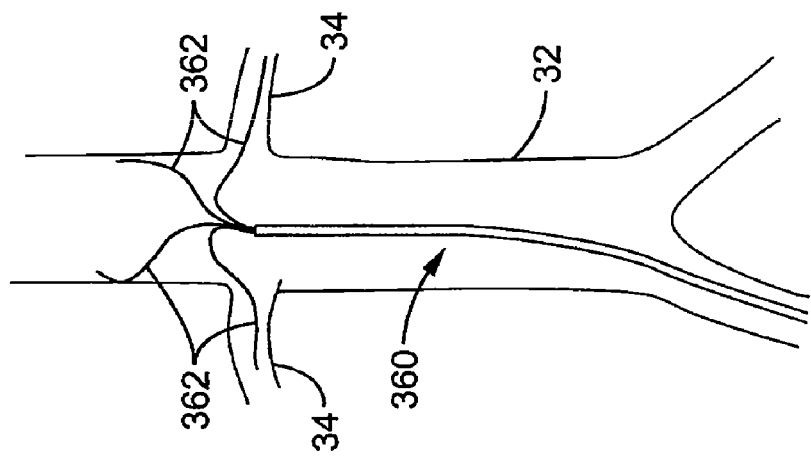
FIG. 43 is a stylized illustration of the catheter as shown in FIG. 42 with two extensions positioned in renal arteries.

FIG. 43 is a stylized illustration of catheter 360 shown in FIG. 43 in aorta 32 with two of the four distal extensions 362 positioned in renal arteries 34. By way of example and not of limitation, two of four distal extensions 362 in renal arteries 34 are sufficient to deliver required materials in particular cases. By way of additional example and not of limitation, individual distal extensions 362 may include various unique radiopaque markings (not shown) that correspond to identification on an adjustable fluid inlet manifold (also not shown) such that the user may select the proper infusion lumens corresponding to the cannulated distal extensions, and thus deliver selected agent only to the distal extensions in the renal arteries.

Figure 44:
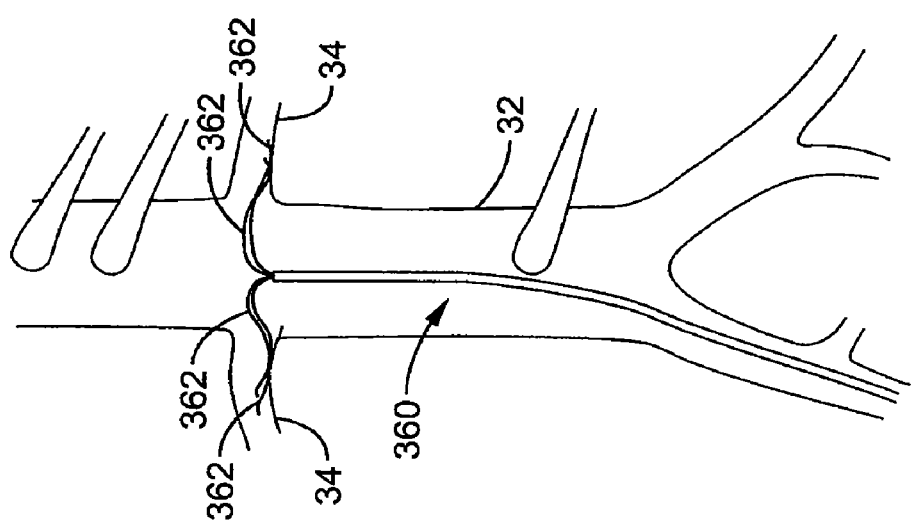
FIG. 44 is a stylized illustration of the catheter as shown in FIG. 42 with four extensions positioned in renal arteries.

FIG. 44 is a stylized illustration of catheter 360 shown in FIG. 42 in aorta 32 with four distal extensions 362 positioned in renal arteries 34. As noted above, distal extensions 362 may incorporate unique radiopaque markings allowing them to be individually identified under fluoroscopy.

Figure 45:
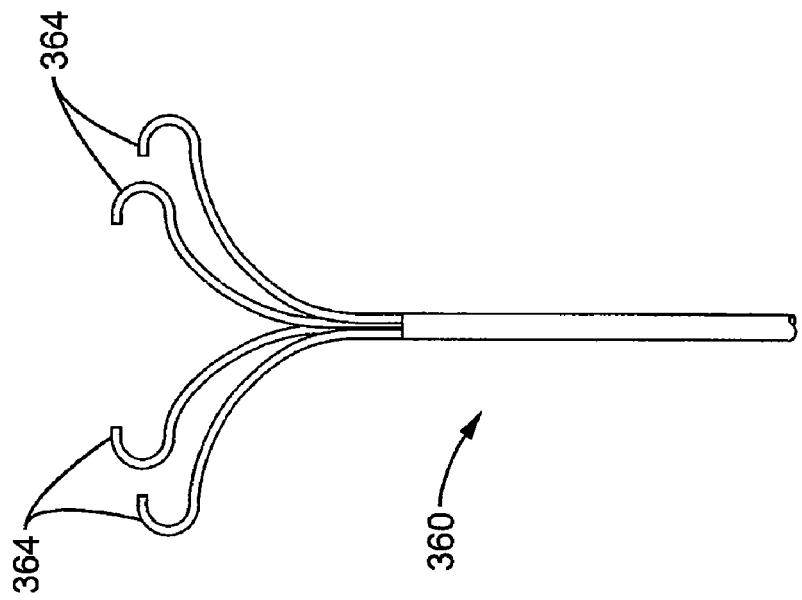
FIG. 45 illustrates another beneficial embodiment of a renal infusion catheter with multiple preformed distal extensions.

FIG. 45 illustrates another embodiment of catheter 360 with pre-formed distal extensions 364 in another beneficially pre-formed shape.

Figure 46:
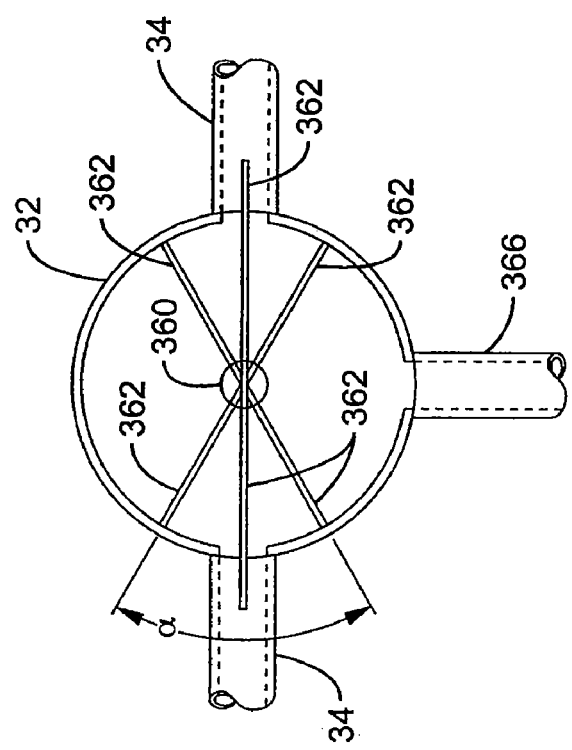
FIG. 46 illustrates a schematic cross section of an aorta at the intersection of the renal arteries with a multiple distal extension catheter deployed.

FIG. 46 illustrates a schematic cross section of an aorta 32 at the intersection of renal arteries 34 viewed looking down on the distal extensions of the catheter 360. Delivery catheter 360, with a plurality of distal extensions 362, is positioned within the relatively narrow angle α illustrating that this arrangement of distal extensions 362 will accommodate natural anatomy configurations without interference with the superior mesenteric artery 366 located above renal arteries 34. Testing demonstrates that at least one extension on each side will "find" that side's renal, providing for selective infusion. A proximal coupler assembly (not shown) can be configured to select the appropriate extensions for infusion (via a system of corresponding radiopaque markers on the extensions and the coupler assembly).

Figure 47:
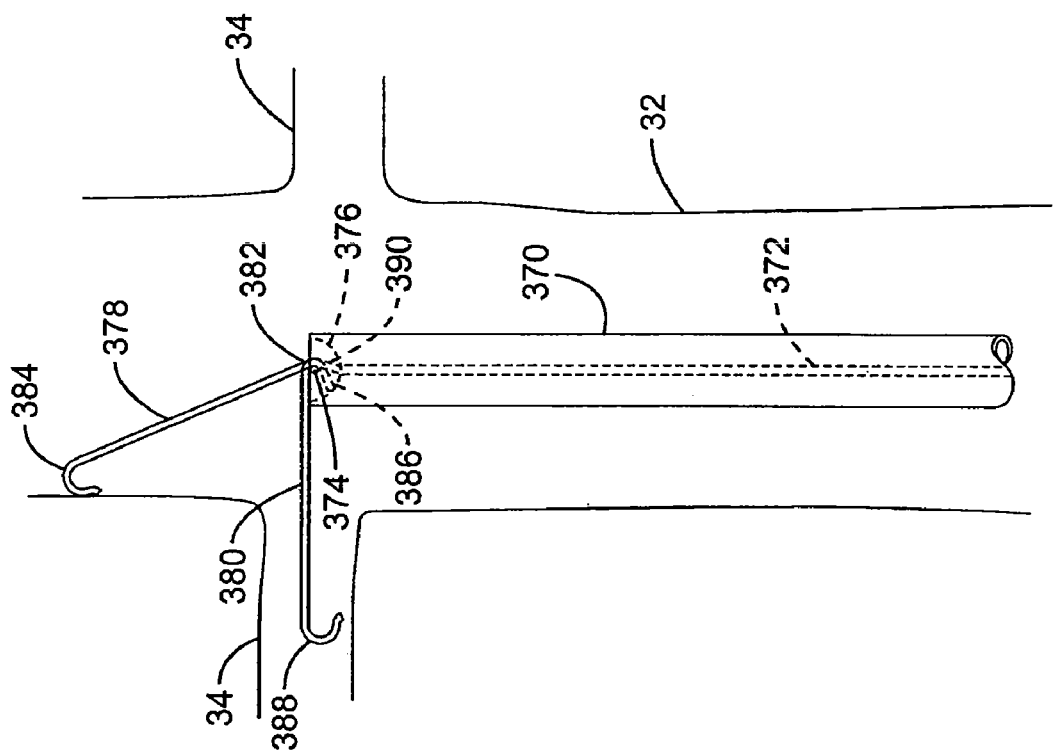
FIG. 47 is a stylized illustration of an infusion catheter with multiple pivoting distal extensions.

FIG. 47 is a stylized illustration of a delivery catheter 370 with a single infusion lumen 372. Details on the right of catheter 370 have been omitted for clarity. A pivot post 374 is positioned horizontally over a concave opening 376 of delivery catheter 370. Concave opening 376 is in fluid communication with infusion lumen 372. Tubular extensions 378 and 380 are configured to rotate on pivot post 374 at preformed bend 382. Delivery catheter 370 is inserted in aorta 32 near the renal arteries 34. Tubular extension 378 is positioned with its distal end 384 in contact with the wall of aorta 32 and its pivot end 386 is in contact with the surface of concave opening 376. In this position, tubular extension 378 is not in fluid communication with infusion lumen 372. As catheter 370 is manipulated in aorta 32, distal end 388 of tubular extension 380 enters renal artery 34 and rotates to a position on pivot post 374 such that pivot end 390 of tubular extension 380 is in fluid communication with infusion lumen 372 and can deliver materials directly into renal artery 34. Thus, if a tubular extension 388 selects a renal artery 34 (as it is no longer constrained by aortic wall 32), upon rotation around the pivot post 374, the selected tubular extension 388 is automatically placed into fluid communication with the catheter's infusion lumen 372.

FIG. 48A through FIG. 48G illustrate one sequence of steps in a method of constructing a single lumen delivery catheter with multiple distal extensions. Distal extensions may have pre-formed shapes for cannulation. In the embodiment shown in FIG. 48A, one or more tubular members T with dimensions of approximately 0.028 inches inside diameter and about 0.036 inches outside diameter and of material such as Pebax, is cut at 402 at an acute angle at proximal end 404. Cut tubular member T becomes distal extension 400.

In FIG. 48B, mandrels 406, preferably having a suitable nonstick coating such as TFE, is inserted in distal extensions 400 past the proximal end 404.

FIG. 48C illustrates a step where a flared tube 408 has a proximal end 410, a flared distal end 412, and is about 0.049 inches inside diameter to about 0.057 inches outside diameter. The proximal end 404 of distal extensions 400 with mandrels 406, are inserted into the flared distal end 412 of flared tube 408.

Figure 48D:
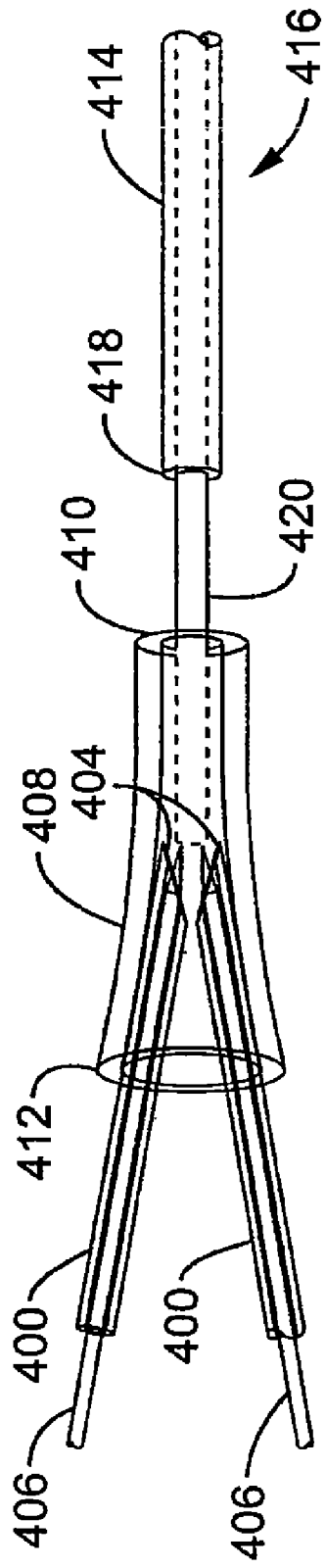
FIG. 48D illustrates another step in constructing a multiple distal extension catheter.

FIG. 48D illustrates a step where the outer cover 414 of a hypotube 416 is cut at the distal portion 418 to expose inner tube 420. Exposed inner tube 420 is inserted in proximal end 410 of flared tube 408.

Figure 48E:
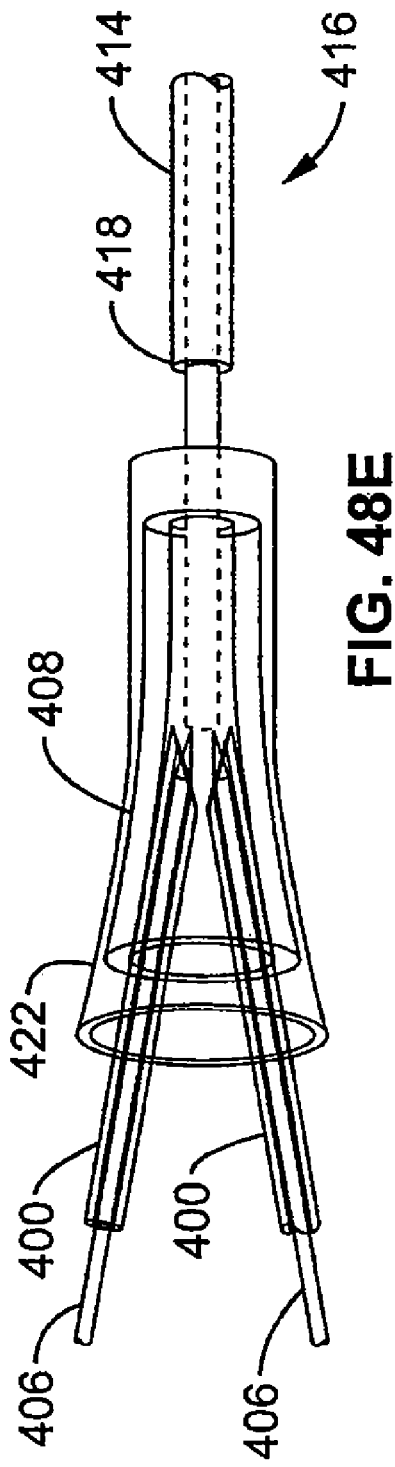
FIG. 48E illustrates a further step in constructing a multiple distal extension catheter.

FIG. 48E illustrates a step where flared tube 408 and exposed inner tube 420 is covered and fused with a thermal shrink-wrap 422.

FIG. 48F illustrates a step where preferably a tube 424 of about 0.055 inches inside diameter and about 0.064 inches outside diameter, and of material such as Pebax, is placed over thermal shrink wrap 422, to cover the proximal end 412 of flared tube 408 and the distal end 418 of the outer cover 414 of hypotube 416. Tube 424 is preferably fused to shrink wrap 422 at a temperature of about 400° F.

FIG. 48G illustrates a step where a cover tube 426 of about 0.070 inches inside diameter and about 0.090 inches outside diameter and of material such as Pebax, is placed to cover the proximal end 412 of flared tube 408, tube 424 and the distal end 418 of the outer cover 414 of hypotube 416 in the embodiment shown. Cover tube 426 is fused to outer cover 414 of hypotube 416 and tube 424 at about 400° F. The mandrels 406 are then removed from the distal extensions 400 resulting in multiple distal extensions 400 in fluid communication with hypotube 416.

FIG. 49 through FIG. 53 is a stylized illustration of another embodiment of an anchoring catheter for use in the venous system 450 with a femoral vein 452 and a renal vein 454. This embodiment is used to increase renal perfusion and function by reducing the venous pressure of the renal system. This may be particularly effective for patients displaying renal hypoperfusion resulting in fluid overload or threatened or actual acute renal failure. Further, using the device in the venous system reduces medical complications and trauma due to the lower pressures involved. In FIG. 49, a multilumen drain catheter 456 with a drain sleeve 458 at the distal tip 460 is inserted in renal vein 454 with return sleeve 462 at a mid proximal region of catheter 456 positioned in femoral vein 452. A proximal coupler assembly 464 is attached at the proximal end of catheter 456 and fluidly connects drain sleeve 458 and return sleeve 462 to a pump (see FIG. 53). An expandable member 466, such as a balloon, is positioned just proximal of the drain sleeve 458 and fluidly connected to an inflation lumen in multilumen catheter 456. The distal tip 460 is positioned in a renal vein 454 through the venous system 450 using conventional insertion methods. The expandable member 466 is inflated or deflated through operation of a syringe (not shown) or a pump (see FIG. 53) at inflation port 468 fluidly connected to the inflation lumen at the proximal coupler 464 (see FIG. 53).

FIG. 50 illustrates the distal tip 460 of the multilumen catheter 456 shown in FIG. 49 inserted in renal vein 454. When expandable member 466 is in an inflated state, renal vein 454 is occluded from venous system 450 and the pressure in renal vein 454 is actively reduced with a reversible pump 468 (shown in FIG. 53) and fluidly connected to drain sleeve 458 in renal vein 454. This configuration may also used to retro-deliver fluid agents to the renal system. In this configuration, the expandable member 466 is periodically inflated to temporarily occlude renal vein 454 from venous system 450. A fluid agent is introduced through a fluid agent lumen (not shown) to the drain sleeve 458 where it perfuses in an anti-grade fashion into the renal system.

Figure 51:
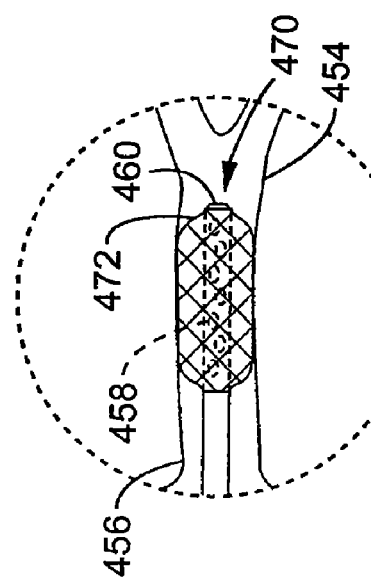
FIG. 51 illustrates another embodiment of a distal tip for the drain catheter system shown in FIG. 50 with an expandable mesh deployed in a renal vein.

FIG. 51 illustrates another embodiment of a distal tip 470 shown in FIG. 50 where an expandable mesh 472 is positioned to enclose drain sleeve 458 in the renal vein 454 and thereby prevent vein collapse from reduced blood pressure. The expandable mesh 472 is activated by a pull wire 490 (see FIG. 53) or other activation means through drain catheter 456.

Figure 52:
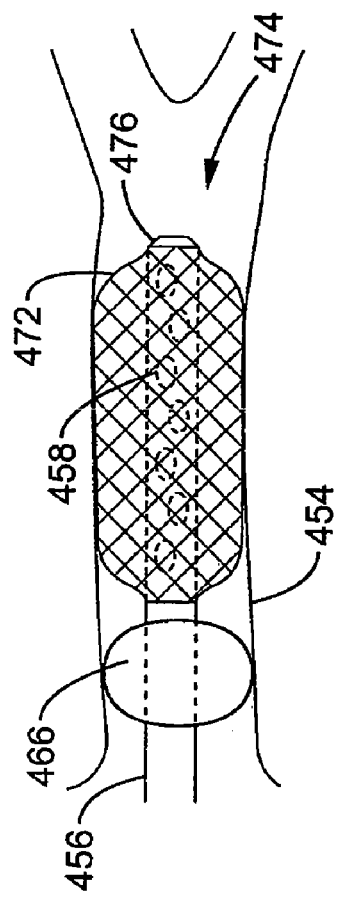
FIG. 52 illustrates a detailed view of another embodiment of a distal tip for the drain catheter system shown in FIG. 50 combining the embodiments shown in FIG. 50 and FIG. 51.

FIG. 52 illustrates another embodiment of a distal tip 474 combining elements of the embodiments shown in FIG. 50 and FIG. 51. Expandable mesh 472 is positioned to enclose drain sleeve 458 at distal end 476 in the embodiment shown. Expandable member 466 is positioned just proximal of expandable mesh 472. Distal tip 474 is inserted in renal vein 454 where expandable member 466 occludes the renal vein 454 and expandable mesh 472 prevents collapse of renal vein 454 due to reduced pressure.

Figure 53:
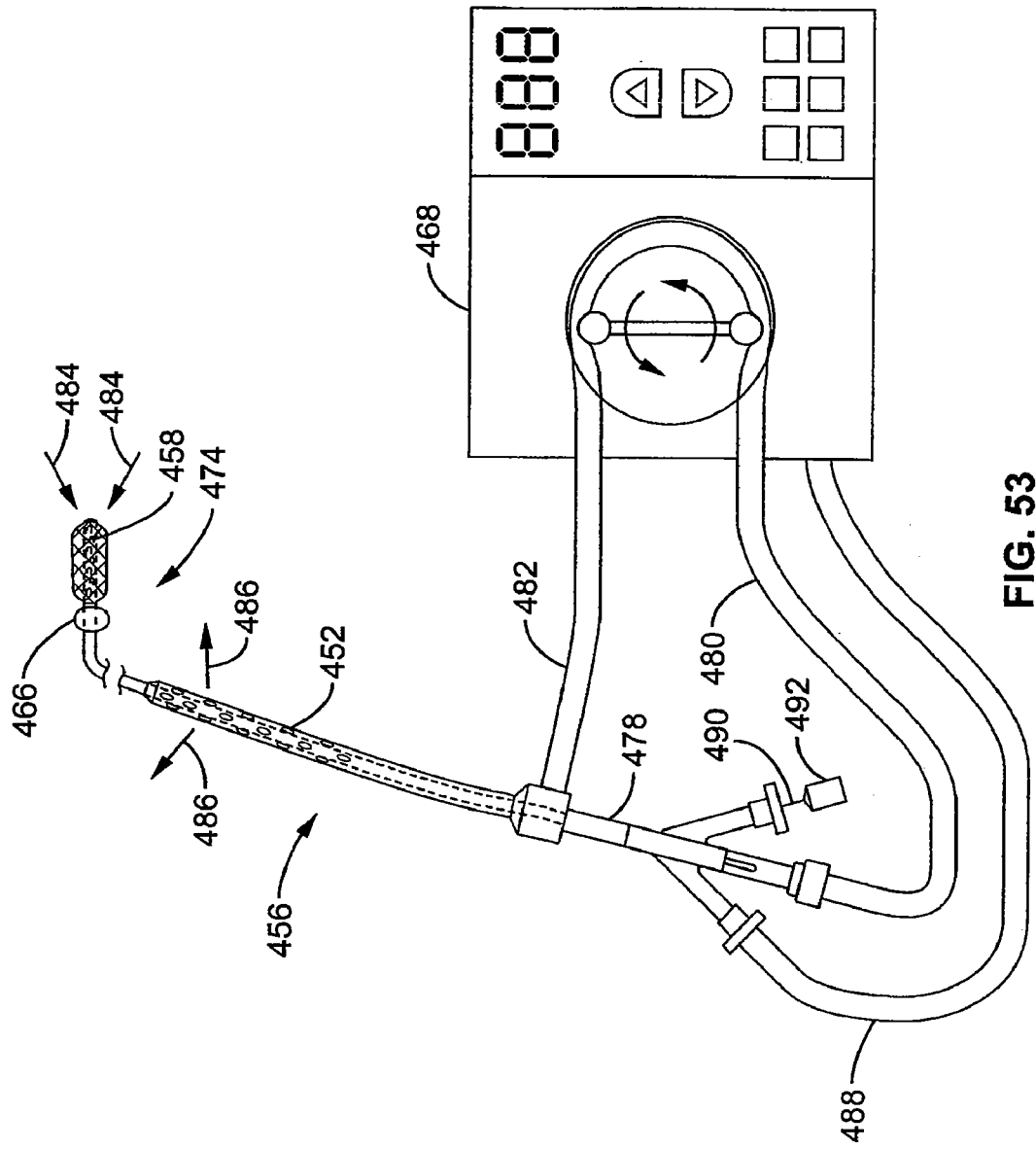
FIG. 53 illustrates a typical reversible roller pump at the proximal end of the drain catheter shown in FIG. 49.

FIG. 53 illustrates a typical reversible roller pump 468 at the proximal end of the drain catheter 456 illustrated in FIG. 49 and connected through proximal coupler 478. Pump 468 extracts blood from distal tip 474 through a drain line 480 fluidly connected to drain sleeve 458 and inserts it back into the venous system through a return line 482 fluidly connected to return sleeve 452. Blood flow arrow 484 shows blood extraction location and blood flow arrow 486 shows blood return location. An inflation tube 488 fluidly connects pump 468 and expandable member 466. Pull wire 490 is attached proximally to control handle 492 and distally to expandable mesh 472 and activates expandable mesh 472. Reversing the direction of pump 468 reverses the blood flow at distal tip 474 and return sleeve 452. This reverse configuration may be used to retro-deliver fluid agents.

FIG. 54 through FIG. 57 illustrates an embodiment of a proximal coupler system 850 used to deploy and position anchoring delivery devices adjunctive with interventional catheters. FIG. 54 and FIG. 55 illustrate a proximal coupler system 850 in side view, and cut away section view, respectively. The Y Hub body 852 is configured with an introducer sheath fitting 854 at the distal end 856 of hub body 852 and a main adapter fitting 858 at the proximal end 860 of Y hub body 852. Main branch 862 has tubular main channel 864 aligned on axis 866. Main channel 862 fluidly connects introducer sheath fitting 854 and main adapter fitting 858. By way of example and not of limitation, one embodiment of main channel 864 is adapted to accommodate a 6 Fr guide catheter. Side port fitting 868 is positioned on main branch 862 and is fluidly connected to main channel 864. Secondary branch 870 has tubular branch channel 872 that intersects main channel 864 at predetermined transition angle β. The preferred transition angle β is approximately 20 degrees. Proximal end 874 of secondary branch 870 has secondary fitting 876. In one beneficial embodiment, a channel restriction 878 is molded into introducer sheath fitting 854. The Y hub body 852 may be molded in one piece or assembled from a plurality of pieces. Alternatively (but not shown) side port fitting 868 may be positioned on secondary branch 870 in a manner similar to positioning on main branch 862 as shown.

Figure 56A:
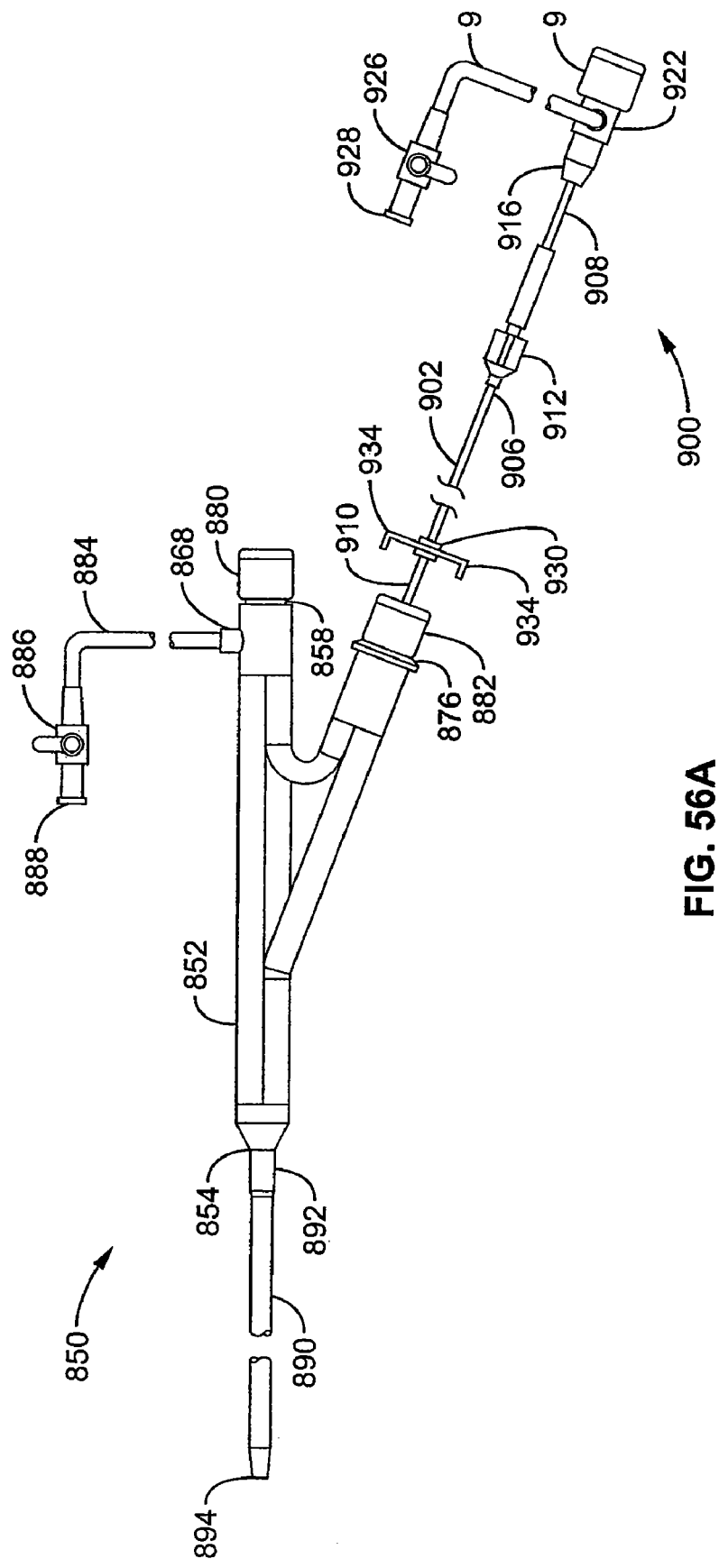
FIG. 56A illustrates a proximal coupler assembly as shown in FIG. 54 coupled to a local fluid delivery system.
Figure 56B:
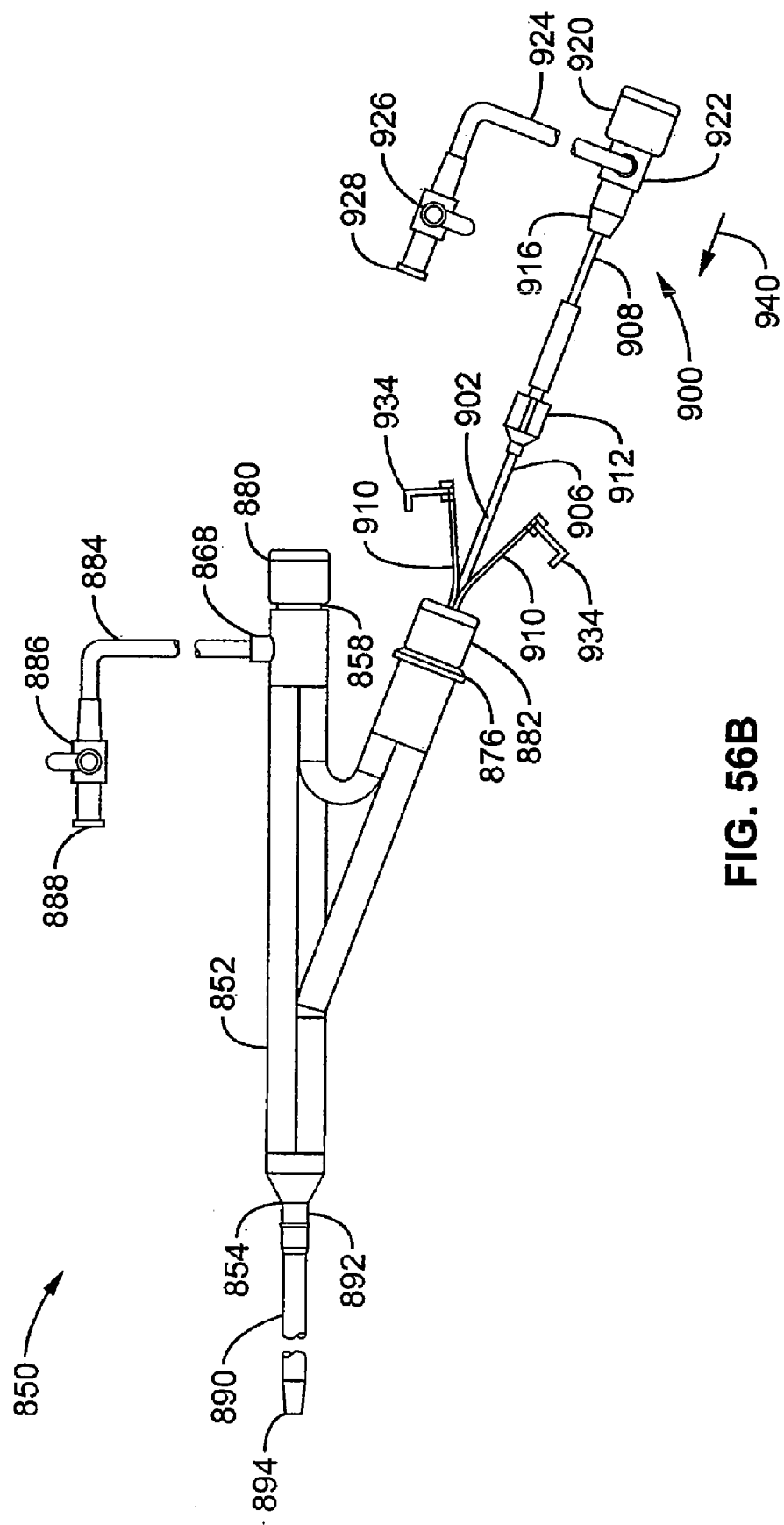
FIG. 56B illustrates a proximal coupler assembly as shown in FIG. 56A with the local fluid delivery system advanced in an introducer sheath.

FIG. 56A and FIG. 56B illustrate a proximal coupler system 850 with a hemostasis valve 880 attached at main port 858 and Touhy Borst valve 882 attached at branch port 876. Fluid tube 884 is coupled to side port 868 and fluidly connects stop valve 886 and fluid port 888. Introducer sheath 890 with proximal end 892 and distal end 894 is coupled to Y hub body 852 at sheath fitting 854. Proximal coupler system 850 is coupled to a local fluid delivery system 900. A stiff tube 902, has a distal end 904 (shown in FIG. 57), a mid proximal section 906, and a proximal end 908. In one embodiment, stiff tube 902 is made of a Nickel-Titanium alloy. Stiff tube 902 is encased in delivery sheath 910 distal of mid proximal section 906. By way of example and not of limitation, delivery sheath 910 may be about 6 Fr to about 8 Fr in diameter. A torque handle 912 is coupled to stiff tube 902 at a mid proximal position 906. A material injection port 916 is positioned at the proximal end 908 of stiff tube 902. Material injection port 916 is coupled to an adapter valve 920 for introducing materials such as fluids. Side port fitting 922 is coupled to tube 924 and further coupled to stopcock 926 and fluid fitting 928. In an exemplary embodiment, adaptor 920 is a Luer fitting. In another exemplary embodiment, side port fitting 922 is used for injecting a saline solution. Delivery sheath handle 930 is positioned and attached firmly at the proximal end 932 of delivery sheath 910. Delivery sheath handle 930 has two delivery handle tabs 934. In an exemplary embodiment, delivery sheath handle 930 is configured to break symmetrically in two parts when delivery handle tabs 934 are forced apart.

In FIG. 56B, Delivery sheath 910 is inserted through Touhy Borst adapter 882 through secondary branch channel 872 until distal end (not shown) of delivery sheath 910 is against channel restriction 878 (see FIG. 55). At that point, force 940 is applied in a distal direction at torque handle 912 to push stiff tube 902 through delivery sheath 910. In FIG. 56B, stiff tube 902 has been advanced through into introduction sheath 890 and past the distal end 894 of introduction sheath 890. Optionally in one mode, delivery sheath handle 930 is split in two by pressing inwardly on delivery handle tabs 934. Delivery sheath 910 may be split by pulling delivery tabs 934 of handle 930 apart and retracted from Y hub body 852 to allow a medical intervention device like that shown in FIG. 57 to enter hemostasis valve 880 for further advancement through main channel 864 (see FIG. 55) and adjacent to stiff tube 902. As way of example and not of limitation, delivery sheath 934 may be removed from Y hub body 852 through Touhy Borst valve 882 before spitting and removing from stiff tube 902.

Figure 57:
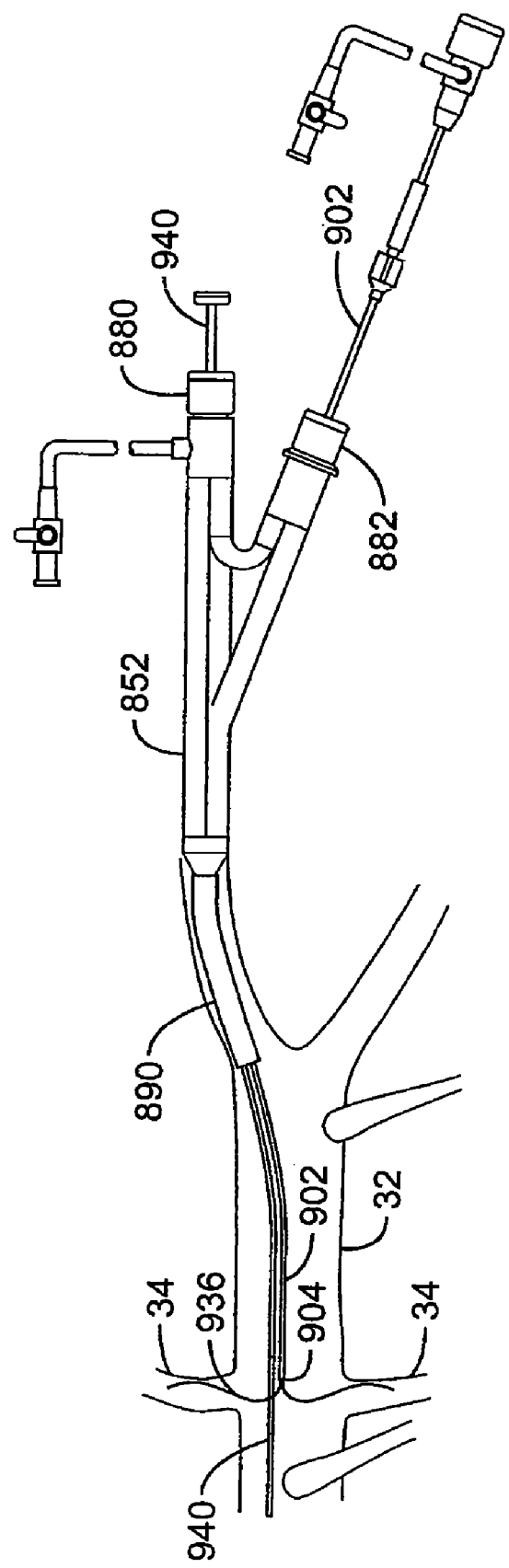
FIG. 57 illustrates a proximal coupler assembly as shown in FIG. 54 through 56B with a fluid infusion device deployed in the renal arteries and a catheter simultaneously deployed in the aorta.

FIG. 57 is an illustration of the proximal coupler system 850 of FIG. 56B with introducer sheath 890 inserted in aorta system 32. Delivery sheath 910 (not shown) of local fluid delivery system 900 has been retracted proximally and removed and one or more fluid agent infusion devices 936 at distal end 904 of stiff tube 902 have been advanced and positioned at renal arteries 34. Interventional catheter 940 enters hemostasis valve 880 and is advanced through introducer sheath 890 and past fluid agent infusion device 936 for further medical intervention at a remote location distal to the renal arteries while fluid agent infusion device 936 remains in place at renal arteries 34. It is to be understood that proximal coupler systems can be further modified with additional branch ports to advance and position more than two devices through a single introducer sheath.

Figure 58:
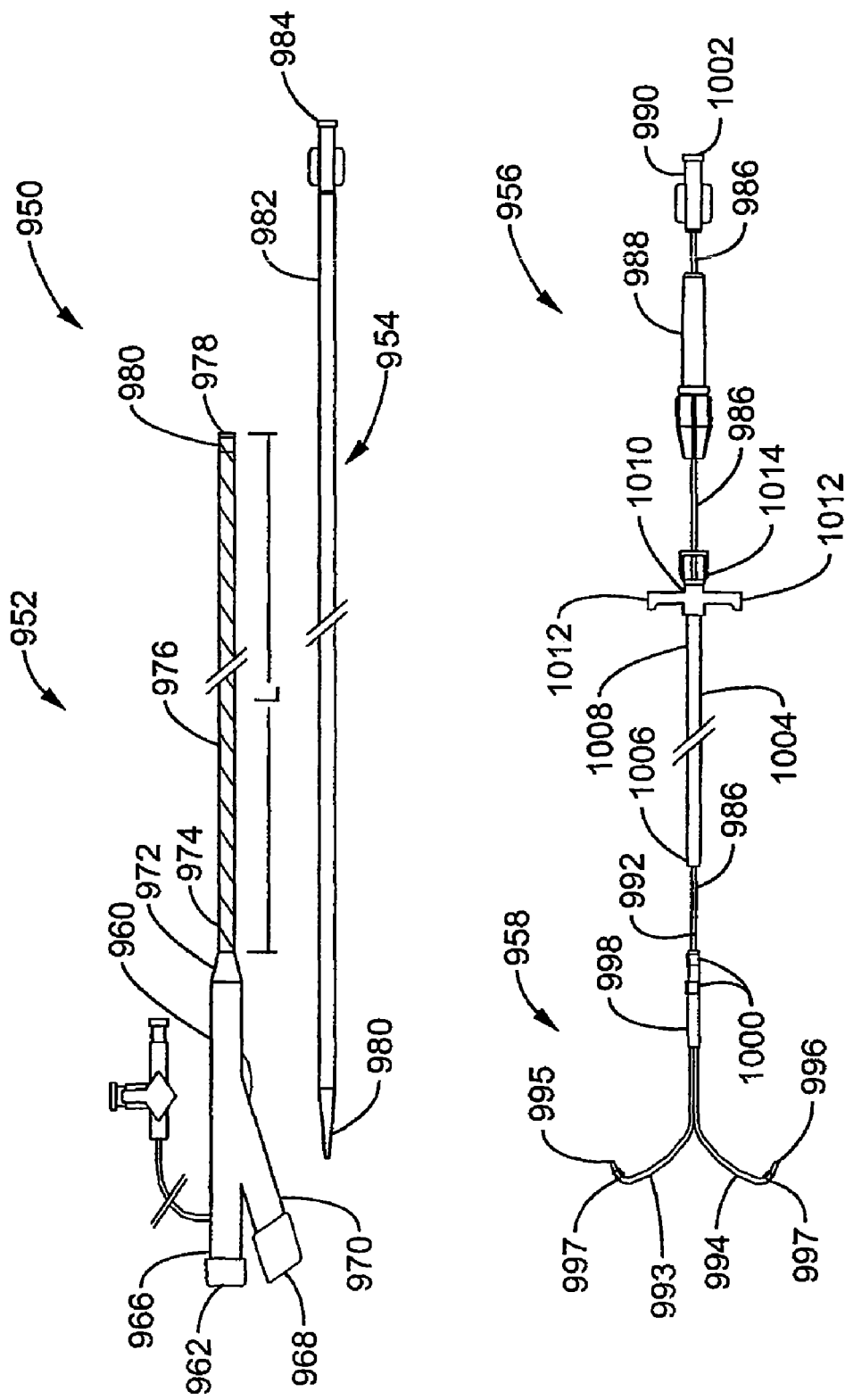
FIG. 58 illustrates a renal therapy system with an introducer sheath system, a vessel dilator, a fluid delivery system and a bifurcated catheter.

FIG. 58 illustrates a further embodiment of the proximal coupler assembly and fluid delivery assembly that is shown in FIG. 57. Renal therapy system 950 includes an introducer sheath system 952, a vessel dilator 954 and a fluid delivery system 956 with a bifurcated renal catheter 958. Details of channels, saline systems and fittings as shown previously in FIG. 54 through FIG. 57 are omitted for clarity. Introducer sheath system 952 has Y hub body 960 as shown previously in FIG. 54 and FIG. 55 configured various inner structures as shown previously in FIG. 55. Y hub body 960 has hemostasis valve 962 on proximal end 966 and Touhy Borst valve 968 on secondary end 970. Distal end 972 of Y hub body 960 is coupled to proximal end 974 of introducer sheath 976. Introducer sheath 976 has distal tip 978 that has a truncated cone shape and radiopaque marker band 980. In one embodiment, introducer sheath 976 is constructed with an inner liner of PTFE material, an inner coiled wire reinforcement and an outer polymer jacket. Introducer sheath 976 has predetermined length L measured from proximal end 974 to distal tip 978.

Vessel dilator 954, with distal end 980 and proximal end 982 is preferably a polymer, (e.g. extrusion tubing) with a center lumen for a guide wire (not shown). Distal end 980 is adapted with a taper cone shape. Proximal end 982 is coupled to a Luer fitting 984.

Fluid delivery system 956 has stiff tube 986, torque handle 988, and proximal hub 990 as previously described in FIG. 56A and FIG. 56B with bifurcated catheter 958 coupled at distal end 992. Bifurcated catheter 958 has two distal extensions 993, 994 composed partially of a memory shape material. Distal tips 995, 996 of each distal extension 993, 994 respectively, have a plurality of fluid ports (not shown) and radiopaque marker bands 997. Polymer tube 998 is positioned proximal of distal extensions 993, 994 and has radiopaque marker bands 1000. The proximal hub 990 of fluid delivery system 956 preferably has a Luer fitting 1002 for infusing a fluid agent that is fluidly coupled with the stiff tube 986.

A single lumen, tear-away delivery sheath 1004 has a distal end 1006, a proximal end 1008, and slidingly encases stiff tube 986. Delivery sheath 1004 is positioned between the torque handle 988 and the bifurcated catheter 958. The distal end 1006 of sheath 1004 has a shape and outer diameter adapted to mate with the channel restriction in the distal end of the main channel of the Y hub body as shown previously in FIG. 55. The proximal end 1008 of the delivery sheath 1004 is coupled to a handle assembly 1010 with two handles 1012 and a tear away cap 1014.

Dilator 954 is inserted through Touhy Borst valve 968 on secondary port 970 until distal end 980 protrudes from distal tip 978 of introducer sheath 976 to form a smooth outer conical shape. Distal tip 978 of introducer sheath 976 is positioned in the aorta system near the renal arteries (not shown). Dilator 954 is removed and fluid delivery device 956 is prepared by sliding delivery sheath 1004 distally until distal extensions 993, 994 of bifurcated catheter 958 are enclosed in delivery sheath 1004. Distal end 1006 of delivery sheath 1004 is inserted in Touhy Borst valve 968 and advanced to the restriction in the main channel of the Y hub body shown in FIG. 55. Bifurcated catheter 958 is advanced distally into introducer sheath 976. Tear away delivery sheath 1004 is retracted and removed through Touhy Borst valve 968 as shown previously in FIG. 56B. Bifurcated catheter 958 is advanced distally out of the distal tip 978 of introducer sheath 976 and distal extensions 993, 994 expand to their preformed shape to cannulate the renal arteries as shown in FIG. 57.

FIG. 59 is a stylized illustration of a double Y proximal coupler 1150 with two local fluid delivery systems 1152, 1154 and an intervention catheter 1156 in an aorta system 1158. Details of local fluid delivery systems 1152, 1154 are shown in FIGS. 56A and 56B and are omitted here for clarity. The double Y proximal coupler 1150 is constructed similar to a proximal coupler assembly as shown in FIG. 54 and FIG. 55 but with another branch port added. Secondary branch 1160 accommodates local fluid delivery system 1152 for drug infusion in right renal artery 1162. Tertiary branch 1164 accommodates local fluid delivery system 1154 for drug infusion in left renal artery 1166. Intervention catheter 1156 enters double Y proximal coupler 1150 through hemostasis valve 1168. Introduction sheath 1170 is sized to accommodate local fluid delivery systems 1152, 1154 and catheter 1156 simultaneously. FIG. 59 illustrates secondary branch 1160 and tertiary branch 1164 on the same side of the double proximal coupler, however they may be positioned on opposite sides or in another beneficial configuration. By way of example and not of limitation, the cross section of local fluid delivery system 1152, 1154 may be oval shaped. By way of example and not of limitation, double Y proximal coupler 1150 may be adapted to advance a wide mix of medical devices such as guide wires, diagnostic catheters, flow diverters and infusion assemblies through introducer sheath 1170 and into a vascular system such as aorta system 1158.

Notwithstanding the particular benefits provided by the various embodiments described above, one particular highly beneficial embodiment of an overall renal therapy system as shown previously in FIG. 58 is provided as follows in order to further illustrate certain aspects of the invention considered suitable for bi-lateral local renal delivery of therapeutic agents in many circumstances.

An introducer sheath system is comprised of a Y hub body coupled to an introducer sheath. The Y hub body as shown previously in FIG. 54 through FIG. 55 is preferably made of a clear material and is configured with a main channel and a secondary channel that intersects the main channel. The distal end of the main channel is configured with a channel restriction as shown in FIG. 55. The Y hub body has an introducer sheath fitting at the distal end and a port for the introduction of a saline solution into the main channel of the Y hub body. A hemostasis valve is attached to the proximal fitting on the main branch of the Y hub body and is configured to accommodate a nominal 6 French diameter catheter. A Touhy Borst valve is attached to the secondary fitting on the secondary port of the Y hub body.

An introducer sheath is coupled to the introducer sheath fitting of the Y hub body and is constructed with an inner liner of TFE material, an inner coiled wire reinforcement and an outer polymer jacket. The nominal 8 French introducer sheath has an inner diameter of about 0.116 inches and an outer diameter of about 0.138 inches. The distal tip is shaped as a truncated cone to adapt with the distal tip of a vessel dilator and has a radiopaque marker band. The proximal end of the introducer sheath is comprised of the outer polymer jacket only and is flared to couple to the introducer sheath fitting on the Y hub body. In one highly beneficial embodiment, multiple introducer sheaths are provided with a renal therapy system to accommodate different anatomies. Introducer sheaths with nominal usable lengths L, as shown in FIG. 58, of about 30 cm, about 35 cm, about 40 cm, and about 45 cm are typically included, but other suitable lengths can be provided as well. In the present example, the different length introducer sheaths are each coupled to a Y body hub as an integrated introducer sheath system, however, the system may be packaged and sold separately for later assembly. In one example, a renal therapy system has a plurality of introducer sheath systems, each with a different length introducer sheath.

A vessel dilator is used with this renal therapy system to guide the distal tip of the introducer sheath to the proximal region of the renal arteries. The vessel dilator is a polymer extrusion, tapered at the distal end with an inner lumen of about 0.040 inches and adapted for passage of a guide wire of about 0.035 inches to about 0.038 inches in diameter. The vessel dilator useable length is at least nominally about 11 cm longer than the usable length of the corresponding introducer sheath to allow for placement through the introducer sheath and the Y hub body. The proximal end of the vessel dilator has a Luer fitting, primarily for flushing the inner lumen with a saline solution.

After the position of the renal arteries relative to the percutaneous entry point has been established using a guide wire with a diagnostic catheter and methods known to exist in the art, an integrated introducer sheath system of suitable length is selected. The vessel dilator is introduced through the Touhy Borst valve on the secondary branch of the Y hub and advanced until the distal t of the vessel dilator protrudes from the distal tip of the introducer sheath resulting in a smooth outer conical shape. A saline flush is introduced through the port on the Y body and the proximal port of the vessel dilator. The introducer sheath with vessel dilator inserted is advanced on the guide wire through the percutaneous entry point and to the region in the aorta of the renal arteries. The marker band on the distal tip of the introducer sheath may be used with fluoroscopy to aid in positioning. When the distal tip of the introducer sheath is positioned at or near the renal arteries, the vessel dilator and guide wire are retracted, and removed, from the Y hub body through the Touhy Borst valve while the introducer sheath remains in place.

A fluid delivery system as previously shown in FIG. 56A is prepared for insertion into the Y hub body. In this embodiment, the fluid delivery system has a stiff tube made of Nitinol tubing and is about 77 cm in usable length with a distal end, a mid proximal portion and a proximal end. A bifurcated catheter, as previously shown in FIG. 35, is coupled at the distal end of the stiff tube. The distal extensions of the bifurcated catheter have a memory shape and are made of a braid-reinforced polymer with an inner core of ribbon wire. Each distal extension in this example has a radiopaque marker band and two infusion ports at or near the distal tip. The outside diameter of each of the distal extensions nominally about 3 French. There is a polymer tube encasing the bifurcated catheter in a position proximal of the union of the distal extensions. The polymer tube has two radiopaque markers positioned about 1 cm to about 1.5 cm proximal of the union of the distal extensions to aid in relative positioning of the bifurcated catheter and the introducer sheath.

The fluid delivery system has a torque handle coupled at the mid proximal portion of the stiff tube and a proximal hub coupled at the proximal end of the stiff tube. The proximal hub has a Luer fitting for infusing a fluid agent and a saline flush port fluidly coupled with the stiff tube.

A single lumen, tear-away delivery sheath slidingly encases the stiff tube and is positioned between the torque handle and the bifurcated catheter. The delivery sheath is nominally about 15 cm in length with a distal end and a proximal end. The distal end has a shape and outer diameter adapted to mate with the channel restriction in the distal end of the main channel of the Y hub body as shown previously in FIG. 55. The proximal end of the delivery sheath is coupled to a handle assembly with two handles. The handle assembly has a tear away cap on the proximal end and is configured to allow the handle assembly to separate into two portions when the tear-away cap is removed and the handles pulled apart. The circumferential profile of the delivery sheath is configured with opposing thin wall sections to facilitate splitting lengthwise in two pieces when the handles are pulled apart.

The fluid delivery system is prepared by flushing saline solution from the saline port in the stiff tube proximal hub through to infusion ports in the distal extension tips of the bifurcated catheter. The bifurcated catheter is loaded into the delivery sheath by pulling the catheter stiff tube or torque handle proximally relative to the delivery sheath handle until the tips of the distal extensions of the bifurcated catheter are completely within the delivery sheath.

The distal end of the delivery sheath, with the bifurcated catheter loaded, is inserted through the Touhy Borst valve on the secondary port of the Y hub body until the distal end seats in the channel restriction in the main channel. Distal force on the torque handle of the stiff tube advances the bifurcated catheter into the introducer sheath, preferably to at least about 15 cm (about the length of the tear away delivery sheath) into the introducer sheath to ensure the distal extensions are completely out of the tear away delivery sheath and into the introducer sheath.

The tear away delivery sheath is retracted from the Y hub body by pulling in a proximal position on the delivery sheath handle assembly as previously described in FIG. 56B. During the delivery sheath retraction, the bifurcated catheter remains in position in the introducer sheath. When the distal end of the delivery sheath is removed from the Y hub body, the Touhy Borst valve is tightened on the stiff tube to prevent fluid loss. The tear away cap is removed from the delivery sheath handle assembly and the handles are pulled apart, tearing the delivery sheath longitudinally and into two pieces, which are removed from the stiff tube and discarded.

The bifurcated catheter is advanced to the distal tip of the introducer sheath by distal movement of the stiff tube at the torque handle relative to the Y hub body. Using fluoroscopic guidance, the bifurcated catheter is advanced out of the distal tip of the introducer sheath. The bifurcated catheter is manipulated through the torque handle, and the introducer sheath is simultaneously retracted, and the distal extensions bias toward their memory shape in the aorta and cannulate the renal arteries. Once the distal extensions are completely extended out of the distal tip of the introducer sheath and positioned in the renal arteries, the distal tip of the introducer sheath is retracted at least just proximal of the marker bands on the polymer tube of the bifurcated catheter to allow for interventional catheter advancement, while the bifurcated catheter remains in place. With the introducer sheath positioned, the Touhy Borst valve is tightened to prevent further movement of the bifurcated catheter in the introducer sheath.

The introducer sheath may be sutured or otherwise positionally controlled at or near the percutaneous entry site to prevent sheath movement during the subsequent procedure. Fluid agent may now be delivered through the proximal port of the fluid delivery system, through the stiff tube and into the renal arteries through the bifurcated catheter similar to that shown in FIG. 57.

Medical intervention procedures, such as coronary procedures, are initiated by inserting the appropriate guide wires and catheters through the hemostasis valve on the proximal fitting of the Y hub body. In this example, a nominal 6 French catheter will advance through the introducer sheath and along side the stiff tube without significant resistance.

When medical interventions are complete, the intervention catheters and guide wires are retracted and removed from the Y hub body through the hemostasis valve. Fluid agent delivery is typically then stopped, but may alternatively be continued for a period of time following therapy. The Touhy Borst valve is loosened and the torque handle of the stiff tube is pulled proximally relative to the Y hub body, withdrawing the distal extensions of the bifurcated catheter out of the renal arteries and into the introducer sheath. The introducer sheath is retracted from the percutaneous entry point and the entry point closed with standard medical procedures.

It is to be appreciated that various embodiments herein described are illustrative of certain broad aspects of the invention that are considered highly beneficial. In particular, the specifically named components, elements, or features for each embodiment may be similarly illustrative of certain broad aspects of the invention shared with other embodiments, though different names or labels may be given, or they may vary in insubstantial ways with respect to such broad aspect. Such would be apparent to one of ordinary skill based upon the totality of this disclosure.

Certain particular embodiments described above illustrate certain highly beneficial aspects of the invention that provide for bi-lateral self-cannulation of renal arteries via their respective ostia that are at spaced locations along an abdominal aorta wail. By "self-cannulation", it is generally meant that the device may be guided to and inserted within the respective ostium without requiring a pre-seated guidewire to provide a railway into the artery. In further beneficial embodiments of this aspect, shape memory recovery following release from confinement distally from an introducer sheath, such as for the arms or legs of the bifurcated catheters, provides an efficient means for a natural outward force against the wall of the aorta. Simply positioning the outwardly biased tip at the correct position along the wall, such that it is registered with the renal ostium, allows it to spring open into the corresponding ostium. As such, helpful assistance may be found through basic torque transmission and longitudinal motion up and down the abdominal aorta to find the right position, and still be considered "self-cannulating" as a guidewire is not used. Or, more manipulative mechanisms may also still be provided, such as deflectability, shaping stylets, etc., in which case the result is considered "controlled self-cannulation", though nonetheless considered self-cannulation if it gets there on its own and without a guide rail.

The various embodiments herein described for the present invention can be useful in treatments and therapies directed at the kidneys such as the prevention of radiocontrast nephropathy (RCN) from diagnostic treatments using iodinated contrast materials. As a prophylactic treatment method for patients undergoing interventional procedures that have been identified as being at elevated risk for developing RCN, a series of treatment schemes have been developed based upon local therapeutic agent delivery to the kidneys. Treatments may be beneficial for low risk patients as well. Among the agents identified for such treatment are normal saline (NS) and the vasodilators papaverine (PAP) and fenoldopam mesylate (FM).

The approved use for fenoldopam is for the in-hospital intravenous treatment of hypertension when rapid, but quickly reversible, blood pressure lowering is needed. Fenoldopam causes dose-dependent renal vasodilation at systemic doses as low as approximately 0.01 mcg/kg/min through approximately 0.5 mcg/kg/min IV and it increases blood flow both to the renal cortex and to the renal medulla. Due to this physiology, fenoldopam may be utilized for protection of the kidneys from ischemic insults such as high-risk surgical procedures and contrast nephropathy. Dosing from approximately 0.01 to approximately 3.2 mcg/kg/min is considered suitable for most applications of the present embodiments, or about 0.005 to about 1.6 mcg/kg/min per renal artery (or per kidney). As before, it is likely beneficial in many instances to pick a starting dose and titrate up or down as required to determine a patient's maximum tolerated systemic dose. Recent data, however, suggest that about 0.2 mcg/kg/min of fenoldopam has greater efficacy than about 0.1 mcg/kg/min in preventing contrast nephropathy and this dose is preferred.

The dose level of normal saline delivered bilaterally to the renal arteries may be set empirically, or beneficially customized such that it is determined by titration. The catheter or infusion pump design may provide practical limitations to the amount of fluid that can be delivered; however, it would be desirable to give as much as possible, and is contemplated that levels up to about 2 liters per hour (about 25 cc/kg/hr in an average about 180 lb patient) or about one liter or 12.5 cc/kg per hour per kidney may be beneficial.

Local dosing of papaverine of up to about 4 mg/min through the bilateral catheter, or up to about 2 mg/min has been demonstrated safely in animal studies, and local renal doses to the catheter of about 2 mg/min and about 3 mg/min have been shown to increase renal blood flow rates in human subjects, or about 1 mg/min to about 1.5 mg/min per artery or kidney. It is thus believed that local bilateral renal delivery of papaverine will help to reduce the risk of RCN in patients with pre-existing risk factors such as high baseline serum creatinine, diabetes mellitus, or other demonstration of compromised kidney function.

It is also contemplated according to further embodiments that a very low, systemic dose of papaverine may be given, either alone or in conjunction with other medical management such as for example saline loading, prior to the anticipated contrast insult. Such a dose may be on the order for example of between about 3 to about 14 mg/hr (based on bolus indications of approximately 10-40 mg about every 3 hours—papaverine is not generally dosed by weight). In an alternative embodiment, a dosing of 2-3 mg/min or 120-180 mg/hr. Again, in the context of local bilateral delivery, these are considered halved regarding the dose rates for each artery itself.

Notwithstanding the particular benefit of this dosing range for each of the aforementioned compounds, it is also believed that higher doses delivered locally would be safe. Titration is a further mechanism believed to provide the ability to test for tolerance to higher doses. In addition, it is contemplated that the described therapeutic doses can be delivered alone or in conjunction with systemic treatments such as intravenous saline.

It is to be understood that the invention can be practiced in other embodiments that may be highly beneficial and provide certain advantages. For example radiopaque markers are shown and described above for use with fluoroscopy to manipulate and position the introducer sheath and the intra renal catheters. The required fluoroscopy equipment and auxiliary equipment devices are typically located in a specialized location limiting the in vivo use of the invention to that location. Other modalities for positioning intra renal catheters are highly beneficial to overcome limitations of fluoroscopy. For example, non-fluoroscopy guided technology is highly beneficial for use in operating rooms, intensive care units, and emergency rooms, where fluoroscopy may not be readily available or its use may cause undue radiation exposure to users and others due to a lack of specific radiation safeguards normally present in angiography suites and the like. The use of non-fluoroscopy positioning allows intra renal catheter systems and methods to be used to treat other diseases such as ATN and CHF in clinical settings outside of the angiography suite or catheter lab.

In one embodiment, the intra renal catheter is modified to incorporate marker bands with metals that are visible with ultrasound technology. The ultrasonic sensors are placed outside the body surface to obtain a view. In one variation, a portable, noninvasive ultrasound instrument is placed on the surface of the body and moved around to locate the device and location of both renal ostia. This technology is used to view the aorta, both renal ostia and the intra-renal catheter, or combinations or sub-combinations thereof.

In another beneficial embodiment, ultrasound sensors are placed on the introducer sheath and/or the intra-renal catheter itself; specifically at the tip of the distal extensions, along the distal extensions or at the distal end of the catheter. The intra-renal catheter with the ultrasonic sensors implemented therewith allows the physician to move the sensors up and down the aorta to locate both renal ostia.

A further embodiment incorporates Doppler ultrasonography with the intra-renal catheters. Doppler ultrasonography detects the direction, velocity, and turbulence of blood flow. Since the renal arteries are isolated along the aorta, the resulting velocity and turbulence is used to locate both renal ostia. A further advantage of Doppler ultrasonography is it is non-invasive and uses no X-rays. According to this mode, a Doppler sensor may be included for example along branch members to be cannulated into renal arteries via their ostia in order to indicate the relative positions versus what is desired.

A still further embodiment incorporates optical technology with the intra renal catheter. An optical sensor is placed at the tip of the introducer sheath. The introducer sheaths optical sensor allows visualization of the area around the tip of the introducer sheath to locate the renal ostia. In a further mode of this embodiment, a transparent balloon is positioned around the distal tip of the introducer sheath. The balloon is inflated to allow optical visual confirmation of renal ostium. The balloon allows for distance between the tip of the introducer sheath and optic sensor while separating aorta blood flow. That distance enhances the ability to visualize the image within the aorta. In a further mode, the balloon is adapted to allow profusion through the balloon wall while maintaining contact with the aorta wall. An advantage of allowing wall contact is the balloon can be inflated near the renal ostium to be visually seen with the optic sensor. In another mode, the optic sensor is placed at the distal tips of the intra renal catheter. Once the intra renal catheter is deployed within the aorta, the optic sensor allows visual confirmation of the walls of the aorta. The intra renal catheter is tracked up and down the aorta until visual confirmation of the renal ostia is found. With the optic image provided by this mode, the physician can then track the intra renal catheter into the renal arteries to a predetermined depth.

Another embodiment uses sensors that measure pressure, velocity, and/or flow rate to locate renal ostia without the requirement of fluoroscopy equipment. The sensors are positioned at the tip of distal extensions of the intra renal catheter. The sensors display real time data about the pressure, velocity, and/or flow rate. With the real-time data provided, the physician locates both renal ostia by observing the sensor data when the intra renal catheter is around the approximate location of the renal ostia. In a further mode of this embodiment, the intra renal catheter has multiple sensors positioned at a mid distal and a mid proximal position on the catheter to obtain mid proximal and mid distal sensor data. From this real time data, the physician can observe a significant flow rate differential above and below the renal arteries and locate the approximate location. With the renal arteries being the only significant sized vessels within the region, the sensors would detect significant changes in any of the sensor parameters.

In a still further embodiment, chemical sensors are positioned on the intra renal catheter to detect any change in blood chemistry that indicates to the physician the location of the renal ostia. Chemical sensors are positioned at multiple locations on the intra renal catheter to detect chemical change from one sensor location to another.

It is to be appreciated therefore according to the immediately preceding embodiments that such relate to a more general aspect of the invention that provides for sensor-assisted guidance to locate the bilateral renal delivery system without the need for, or certain substantially reduced requirement of, fluoroscopic imaging. In particular such reduces a need for radiocontrast delivery to position the respective devices appropriately in reference to the renal arteries, wherein radiocontrast is problematic to begin with for the renal systems of many patients to be given therapy according to the present embodiments. Moreover, it is also to be appreciated such alternative modes just described may be incorporated in combination with other(s) of such modes, or in combination with radiopaque markers or dye delivery to provide a versatile enhanced system. Still further, such beneficial modes according to the embodiments just described are contemplated for use with other bilateral renal delivery systems, such as for example: systems adapted to cannulate each of two renal arteries; systems adapted to position one or more injection ports at desired positions within the abdominal aorta so as to inject agent into regions of blood flowing into the renal arteries via their ostia; and systems adapted to provide isolation, occlusion, or diversion of certain regions of abdominal aortic flow in order to either enhance flow of blood or injected agents into the renal system via their ostia along the abdominal aorta wall. Moreover, the use of such sensors may be performed by monitoring changes in sensed parameters, indicating a change in environment indicative of a desired or un-desired placement. Or, such may be performed by recognition of one or more signature signals of such parameter that are empirically known to indicate a particular position within a patient's anatomy.

Additional modifications or improvements may be made by the embodiments shown and described herein without departing from the intended scope of the invention which is considered to be broadly beneficial according to various independent aspects described. For example, various modifications to or combinations with the present embodiments may be made in view of other available information to one of ordinary skill in the art upon review of this disclosure and remain within the intended scope of the invention.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method for treating a renal system in a patient, comprising:
   positioning a first port of a first renal delivery member at a first delivery position within a first renal artery via a first corresponding renal ostium located at a first location along an abdominal aorta wall of an abdominal aorta in a patient;
   positioning a second port of a second renal delivery member at a second delivery position within a second renal artery via a second corresponding renal ostium located at a second location along the abdominal aortic wall that is different than the first location;

positioning a proximal coupler assembly externally of the patient when the first and second ports are positioned at the first and second delivery positions, respectively; and delivering a material from outside the patient's body via the proximal coupler assembly, through the first and second ports at the first and second delivery positions, respectively, and into the first and second renal arteries, also respectively.

2. A method for treating a renal system in a patient, comprising:

delivering a distal port of a renal delivery member to a delivery position within a renal artery via a corresponding renal ostium along an abdominal aortic wall;

positioning a proximal coupler assembly externally of the patient when the distal port is positioned at the delivery position;

delivering an anchor in a first configuration to an anchoring position along one of the abdominal aorta or the renal artery within the patient;

adjusting the anchor at the anchoring position from the first configuration to a second configuration that secures the renal delivery member with the distal port substantially retained at the delivery position within the renal artery;

allowing substantial blood flow across the anchoring position when the anchor is in the second configuration at the anchoring position; and delivering material from outside the patient's body via the proximal coupler assembly, through the distal port at the delivery position and into the renal artery.

3. A method for treating a renal system in a patient, comprising:

positioning a distal port of a tubular body of a vascular access system within a vessel having transvascular access to a location along an abdominal aorta associated with first and second renal ostia when a proximal port of the tubular body is located externally of the patient;

introducing first and second renal delivery members of a bi-lateral local renal delivery assembly into the vessel through the tubular body;

delivering first and second ports of the first and second renal delivery members, respectively, to first and second respective delivery positions within first and second renal arteries, respectively, via the first and second renal ostia, also respectively;

introducing a percutaneous translumenal interventional device into the vessel through the tubular body;

delivering a distal end portion of the percutaneous translumenal interventional device to an intervention location across the location while the first and second ports are located at the first and second delivery positions, respectively; and simultaneously delivering material from an external location relative to the patient and directly into each of first and second renal arteries via the first and second ports at the first and second delivery positions, respectively; and wherein the bi-lateral renal delivery assembly and a proximal end portion of the percutaneous translumenal interventional device are simultaneously engaged within the tubular body of the vascular access assembly when the first and second ports are at the first and second delivery positions and the distal end portion of the percutaneous translumenal interventional device is at the intervention location.

4. A method for preparing a bi-lateral renal delivery system for use in treating a patient, comprising:

introducing first and second renal delivery members of a bi-lateral local renal delivery assembly into a tubular body of a vascular access system;

introducing a percutaneous translumenal interventional device into the tubular body;

wherein the bi-lateral renal delivery assembly and the percutaneous translumenal interventional device are simultaneously engaged within the tubular body of the vascular access assembly;

wherein the first and second renal delivery members have first and second ports, respectively, that are adapted to be delivered to first and second respective delivery positions within first and second renal arteries, respectively, via first and second renal ostia, also respectively, having unique locations along the abdominal aorta wall;

wherein the percutaneous translumenal interventional device comprises a distal end portion that is adapted to be delivered to an intervention location across a location along the abdominal aorta associated with the first and second renal ostia while the first and second ports are located at the first and second delivery positions, respectively; and wherein the first and second renal delivery members are coupled to a proximal coupler assembly that is adapted to deliver material from an external location relative to the patient and to the first and second ports so as to deliver the material directly into each of first and second renal arteries via the first and second ports at the first and second delivery positions, respectively; and wherein the tubular body of the vascular access system has a distal port that is adapted to be positioned within a vessel having transvascular access to the location along the abdominal aorta when a proximal port of the tubular body is located externally of the patient.

5. A method for treating a renal system in a patient, comprising:

delivering a distal port of a renal delivery member to a delivery position within a renal vein via its ostium along a vena cava in a patient;

positioning a proximal coupler assembly externally of the patient when the distal port is at the delivery position;

fluidly coupling the proximal coupler assembly to the distal port such that a material may be delivered from outside of the patient through the proximal coupler assembly, through the distal port at the delivery position, and into the renal vein;

delivering an occlusion member in a first configuration to an occlusion position located toward ostium from the delivery position, such that the distal port and occlusion members are located at the delivery and occlusion positions, respectively;

adjusting the occlusion member at the occlusion position from the first configuration to a second configuration so as to substantially occlude flow from the renal vein and into the vena cava;

controlling co-operative operation of the renal delivery assembly and the occlusion member between first and second modes of operation;

wherein in the first mode the occlusion member is in the first configuration at the occlusion position and venous blood is allowed to flow from the kidney and along the renal vein and into the vena cave; and wherein in the second mode the occlusion member is in the second configuration at the occlusion position, venous blood is substantially occluded from flowing from the kidney along the renal vein and into the vena cava, and a volume of fluid agent flows through the distal port at the delivery position and into the renal vein at sufficient pressure to provide retrograde flow into the respective kidney coupled to the renal vein.

6. A method for treating a renal system in a patient, comprising:
- positioning an introducer sheath within an abdominal aorta at a location associated with first and second renal artery ostia associated with first and second renal arteries that perfuse first and second kidneys in the patient;
- delivering a bi-lateral renal delivery assembly in a first configuration under radial confinement through the introducer sheath and to a first position along the location;
- withdrawing the introducer with respect to the bi-lateral renal delivery assembly so as to remove the radial confinement;
- after removing the bi-lateral renal delivery assembly from radial confinement, allowing first and second bifurcating delivery members to self-expand apart from each other and radially against an abdominal aorta wall at the location with shape memory recovery force to a second configuration;
- modifying the position of the self-expanded renal delivery assembly so as to self-cannulate at least one of the delivery members into at least one of the renal arteries via its corresponding ostium along the abdominal aorta wall.

7. The method of claim 6, further comprising torquing the renal delivery assembly in the second configuration.

8. The method of claim 6, further comprising modifying the longitudinal position of the renal delivery assembly in the second configuration.

9. A method for providing local therapy to a renal system in a patient, comprising:
- delivering a bi-lateral local renal delivery assembly to a location within an abdominal aorta corresponding with first and second renal ostium along an abdominal aorta wall of the patient;
- delivering a percutaneous translumenal interventional device to an intervention location across the location corresponding with the renal ostia;
- positioning a first delivery member of the bilateral local renal delivery assembly in a first renal artery via a first ostium along the abdominal aorta wall;
- positioning a second delivery member of the bilateral local renal delivery assembly in a second renal artery via a second ostium along the abdominal aorta wall;
- inserting the bi-lateral local renal delivery assembly and percutaneous translumenal interventional device into the patient's vasculature through a common vascular access site.

* * * * *